(12) United States Patent
Kim et al.

(10) Patent No.: US 10,383,949 B2
(45) Date of Patent: Aug. 20, 2019

(54) COMPOUNDS COMPRISING SELF-IMMOLATIVE GROUP

(71) Applicant: LegoChem Biosciences, Inc., Daejeon (KR)

(72) Inventors: Yong Zu Kim, Daejeon (KR); Tae Kyo Park, Daejeon (KR); Sung Ho Woo, Daejeon (KR); Sun Young Kim, Daejeon (KR); Jong Un Cho, Daejeon (KR); Doo Hwan Jung, Daejeon (KR); Ji Young Min, Daejeon (KR); Hyang Sook Lee, Daejeon (KR); Yun Hee Park, Daejeon (KR); Jeong Hee Ryu, Daejeon (KR); Kyu Man Oh, Daejeon (KR); Yeong Soo Oh, Daejeon (KR); Jeiwook Chae, Daejeon (KR); Ho Young Song, Daejeon (KR); Chul-Woong Chung, Daejeon (KR); Jeon Yang, Daejeon (KR)

(73) Assignee: LegoChem Biosciences, Inc., Daejeon (KR)

( * ) Notice: Subject to any disclaimer, the term of this patent is extended or adjusted under 35 U.S.C. 154(b) by 0 days.

(21) Appl. No.: 16/005,245

(22) Filed: Jun. 11, 2018

(65) Prior Publication Data
US 2018/0353611 A1 Dec. 13, 2018

Related U.S. Application Data

(63) Continuation of application No. 14/898,932, filed as application No. PCT/KR2015/005299 on May 27, 2015, now Pat. No. 9,993,568.

(30) Foreign Application Priority Data

May 28, 2014 (KR) .................. 10-2014-0064360

(51) Int. Cl.
| | |
|---|---|
| A61K 47/68 | (2017.01) |
| C07D 249/04 | (2006.01) |
| C07K 19/00 | (2006.01) |
| C07K 16/32 | (2006.01) |
| A61K 47/69 | (2017.01) |
| C07D 487/04 | (2006.01) |
| C07D 519/00 | (2006.01) |
| A61K 47/54 | (2017.01) |
| A61K 47/50 | (2017.01) |
| A61K 39/00 | (2006.01) |

(52) U.S. Cl.
CPC .......... *A61K 47/6871* (2017.08); *A61K 47/50* (2017.08); *A61K 47/549* (2017.08); *A61K 47/6801* (2017.08); *A61K 47/6803* (2017.08); *A61K 47/6811* (2017.08); *A61K 47/6813* (2017.08); *A61K 47/6855* (2017.08); *A61K 47/6889* (2017.08); *A61K 47/69* (2017.08); *C07D 249/04* (2013.01); *C07D 487/04* (2013.01); *C07D 519/00* (2013.01); *C07K 16/32* (2013.01); *C07K 19/00* (2013.01); *A61K 2039/505* (2013.01); *C07K 2317/24* (2013.01); *C07K 2317/94* (2013.01)

(58) Field of Classification Search
CPC ........ A61K 47/48646; A61K 47/48092; A61K 47/48338; A61K 47/48415; A61K 2039/505; C07K 16/32; C07K 2317/24
USPC ....................................... 424/179.1
See application file for complete search history.

(56) References Cited

U.S. PATENT DOCUMENTS

| | | | |
|---|---|---|---|
| 5,112,739 A | 5/1992 | Meneghini et al. | |
| 5,935,995 A * | 8/1999 | Bosslet ............... | A61K 47/549 514/460 |
| 6,218,519 B1 | 4/2001 | Kenten et al. | |
| 8,039,273 B2 | 10/2011 | Jeffrey | |
| 8,568,728 B2 | 10/2013 | Jeffrey | |
| 9,919,057 B2 | 3/2018 | Kim et al. | |
| 9,993,568 B2 | 6/2018 | Kim et al. | |
| 1,011,896 A1 | 10/2018 | Kim et al. | |
| 10,183,997 B2 | 1/2019 | Kim et al. | |
| 2006/0088522 A1 | 4/2006 | Boghaert et al. | |
| 2012/0107332 A1 | 5/2012 | Jeffrey | |
| 2012/0308584 A1 | 12/2012 | Kim et al. | |
| 2014/0031535 A1 | 1/2014 | Jeffrey | |
| 2014/0032535 A1 | 1/2014 | Singla | |
| 2014/0161829 A1 | 6/2014 | Kim et al. | |
| 2014/0187756 A1 | 7/2014 | Kim et al. | |
| 2014/0286969 A1 | 9/2014 | Tschoepe et al. | |
| 2015/0105541 A1 | 4/2015 | Kim et al. | |
| 2016/0184451 A1 | 6/2016 | Kim et al. | |
| 2016/0257709 A1 | 9/2016 | Kline et al. | |
| 2019/0151465 A1 * | 5/2019 | Kim .................. | A61K 47/6889 |

FOREIGN PATENT DOCUMENTS

| | | |
|---|---|---|
| KR | 10-2015-0137015 | 6/2016 |
| KR | 10-2014-0192328 | 7/2016 |
| RU | 2191021 C2 | 10/2002 |
| WO | WO-2004050089 A1 | 6/2004 |
| WO | WO-2011066418 A1 | 6/2011 |

(Continued)

OTHER PUBLICATIONS

Behrens et al., "Methods for Site-specific Drug Conjugation to Antibodies," MAbs, 6(1): 46-53 (2014).

(Continued)

*Primary Examiner* — Daniel R Carcanague
(74) *Attorney, Agent, or Firm* — Foley Hoag LLP; David P. Halstead; Lucas P. Watkins

(57) ABSTRACT

Provided are compounds comprising a self-immolative group, and the compounds comprising a self-immolative group according to the present invention may include a protein (for example, an oligopeptide, a polypeptide, an antibody, or the like) having substrate-specificity for a target and an active agent (for example, a drug, a toxin, a ligand, a detection probe, or the like) having a specific function or activity.

21 Claims, 17 Drawing Sheets

(56) References Cited

FOREIGN PATENT DOCUMENTS

| WO | WO-2012/153193 A2 | 11/2012 |
|----|----|----|
| WO | WO-2016/040684 A1 | 3/2016 |
| WO | WO-2016/094517 A1 | 6/2016 |
| WO | WO-2016108587 A1 | 7/2016 |
| WO | WO-2017/051249 A1 | 3/2017 |
| WO | WO-2017/051254 A1 | 3/2017 |
| WO | WO-2017089890 A1 | 6/2017 |
| WO | WO-2017089894 A1 | 6/2017 |
| WO | WO-2017089895 A1 | 6/2017 |

OTHER PUBLICATIONS

Bergmann, CP et al. Dental Ceramics. Microstructure, Properties, and Degradation. 2013, Chapter 2, Biomaterials, p. 9.

Carey, FA. Organic Chemistry 6th Ed. McGraw Hill. 2006, chapter 1, p. 9.

Chu et al., "Antibody-drug Conjugates for the Treatment of B-cell Non-Hodgkin's Lymphoma and Leukemia," Future Oncol, 9(3): 355-368 (2013).

Connolly et al., "Discovery of Orally Active 4-amino-6-arylaminopyrimidine-5-carbaldehyde Oximes with Dual EGFR and HER2 Inhibitory Activity," AACR 104th Annual Meeting, Abstract 2456 (2013).

Desbene, S. et al. Doxorubicin prodrugs with reduced cytotoxicity suited for tumour-specific activation. Anti-Cancer Drug Design. 1998, vol. 13, p. 955.

Dunn, PJ. et al. Green Chemistry Principle #8. ACS What is Green Chemistry. Accessed from ACS Website on Jan. 8, 2016.

Extended European Search Report issued by the European Patent Office in corresponding Application No. EP 15799360.1, dated Dec. 21, 2017.

Grinda, M. et al., A Self-Immolative Dendritic Glucuronide Prodrug of Doxorubicin, Medicinal Chemistry Communications, (2012) vol. 3, No. 1, pp. 68-70.

International Search Report and Written Opinion for International Application No. PCT/IB2016/001772 dated Apr. 6, 2017.

International Search Report and Written Opinion for International Application No. PCT/IB2016/001810 dated Apr. 19, 2017.

International Search Report and Written Opinion for International Application No. PCT/IB2016/001811 dated Apr. 19, 2017.

International Search Report and Written Opinion from corresponding International Application Publication No. WO2015182984, publication year: 2015.

Jeffrey et al., Development and properties of β-glucuronide linkers for monoclonal antibody—drug conjugates, Bioconjugate Chem, 17:835 (2006).

Kim et al., "Synthesis of Bispecific Antibodies Using Genetically Encoded Unnatural Amino Acids," J Am Chem Soc, 134: 9918-9921 (2012).

Lartigue, "Antibody-Drug Conjugates: Guided Missiles Deployed Against Cancerous Cells," Oncology Live, p. 1 (2012).

Lee et al., "Enzymatic Prenylation and Oxime Ligation for the Synthesis of Stable and Homogeneous Protein-Drug Conjugates for Targeted Therapy," Angew Chem Int Edit, 54: 1-6 (2015).

Leong, KW. Biomaterials. El Sevier. Accessed on Sep. 26, 2016.

McCombs et al., "Antibody Drug Conjugates: Design and Selection of Linker, Payload and Conjugation Chemistry," AAPS J, 17(2): 339-351 (2015).

Merriam-Webster. Biomaterial Definition. Accessed on Sep. 26, 2016.

Tranoy-Opalinski et al., "β-Glucuronidase-responsive prodrugs for selective cancer chemotherapy: an update," Eur J Med Chem, 74:302-313 (2014).

Wermuth, "Similarity in drugs: reflections on analogue design," Drug Discov Today, 11(Issues 7-8): 248-254 (2006).

Yewale et al., "Epidermal growth factor receptor targeting in cancer: A review of trends and strategies,"Biomaterials, 34: 8690-8707 (2013).

* cited by examiner

[FIG. 1]
[Released mechanism from β-glucuronide linker]
1. When ▢ part is carbamate,
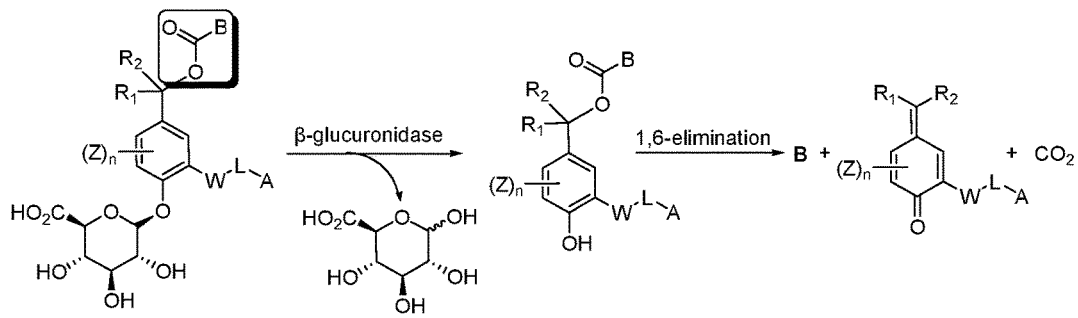
2. When ▢ part is ester,
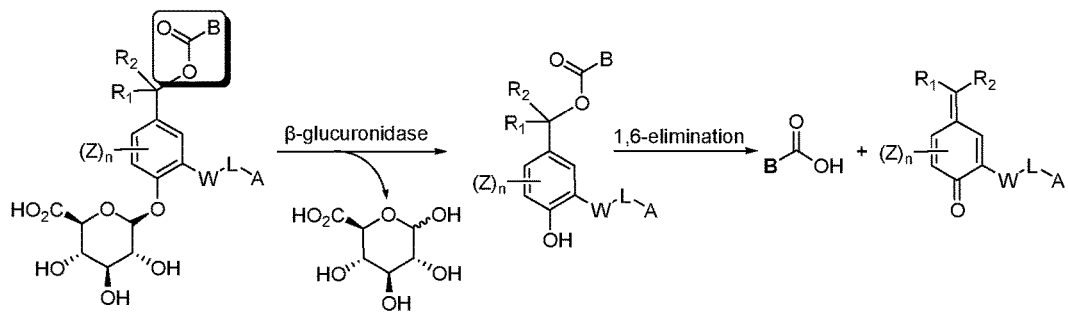

[FIG. 2]
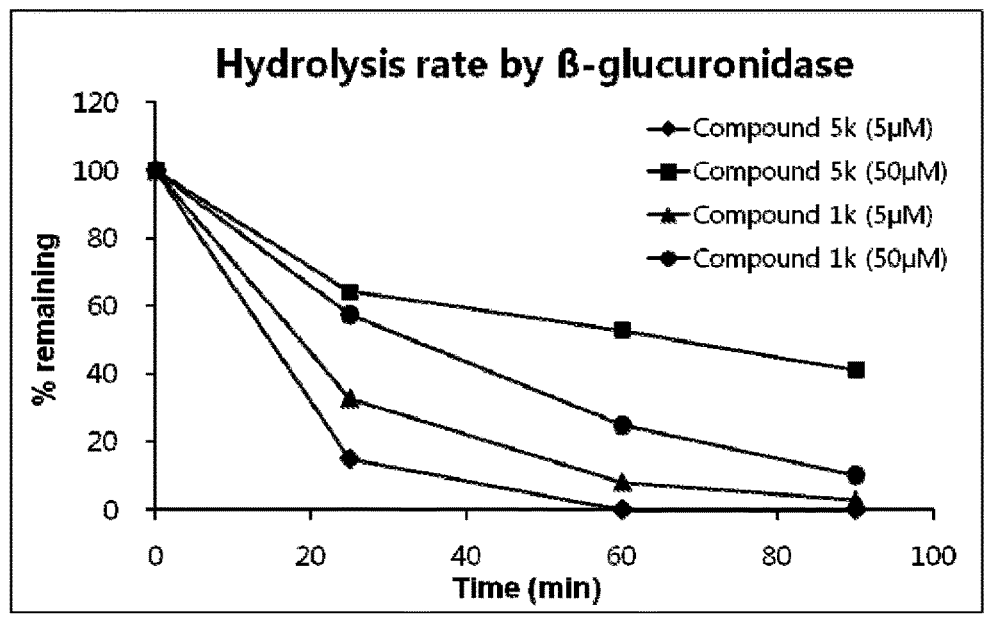
[FIG. 3]
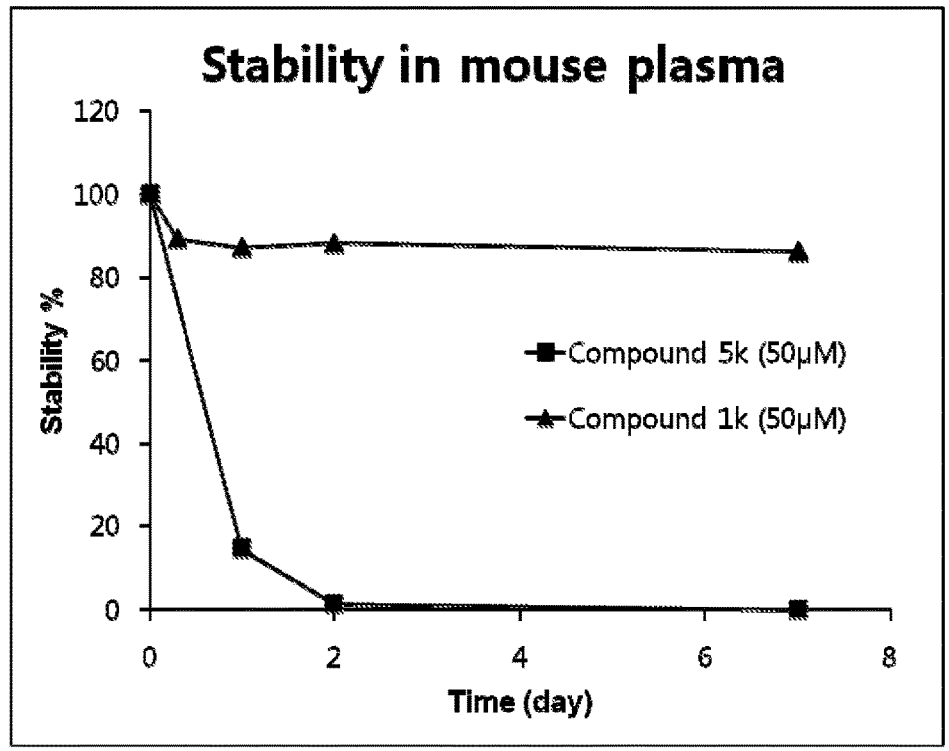

[FIG. 4]
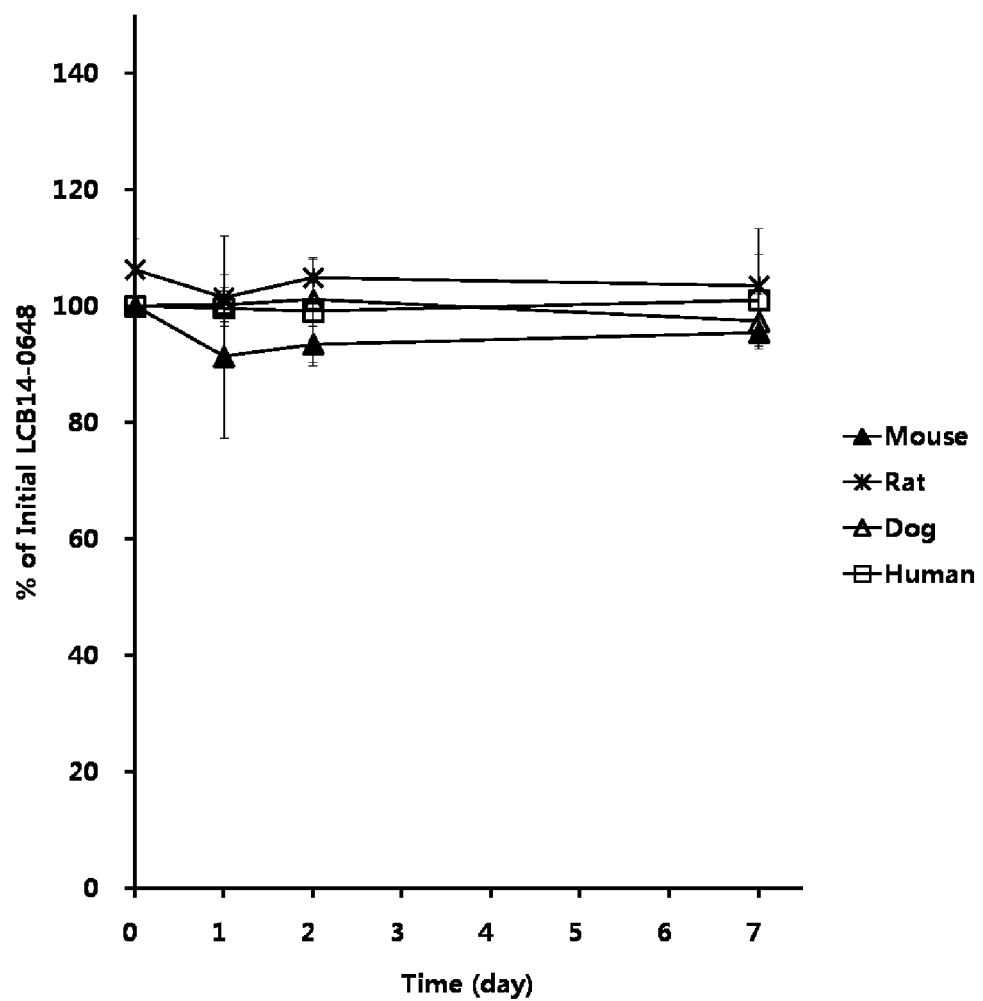

[FIG. 5]
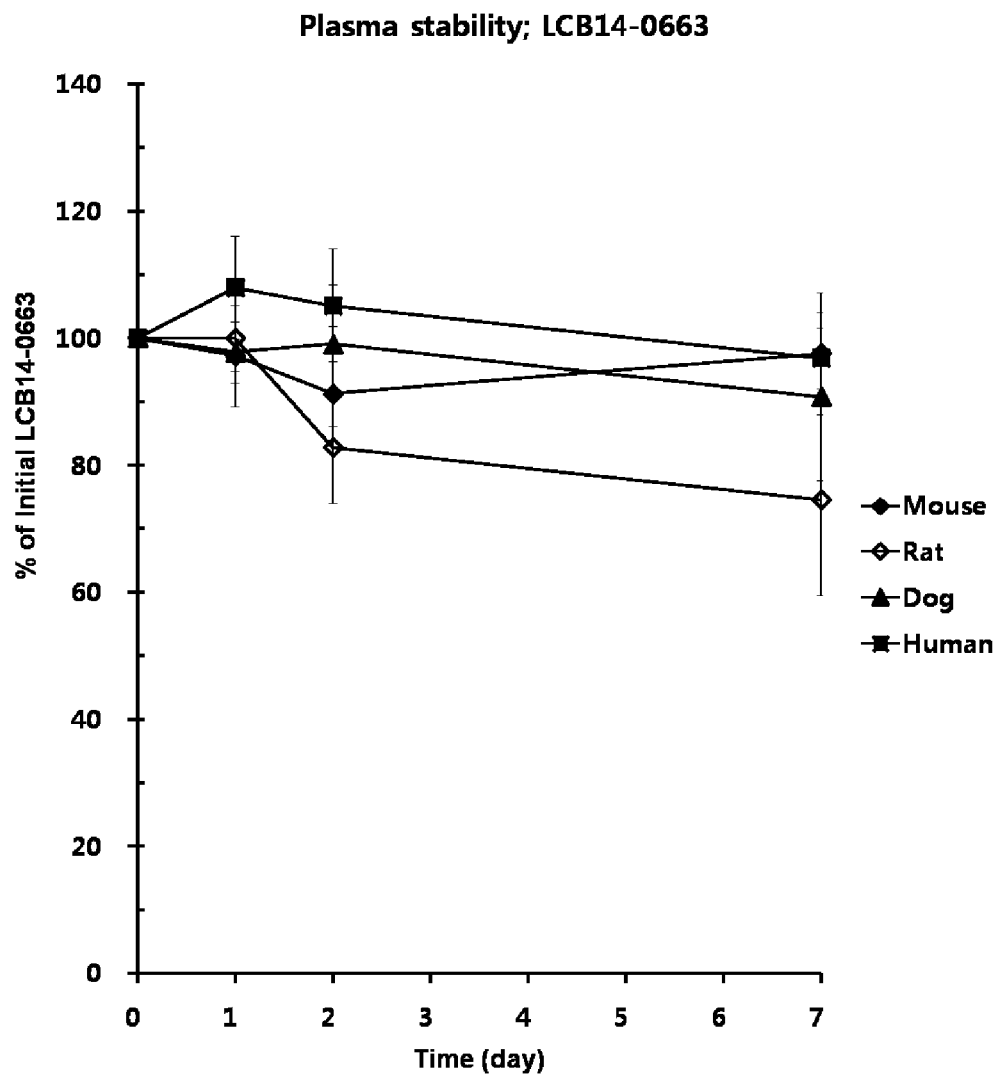

[FIG. 6]
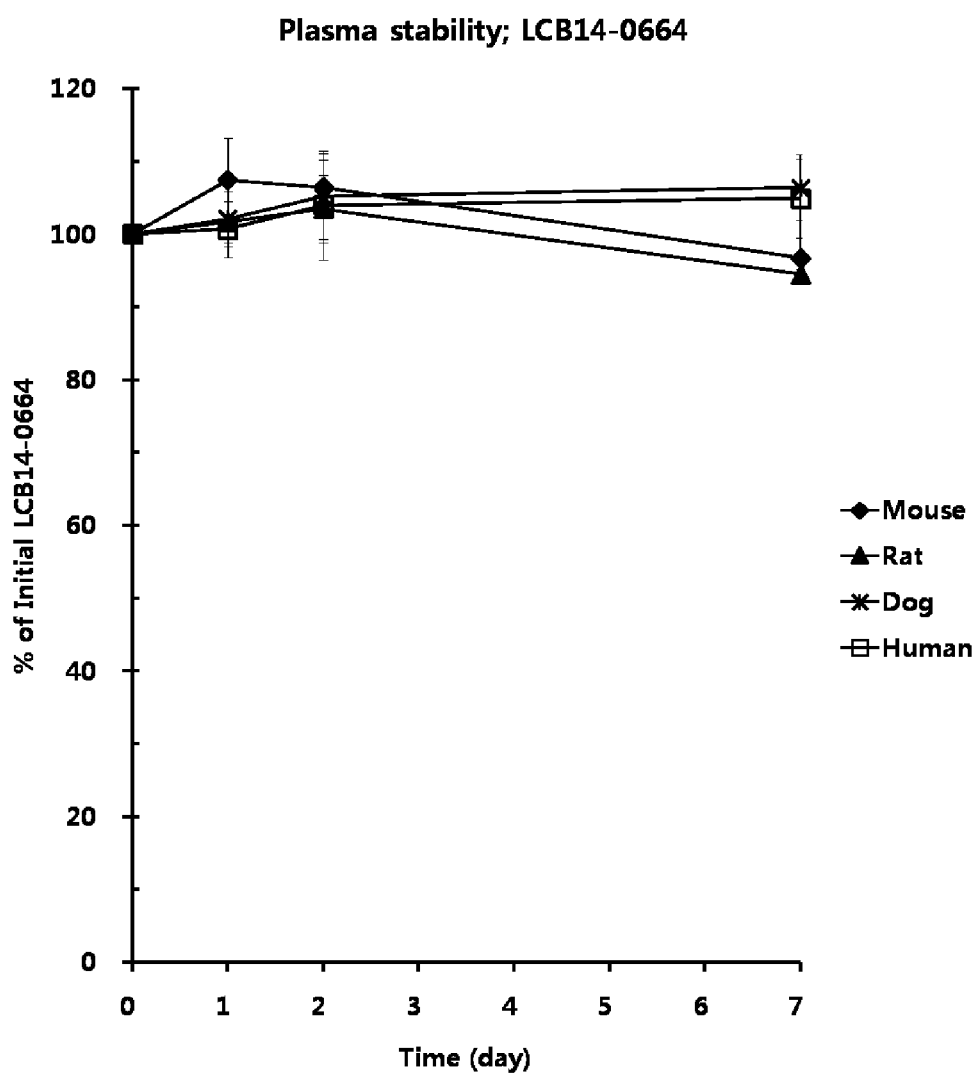

[FIG. 7]
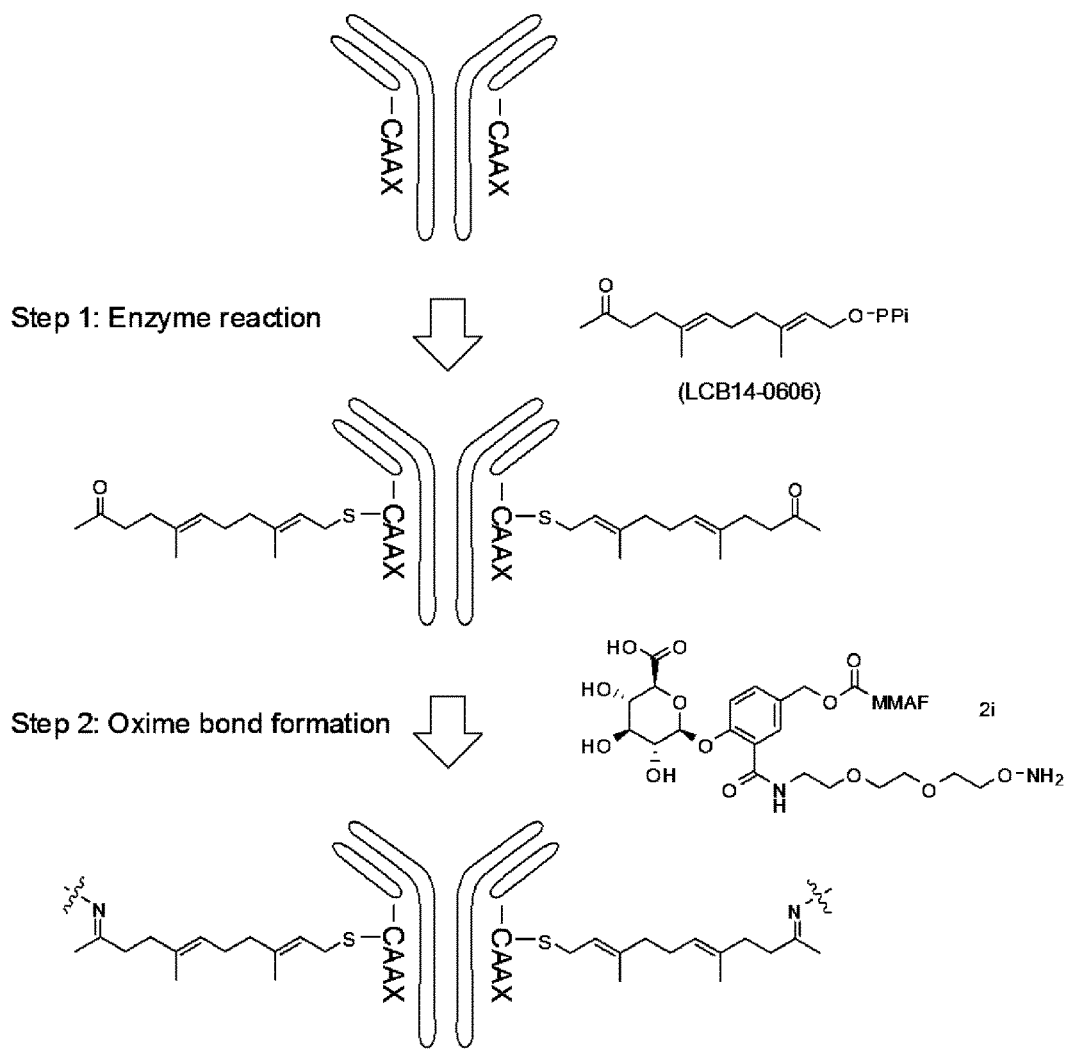

[FIG. 8]
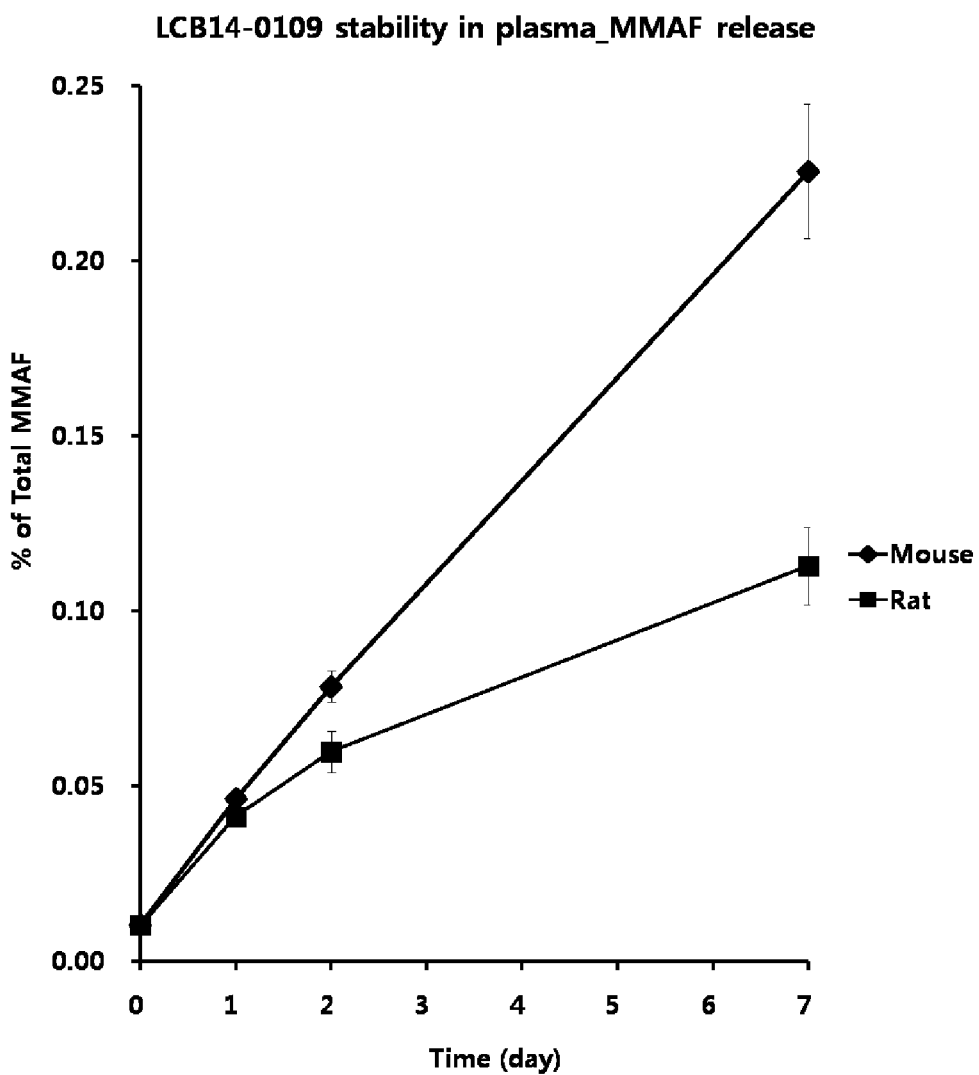

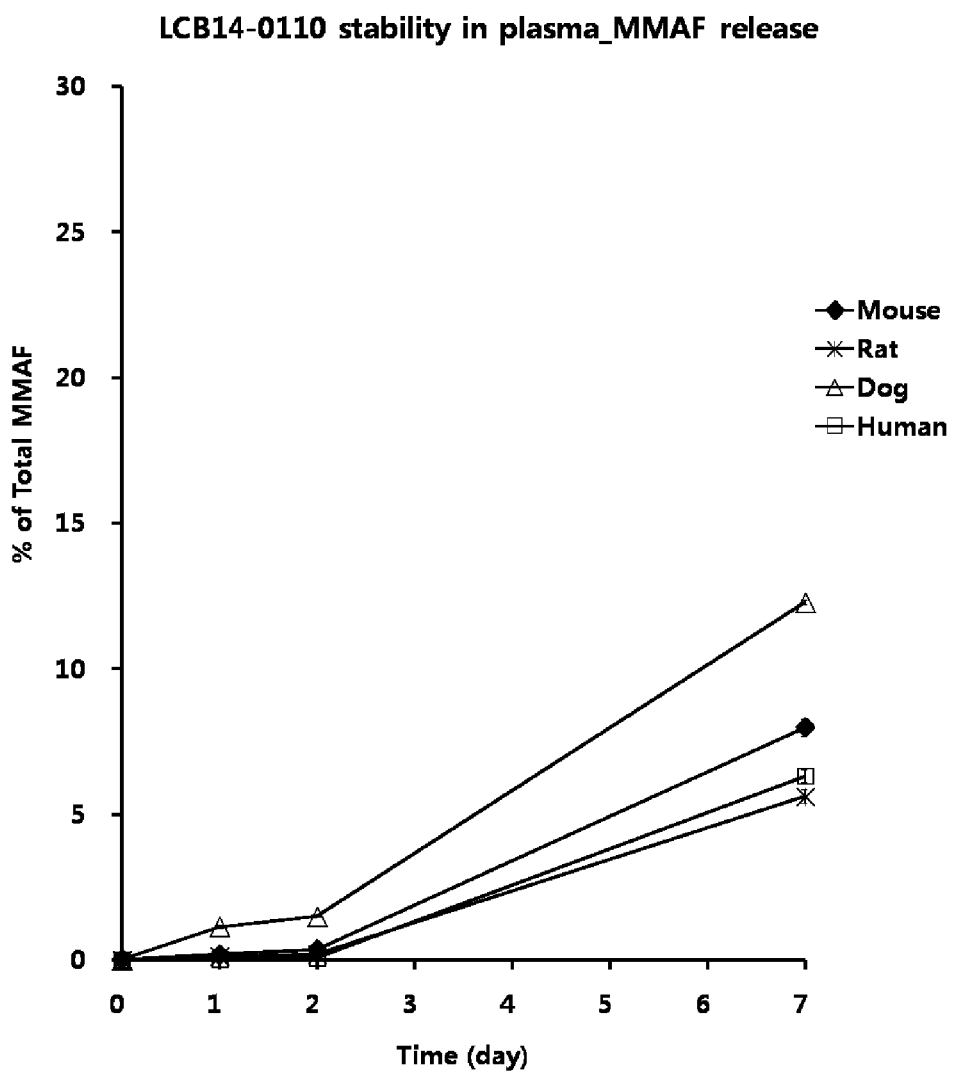

[FIG. 10]
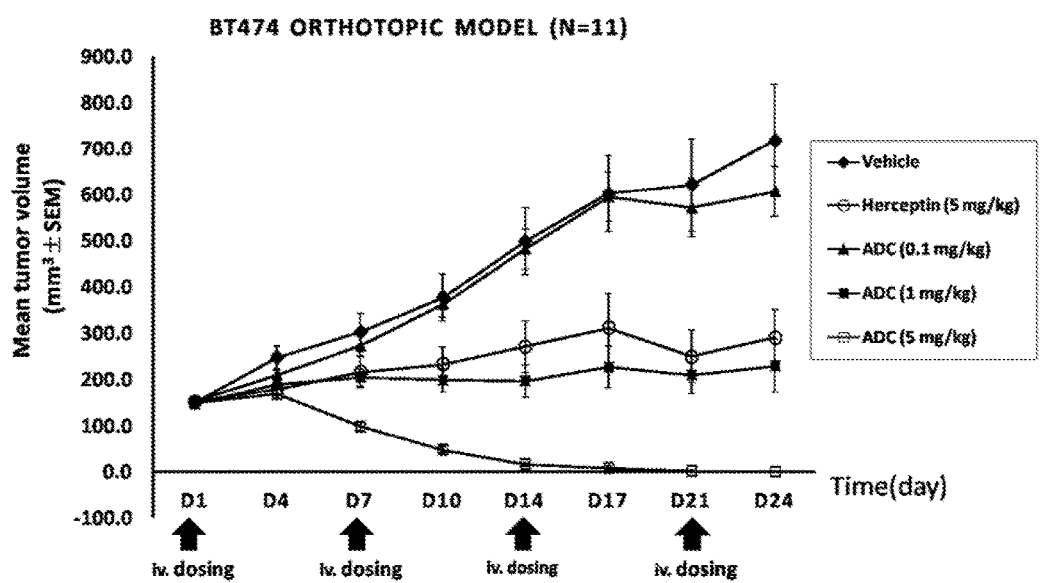

[FIG. 11]
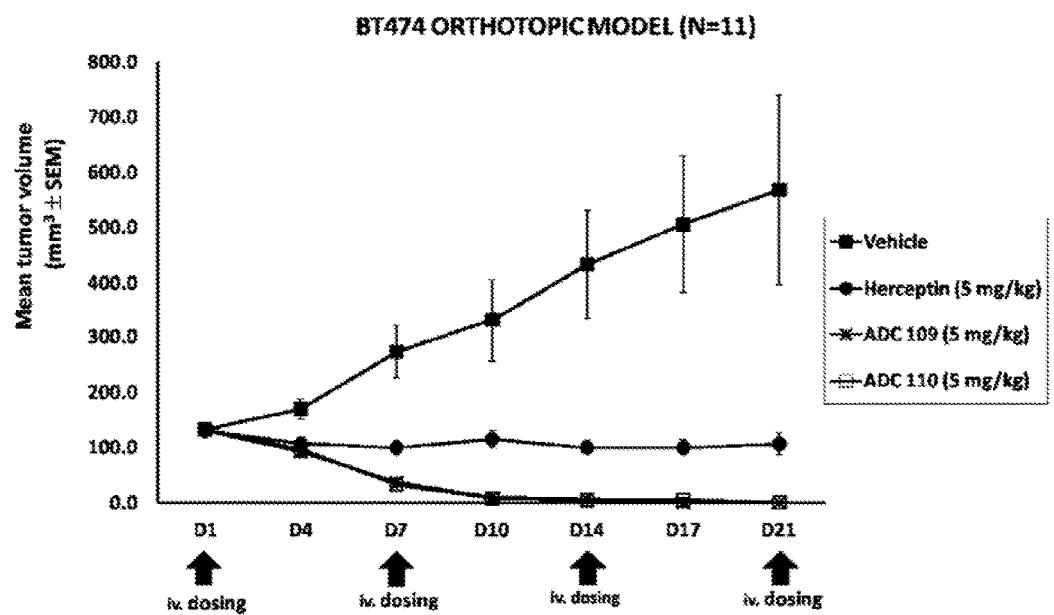

[FIG. 12]
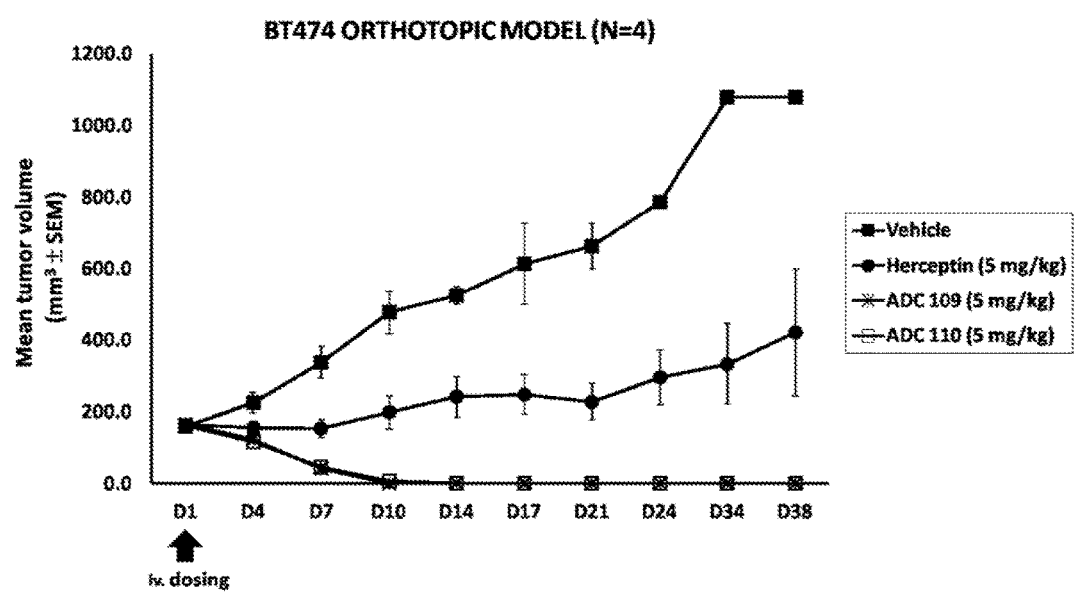

[FIG. 13]
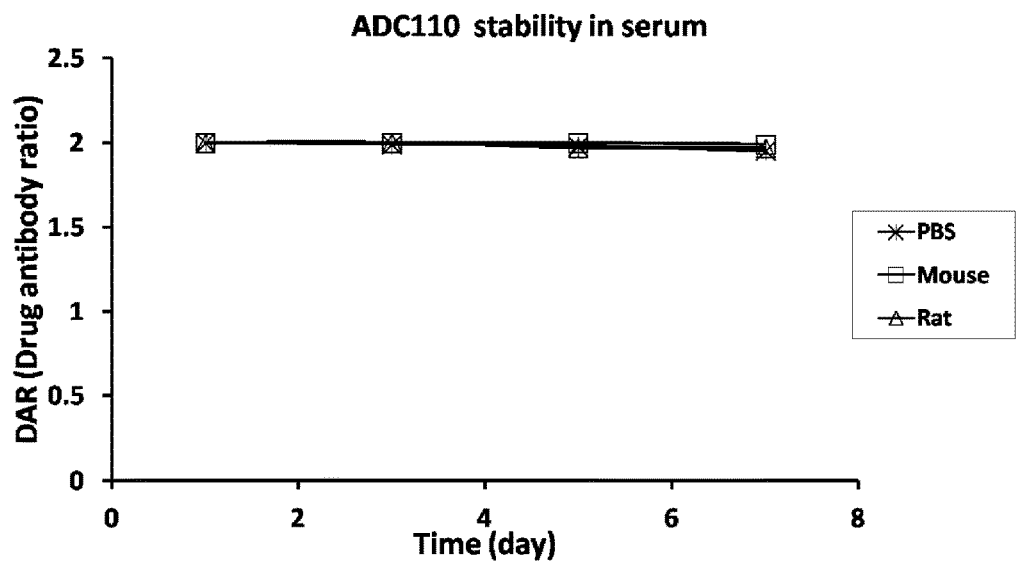
[FIG. 14]
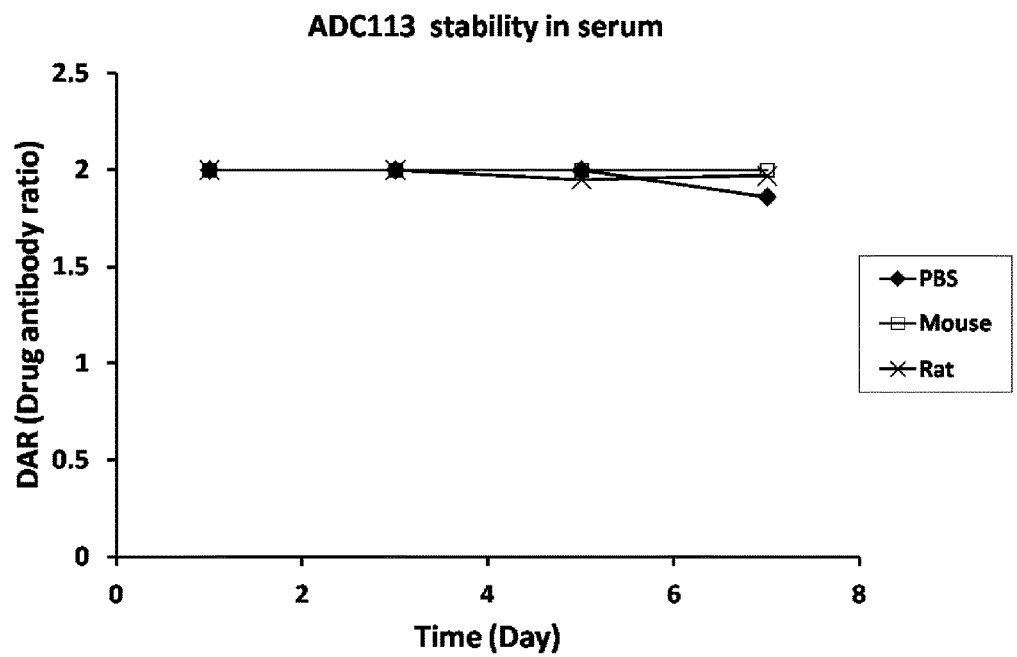

[FIG. 15]
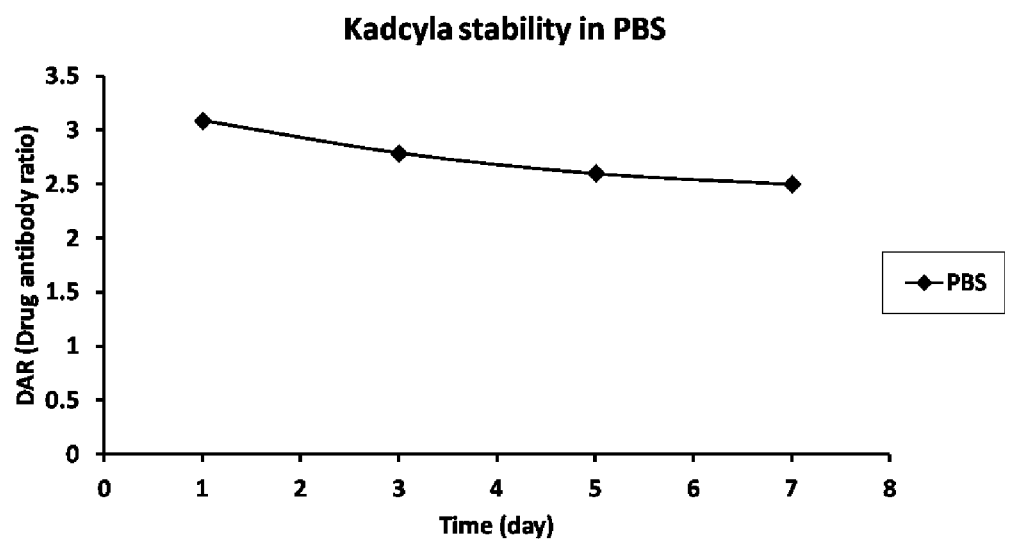

[FIG. 16]
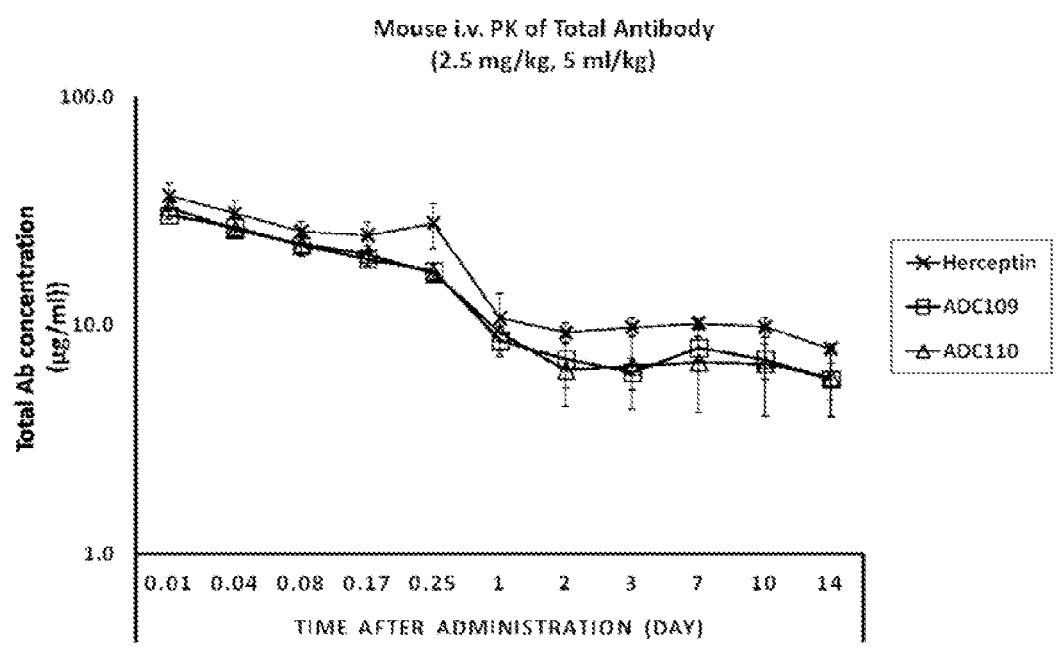

[FIG. 17]
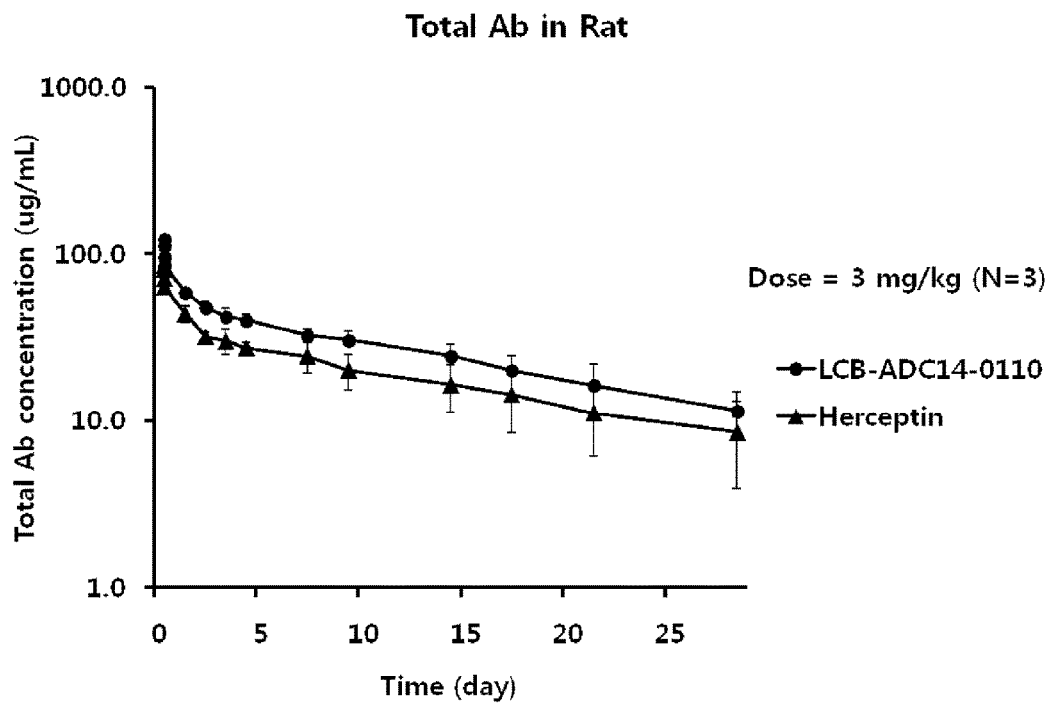
[FIG. 18]
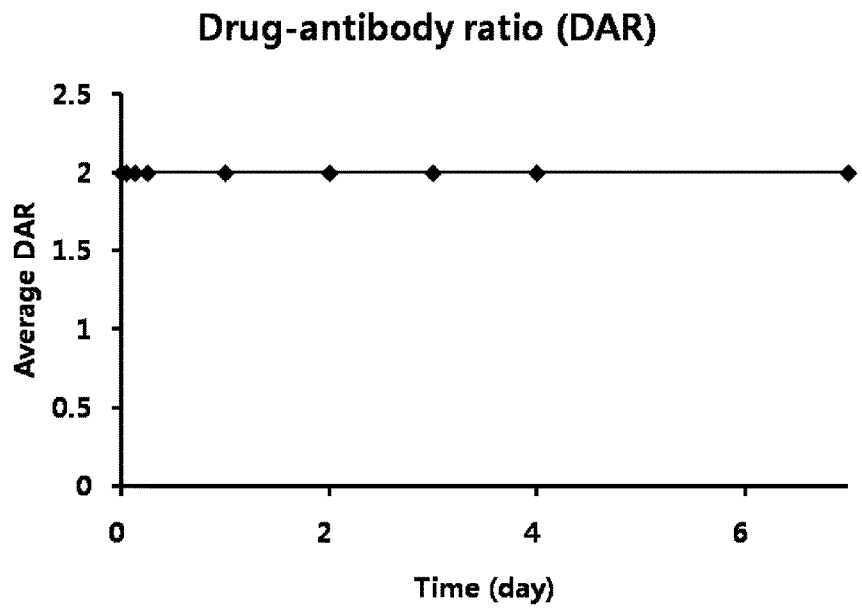

[FIG. 19]
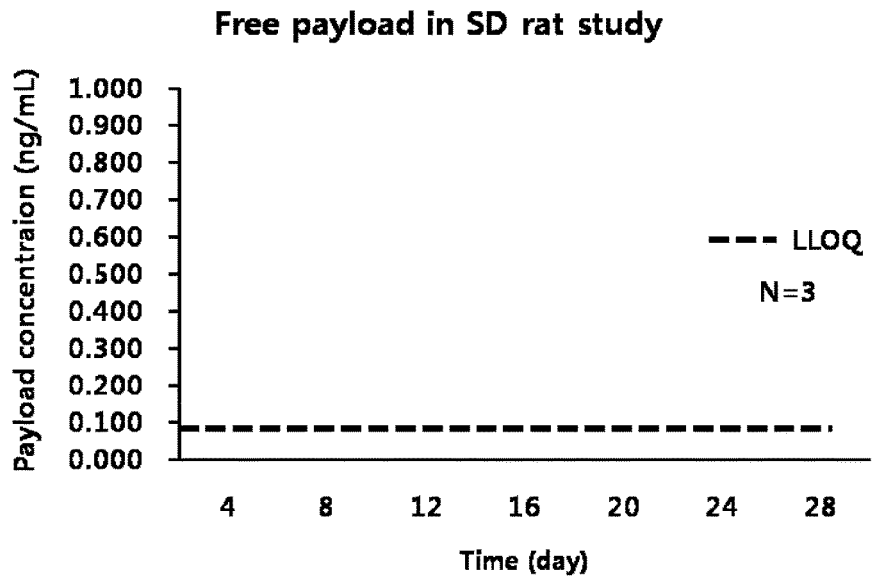
[FIG. 20]
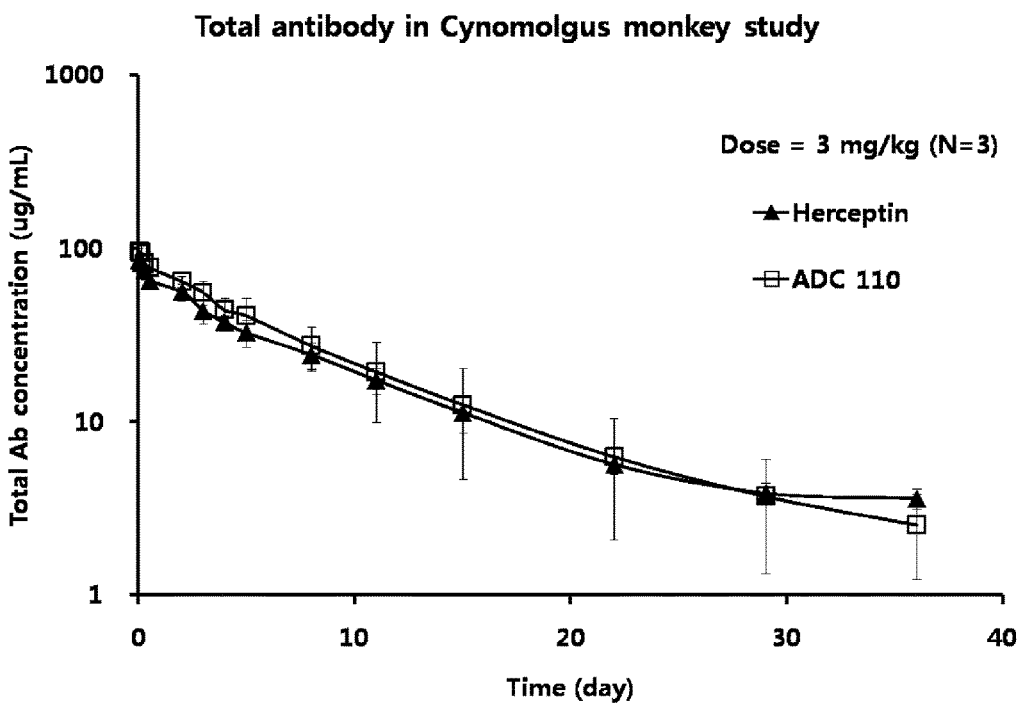

[FIG. 21]
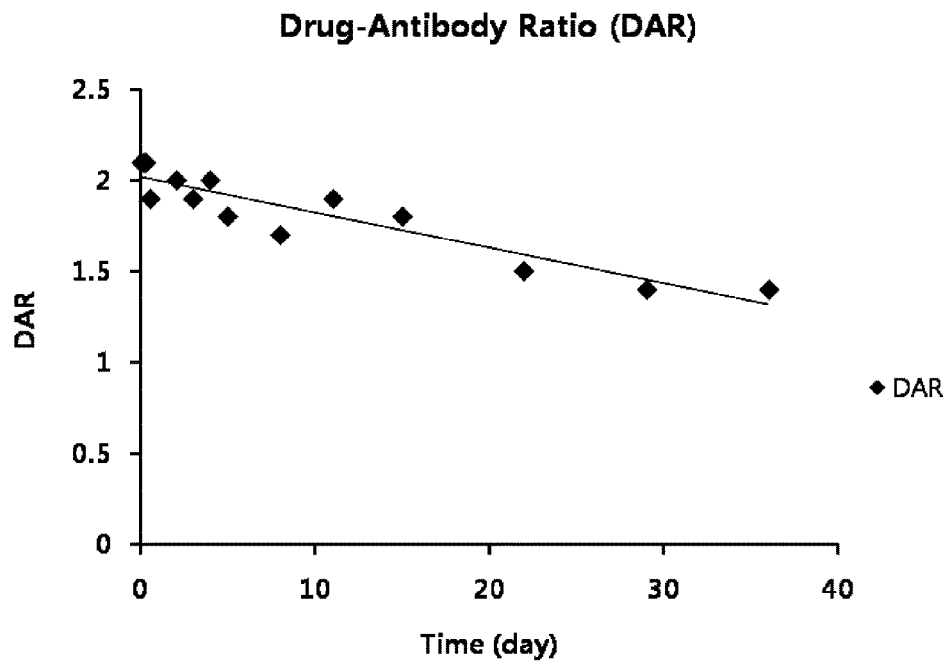
[FIG. 22]
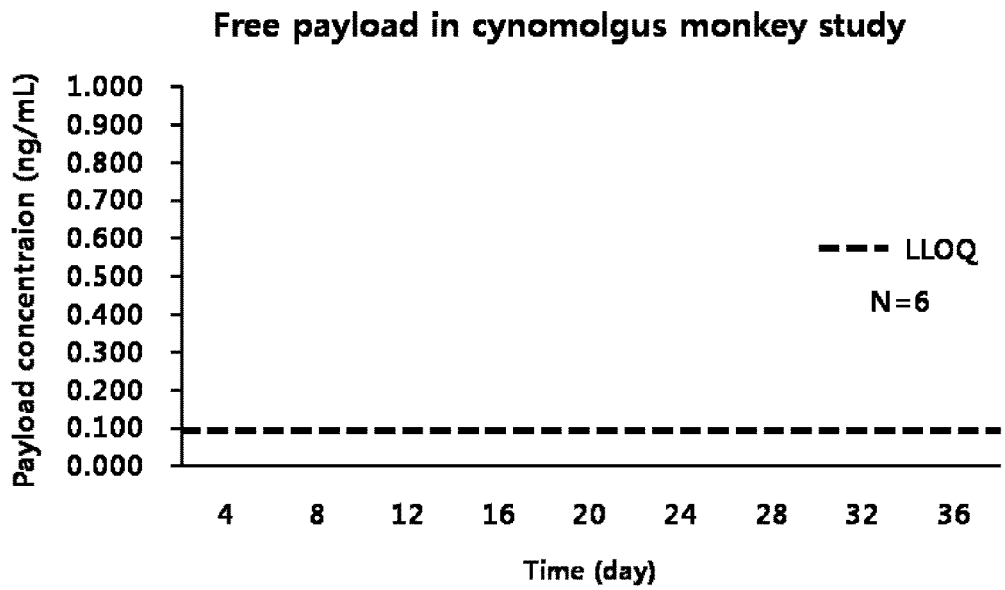

COMPOUNDS COMPRISING SELF-IMMOLATIVE GROUP

CROSS-REFERENCE TO RELATED APPLICATIONS

This application is a continuation of U.S. application Ser. No. 14/898,932, filed Dec. 16, 2015, now U.S. Pat. No. 9,993,568, which is a 371(c) National Stage Filing of PCT/KR15/005299, filed May 27, 2015, which claims the benefit of priority to Korean Republic Application No. 10-2015-0073161 filed May 26, 2015 and Korean Republic Application No. 10-2014-0064360 filed May 28, 2014. The entire contents of U.S. application Ser. No. 14/898,932 and PCT/KR15/005299 are incorporated herein in their entirety by reference.

TECHNICAL FIELD

The present invention relates to compounds comprising a self-immolative group, and the compounds comprising a self-immolative group according to the present invention may include a protein (for example, an oligopeptide, a polypeptide, an antibody, or the like) having substrate-specificity for a target and an active agent (for example, a drug, a toxin, a ligand, a detection probe, or the like) having a specific function or activity.

BACKGROUND ART

An antibody-drug conjugate (ADC) technology is a novel target-oriented technology for causing apoptosis of cancer cells by releasing a toxic material in the cells after binding a toxin to an antibody bound to an antigen. Since the ADC technology may allow a drug to be accurately delivered to target cancer cells and released only under a specific condition while minimizing an influence on healthy cells, the ADC technology may have more excellent efficacy than that of a therapeutic antibody itself, and significantly decrease the risk of an adverse reaction as compared to existing anticancer drugs.

A basic structure of the antibody-drug conjugates as described above is composed of an "antibody-linker-low molecular weight drug (toxin)". Here, the linker should allow the drug to exhibit a drug effect on target cancer cells while being easily separated by an antibody-drug dissociation phenomenon (for example, a result caused by hydrolysis by an enzyme) after the drug stably reaches to the target cells at the time of circulation and is introduced into the cells, in addition to playing a functional role of simply connecting the antibody and the drug. That is, since efficacy, systemic toxicity, and the like, of the antibody-drug conjugates depend on stability of the linker, the linker plays an important role in view of safety (Discovery Medicine 2010, 10(53): 329-39).

The linkers of the antibody-drug conjugates developed up to now are roughly classified into a non-cleavable type and a cleavable type.

As a non-cleavable linker, thioether is mainly used, and a drug is not dissociated due to separation of the linker in cells, but the drug is dissociated in a form in which the drug includes the linker and a single amino acid derived from an antibody. In the case of a mainly used thiol-maleimide bonding method, a reaction is easily carried out at pH of about 6 to 7, but a reverse reaction may also be easily chemically carried out, such that there is a problem in stability.

As a cleavable linker, a linker separated by a chemical method or a linker hydrolyzed by an enzyme reaction is mainly used. As a linker having a chemical separation mechanism, a linker containing a disulfide bond is representative. In addition, hydrazone or oxime linkers are also used.

A disulfide linker, which uses a phenomenon that a drug is dissociated using a thiol exchange reaction, uses the fact that a concentration of thiol (particularly, glutathione) in cells is higher than that in blood. However, since various types of thiols (for example, albumin, and glutathione) are present in the blood, a drug may be separated during circulation. In the case of a hydrazone linker, it is known that the hydrazone linker is relatively stable in the blood, but is unstable in cells, endosomes, or lysosomes, in which acidity is high, such that the hydrazone linker is rapidly hydrolyzed (Bioconjugate Chem. 2008, 19, 759-765; Bioconjugate Chem., 2010, 21, 5-13).

In order to solve the problem as described above, a linker hydrolyzed by an enzyme reaction in cells has been developed, and a peptide linker (for example, valine-citrulline) and a $\beta$-glucuronide linker belong thereto. Valine-citrulline and $\beta$-glucuronide are not directly connected to a drug but are bound to self-immolative groups, such that the drug is dissociated by a mechanism such as 1,6-elimination or cyclization mechanism after hydrolysis by an enzyme reaction, thereby exhibiting efficacy (Clinical Cancer Res., 2005, 11, 843-852).

It was reported that a valine-citrulline peptide linker is selectively decomposed by lysosome protease such as cathepsin B, and increases stability in the blood as compared to the hydrazone linker, which is chemically decomposed, and thus, an anti-cancer effect is increased (Bioconjugate Chem. 2008, 19, 1960-1963; J. Org. Chem., 2002, 67, 1866-1872). However, the peptide linker has hydrophobicity, such that there are disadvantages such as aggregation of prepared antibody-drug conjugates.

The $\beta$-glucuronide linker, which is recognized to thereby be hydrolyzed by $\beta$-glucuronidase, has high hydrophilicity unlike the peptide linker, such that at the time of binding the $\beta$-glucuronide linker to a drug having high hydrophobicity, solubility of antibody-drug conjugates may be increased. Examples of binding antibodies to various drugs (for example, monomethylauristatin F, monomethylauristatin E, doxorubicinpropyloxazoline (DPO)) using the $\beta$-glucuronide linker to prepare antibody-drug conjugates have been reported (Conjugation Chem., 2006, 17, 831-840; US2012/0107332). According to the report, the antibody-drug conjugates prepared using the glucuronide linker are significantly stable in rat plasma, but stability thereof in mouse plasma was not reported.

Therefore, the present invention is to develop an effective linker comprising a self-immolative group, capable of being more stable in the plasma, being stable in the circulation, and allowing a drug to be easily released in cancer cells to exhibit a drug effect.

DISCLOSURE

Technical Problem

An object of the present invention is to provide compounds comprising a self-immolative group.

Technical Solution

In one general aspect, compounds comprise a self-immolative group represented by the following Chemical Formula 1:

[Chemical Formula 1]

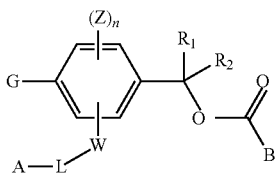

G is a glucuronic acid moiety or a derivative thereof;
A is $(C_1-C_{20})$hydrocarbyl, a biomaterial, or a modified biomaterial;
B is $(C_1-C_{100})$hydrocarbyl;
W is an electron withdrawing group;
Z is hydrogen, $(C_1-C_8)$alkyl, halogen, cyano, or nitro;
n is an integer of 1 to 3, and when n is an integer of 2 or more, each of the Z(s) are the same as or different from each other;
L is a linker connecting A and W of the self-immolative group by covalent bonds; and
$R_1$ and $R_2$ are each independently hydrogen, $(C_1-C_8)$alkyl, or $(C_3-C_8)$cycloalkyl.

G may be

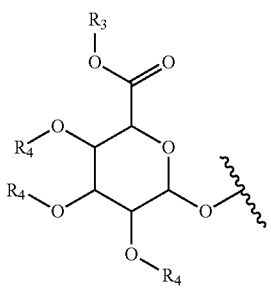

$R_3$ may be hydrogen or a carboxyl protecting group, and $R_4$(s) are each independently hydrogen or a hydroxyl protecting group.

W may be —C(O)—, —C(O)NR'—, —C(O)O—, —SO$_2$NR'—, —P(O)R''NR'—, —SONR'—, or —PO$_2$NR'—, and R' and R'' may be each independently hydrogen, $(C_1-C_8)$alkyl, $(C_3-C_8)$cycloalkyl, $(C_1-C_8)$alkoxy, $(C_1-C_8)$alkylthio, mono- or di-$(C_1-C_8)$alkylamino, $(C_3-C_{20})$heteroaryl or $(C_6-C_{20})$aryl.

The linker L may be alkylene having 1 to 50 carbon atoms and satisfy at least one of the following (i) to (iv):
(i) the alkylene includes at least one unsaturated bond,
(ii) the alkylene includes at least one heteroarylene,
(iii) the carbon atom of the alkylene is substituted with one or more hetero atoms selected from nitrogen (N), oxygen (O), and sulfur (S), and
(iv) the alkylene is further substituted with one or more alkyls having 1 to 20 carbon atoms.

The linker L may include at least one isoprenyl derivative unit represented by the following Chemical Formula A, which may be recognized by isoprenoid transferase.

[Chemical Formula A]

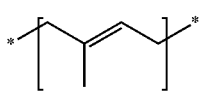

The linker L may further include a binding unit formed by 1,3-dipolar cycloaddition reactions, hetero-diels reactions, nucleophilic substitution reactions, non-aldol type carbonyl reactions, additions to carbon-carbon multiple bonds, oxidation reactions, or click reactions.

The binding unit may be formed by a reaction between acetylene and azide, or a reaction between an aldehyde or ketone group and hydrazine or hydroxylamine.

The binding unit may be represented by the following Chemical Formula B, C, D, or E:

[Chemical Formula B]

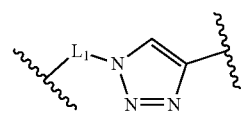

[Chemical Formula C]

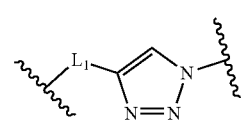

[Chemical Formula D]

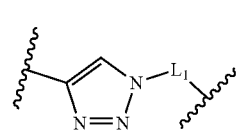

[Chemical Formula E]

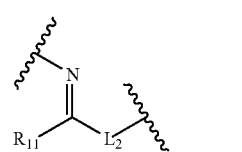

$L_1$ is a single bond or alkylene having 1 to 30 carbon atoms;
$R_{11}$ is hydrogen or alkyl having 1 to 10 carbon atoms; and
$L_2$ is alkylene having 1 to 30 carbon atoms.

The linker L may further include a connection unit represented by the following Chemical Formula F or G:

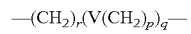   [Chemical Formula F]

   [Chemical Formula G]

V is a single bond, —O—, —S—, —NR$_{21}$—, —C(O)NR$_{22}$—, —NR$_{23}$C(O)—, —NR$_{24}$SO$_2$—, or —SO$_2$NR$_{25}$—;
X is —O—, $(C_1-C_8)$alkylene, or —NR$_{21}$—;
$R_{21}$ to $R_{25}$ are each independently hydrogen, $(C_1-C_6)$alkyl, $(C_1-C_6)$alkyl$(C_6-C_{20})$aryl, or $(C_1-C_6)$alkyl$(C_3-C_{20})$heteroaryl;
r is an integer of 1 to 10;
p is an integer of 0 to 10;
q is an integer of 1 to 10; and
w is an integer of 1 to 10.

When A is hydrocarbyl having 1 to 20 carbon atoms, L may be

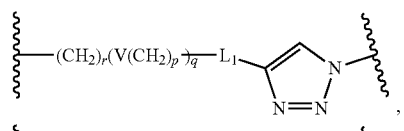

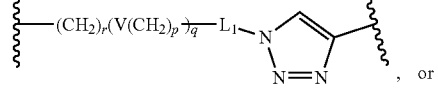

, or

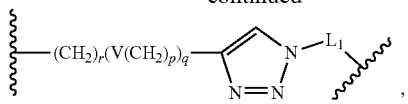

V may be a single bond, —O—, —S—, —NR$_{21}$—, —C(O)NR$_{22}$—, —NR$_{23}$C(O)—, —NR$_{24}$SO$_2$—, or —SO$_2$NR$_{25}$—, R$_{21}$ to R$_{25}$ may be each independently hydrogen, (C$_1$-C$_6$)alkyl, (C$_1$-C$_6$)alkyl(C$_6$-C$_{20}$)aryl, or (C$_1$-C$_6$)alkyl(C$_3$-C$_{20}$)heteroaryl, r may be an integer of 1 to 10, p may be an integer of 0 to 10, q may be an integer of 1 to 10, and L$_1$ may be a single bond.

The biomaterial may be a protein.

The protein may be an oligopeptide, a polypeptide, an antibody, a fragment of an antigenic polypeptide, or a repebody.

The protein may have an amino acid motif capable of being recognized by isoprenoid transferase.

The protein may further include a spacer unit composed of an amino acid, an oligopeptide, or a polypeptide between the protein and the amino acid motif.

The protein may be covalently bonded to the linker L through the amino acid motif.

The amino acid motif may be covalently bonded to a C-terminal of the protein, or covalently bonded to at least one spacer unit covalently bonded to the C-terminal of the protein.

The C-terminal of the protein may be a C-terminal of a light chain or heavy chain of the antibody.

The isoprenoid transferase may be farnesyl protein transferase (FTase) or geranylgeranyl transferase (GGTase).

The antibody may be selected from the group consisting of intact polyclonal antibodies, intact monoclonal antibodies, antibody fragments, single chain Fv (scFv) mutants, multispecific antibodies, bispecific antibodies, chimeric antibodies, humanized antibodies, human antibodies, fusion proteins including an antigen determination portion of an antibody, and other modified immunoglobulin molecules including an antigen recognition site.

The antibody may be selected from the group consisting of muromonab-CD3 abciximab, rituximab, daclizumab, palivizumab, infliximab, trastuzumab, (referred to as 'Herceptin'), etanercept, basiliximab, gemtuzumab ozogamicin, alemtuzumab, ibritumomab tiuxetan, adalimumab, alefacept, omalizumab, efalizumab, tositumomob-I[131], cetuximab, bevacizumab, natalizumab, ranibizumab, panitumumab, eculizumab, rilonacept, certolizumab pegol, romiplostim, AMG-531, CNTO-148, CNTO-1275, ABT-874, LEA-29Y, belimumab, TACI-Ig, second generation anti-CD20, ACZ-885, tocilizumab, atlizumab, mepolizumab, pertuzumab, HuMax CD20, tremelimumab (CP-675 206), ticilimumab, MDX-010, IDEC-114, inotuzumab ozogamycin, HuMax EGFR, aflibercept, VEGF Trap-Eye, HuMax-CD4, Ala-Ala, ChAglyCD3, TRX4, catumaxomab, IGN101, MT-201, pregovomab, CH-14.18, WX-G250, AMG-162, AAB-001, motavizumab, MEDI-524, efumgumab, Aurograb®, raxibacumab, third generation anti-CD20, LY2469298, and veltuzumab.

The protein may be a monoclonal antibody.

The amino acid motif may be CYYX, XXCC, XCXC, or CXX, wherein C represents cysteine, Y represents an aliphatic amino acid, and X represents an amino acid that determines a substrate specificity of the isoprenoid transferase.

B may be active agent.

The active agent may be a drug, a toxin, an affinity ligand, a detection probe, or a combination thereof.

The active agent may be an immunomodulatory compound, an anticancer agent, an antiviral agent, an antibacterial agent, an antifungal agent, an antiparasitic agent, or a combination thereof.

The protein having an amino acid motif may be selected from the group consisting of A-HC-(G)$_z$CVIM, A-HC-(G)$_z$CVLL, A-LC-(G)$_z$CVIM, and A-LC-(G)$_z$CVLL, wherein A represents the antibody, HC represents a heavy chain, LC represents a light chain, G represents a glycine unit, and z is an integer of 0 to 20.

The compounds may be selected from compounds having the following structures:

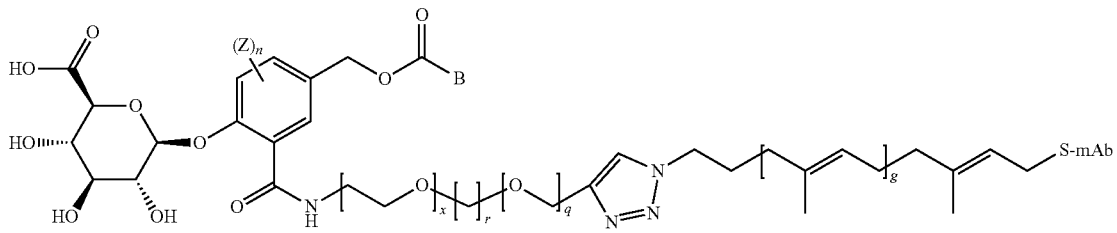

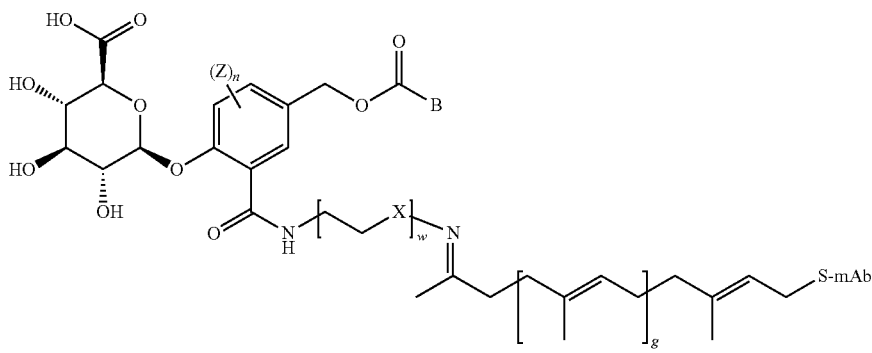

here,
Z is hydrogen, $(C_1-C_8)$alkyl, halogen, cyano, or nitro;
X is —O—, $(C_1-C_8)$alkylene, or —$NR_{21}$—;
$R_{21}$ is hydrogen, $(C_1-C_6)$alkyl, $(C_1-C_6)$alkyl$(C_6-C_{20})$aryl, or $(C_1-C_6)$alkyl$(C_3-C_{20})$heteroaryl;
n is an integer of 1 to 3, and when n is an integer of 2 or more, each of the Z(s) are the same as or different from each other;
r is an integer of 1 to 10;
q is an integer of 1 to 10;
w is an integer of 1 to 10.
x is an integer of 0 to 10;
g is an integer of 1 to 10;
—S-mAb is A-HC-$(G)_z$CVIM-, A-HC-$(G)_z$CVLL-, A-LC-$(G)_z$CVIM-, or A-LC-$(G)_z$CVLL-, wherein A represents the antibody, HC represents a heavy chain, LC represents a light chain, G represents a glycine unit, and z is an integer of 0 to 20;
B is a drug having a structure selected from the following structures; and

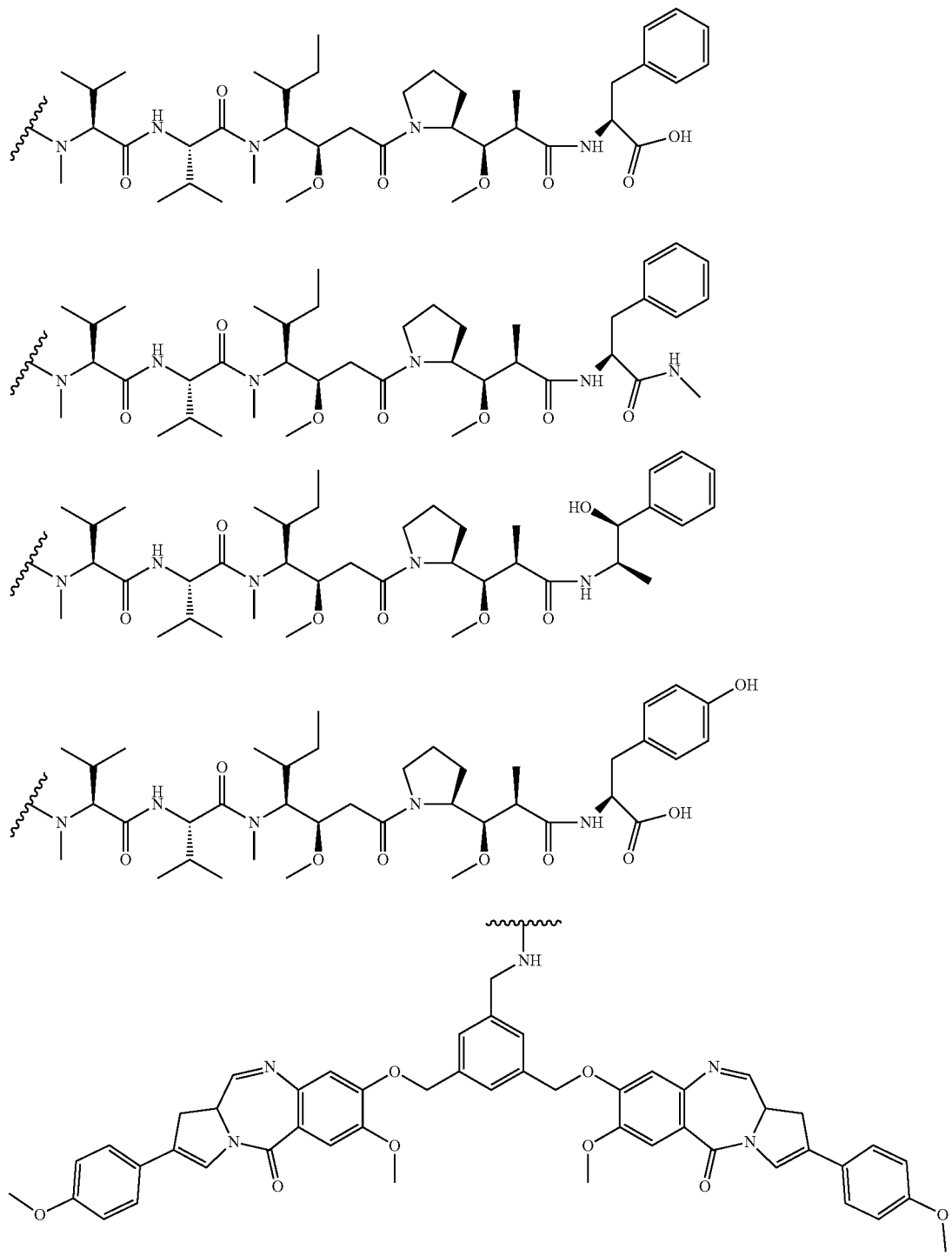

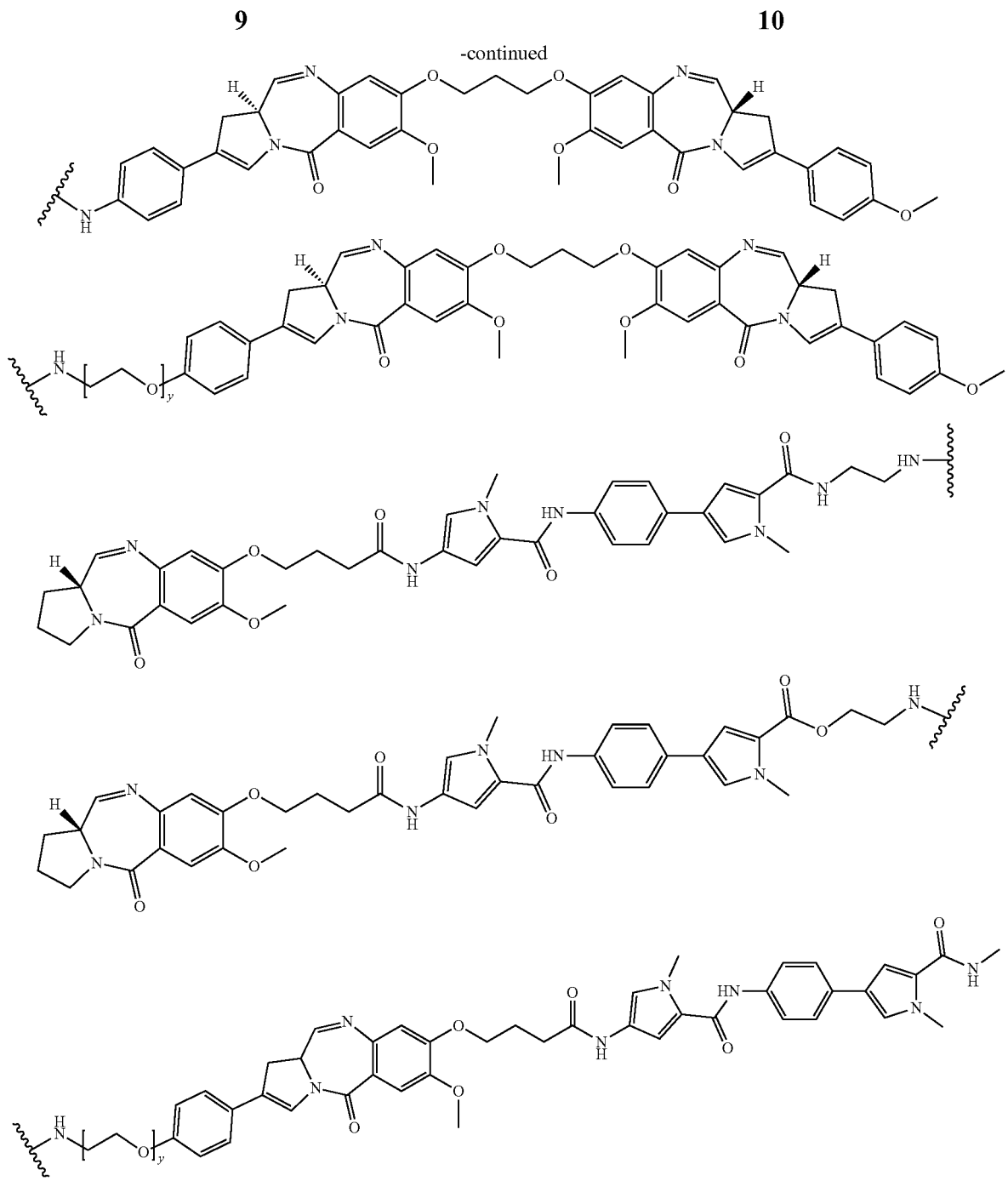

y is an integer of 1 to 10.

Advantageous Effects

Compounds comprising a self-immolative group according to the present invention may include a protein (for example, an oligopeptide, a polypeptide, an antibody, or the like) having substrate-specificity for a target and an active agent (for example, a drug, a toxin, a ligand, a detection probe, or the like) having a specific function or activity. The self-immolative group may be more stable in blood, plasma, and the like, as compared to the existing linker while specifically binding to a protein over-expressed in cells causing a disease, but may be separated in target cancer cells, such that the active agent may specifically act on the cells causing the disease, thereby making it possible to use the compounds to treat diseases.

DESCRIPTION OF DRAWINGS

FIG. 1 illustrates an active drug release mechanism from β-glucuronide based linker.

FIG. 2 illustrates a result obtained by measuring a hydrolysis rate by β-glucuronidase in Experimental Example 1.

FIG. 3 illustrates a result obtained by measuring plasma stability in Experimental Example 2.

FIG. 4 illustrates a result obtained by measuring plasma stability of LCB14-0648 prepared in Example 5.

FIG. 5 illustrates a result obtained by measuring plasma stability of LCB14-0663 prepared in Example 6.

FIG. 6 illustrates a result obtained by measuring plasma stability of LCB14-0664 prepared in Example 7.

FIG. 7 is a schematic view illustrating reactions in Example 9.

FIG. 8 illustrates a result obtained by measuring mouse plasma stability of ADC (LCB14-0109) prepared in Example 8.

FIG. 9 illustrates a result obtained by variously measuring plasma stability of ADC (LCB14-0110) prepared in Example 9.

FIG. 10 is a graph illustrating a result obtained by observing a tumor volume depending on QW dose in Experimental Example 6 (Vehicle, Herceptin (5 mg/kg), and ADC109 (0.1, 1, 5 mg/kg)).

FIG. 11 is a graph illustrating a result obtained by observing a drug effect depending on repetitive administration in Experimental Example 6 (Vehicle, Herceptin (5 mg/kg), ADC109 (5 mg/kg), and ADC110 (5 mg/kg)).

FIG. 12 is a graph illustrating a result obtained by observing a drug effect depending on single-dose administration in Experimental Example 6 (Vehicle, Herceptin (5 mg/kg), ADC109 (5 mg/kg), and ADC110 (5 mg/kg)).

FIG. 13 illustrates a result obtained by evaluating in vitro plasma stability of ADC 110 (Example 10) in Experimental Example 7.

FIG. 14 illustrates a result obtained by evaluating in vitro plasma stability of ADC 113 (Example 11) in Experimental Example 7.

FIG. 15 illustrates a result obtained by evaluating in vitro plasma stability of Kadcyla in Experimental Example 7.

FIG. 16 is a graph illustrating a result obtained by observing in vivo PK profile in a mouse, in Experimental Example 8.

FIG. 17 is a graph illustrating a result obtained by observing in vivo PK profile of ADC 110 (Example 10) in a rat in Experimental Example 8.

FIG. 18 is a graph illustrating a result obtained by observing an in vivo drug-antibody ratio (DAR) of ADC 110 (Example 10) in a rat in Experimental Example 8.

FIG. 19 is a graph illustrating a result obtained by observing an in vivo free payload concentration of ADC 110 (Example 10) in a rat in Experimental Example 8.

FIG. 20 is a graph illustrating a result obtained by observing in vivo PK profile of ADC 110 (Example 10) in a monkey in Experimental Example 8.

FIG. 21 is a graph illustrating a result obtained by observing in vivo drug-antibody ratio (DAR) of ADC 110 (Example 10) in a monkey in Experimental Example 8.

FIG. 22 is a graph illustrating a result obtained by observing an in vivo free payload concentration of ADC 110 (Example 10) in a monkey in Experimental Example 8.

BEST MODE

The present invention relates to compounds comprising a self-immolative group. In detail, the compounds comprising a self-immolative group according to the present invention may be represented by the following Chemical Formula 1 and include a protein (for example, an oligopeptide, a polypeptide, an antibody, or the like) having substrate-specificity for a target and an active agent (for example, a drug, a toxin, a ligand, a detection probe, or the like) having a specific function or activity.

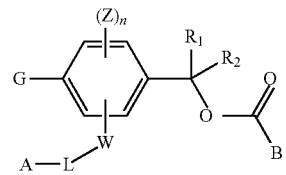

[Chemical Formula 1]

G is a glucuronic acid moiety or a derivative thereof;

A is $(C_1-C_{20})$hydrocarbyl, a biomaterial, or a modified biomaterial;

B is $(C_1-C_{100})$ hydrocarbyl;

W is an electron withdrawing group;

Z is hydrogen, $(C_1-C_8)$alkyl, halogen, cyano, or nitro;

n is an integer of 1 to 3, and when n is an integer of 2 or more, each of the Z(s) are the same as or different from each other;

L is a linker connecting A and W of the self-immolative group by covalent bonds; and $R_1$ and $R_2$ are each independently hydrogen, $(C_1-C_8)$alkyl, or $(C_3-C_8)$cycloalkyl.

In the compounds comprising a self-immolative group according to the present invention, the self-immolative group may be bound to glucuronide capable of being separated by β-glucuronidase, G, which is the glucuronide group or the derivative thereof capable of being separated by β-glucuronidase, may be represented by the following structure.

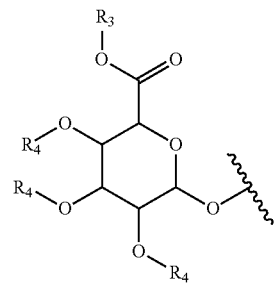

($R_3$ is hydrogen or a carboxyl protecting group, and $R_4$(s) are each independently hydrogen or a hydroxyl protecting group.)

The carboxyl protecting group, which is a general protecting group capable of being used in organic synthesis, may be preferably methyl, methoxymethyl, methylthiomethyl, tetrahydropyranyl, benzyloxymethyl, phenacyl, N-phthalimidomethyl, 2,2,2-trichloroethyl, 2-haloethyl, 2-(p-toluenesulfonyl)ethyl, t-butyl, cinnamyl, benzyl, triphenylmethyl, bis(o-nitrophenyl)methyl, 9-anthramethyl, 2-(9,10-dioxo)anthrylmethyl, piperonyl, trimethylsilyl, t-butyldimethylsilyl, or S-t-butyl, 2-alkyl-1,3-oxazolinyl, but is not limited thereto. Further, the hydroxyl protecting group, which is a general protecting group capable of being used in organic synthesis, may be preferably acetyl, methyl, ethoxyethyl, benzoyl, benzyl, 4-methoxybenzyl, 3,4-dimethoxybenzyl, tetrahydropyranyl (THP), tetrahydrofuran (THF), tert-butyldimethylsilyl (TBDMS), trimethylsilyl (TMS), triethylsilyl (TES), triisopropylsilyl (TIP), tert-butyldiphenylsilyl (TBDPS), tri-iso-propylsilyloxymethyl (TOM), β-methoxyethoxymethyl (MEM), methoxymethyl (MOM), allyl, or trityl, but is not limited thereto.

In the compounds comprising a self-immolative group according to the present invention, W, which is the electron withdrawing group, may be preferably —C(O)—, —C(O)

NR'—, —C(O)O—, —SO₂NR'—, —P(O)R"NR'—, —SONR'—, or —PO₂NR'—, but is not limited thereto, and R' and R" may be each independently hydrogen, $(C_1\text{-}C_8)$ alkyl, $(C_3\text{-}C_8)$cycloalkyl, $(C_1\text{-}C_8)$alkoxy, $(C_1\text{-}C_8)$alkylthio, mono- or di-$(C_1\text{-}C_8)$alkylamino, $(C_3\text{-}C_{20})$heteroaryl or $(C_6\text{-}C_{20})$aryl.

In the compounds comprising a self-immolative group according to the present invention, the linker L may be alkylene having 1 to 50 carbon atoms and satisfy at least one, preferably, at least two of the following (i) to (iv):

(i) the alkylene includes at least one unsaturated bond,
(ii) the alkylene includes at least one heteroarylene,
(iii) a carbon atom of the alkylene is substituted by one or more hetero atoms selected from nitrogen (N), oxygen (O), and sulfur (S), and
(iv) the alkylene is further substituted with one or more alkyls having 1 to 20 carbon atoms.

In the compounds comprising a self-immolative group according to the present invention, the linker L may include at least one isoprenyl derivative unit represented by the following Chemical Formula A, which may be recognized by isoprenoid transferase.

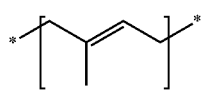

[Chemical Formula A]

In addition, the linker L may further include a binding unit formed by 1,3-dipolar cycloaddition reactions, hetero-Diels Alder reactions, nucleophilic substitution reactions, non-aldol type carbonyl reactions, additions to carbon-carbon multiple bonds, oxidation reactions, or click reactions. The binding unit, which is formed by a reaction between acetylene and azide, or a reaction between an aldehyde or ketone group and hydrazine or hydroxylamine, may be preferably represented by the following Chemical Formula B, C, D, or E.

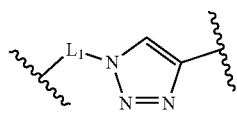

[Chemical Formula B]

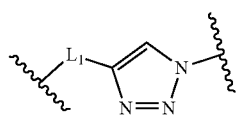

[Chemical Formula C]

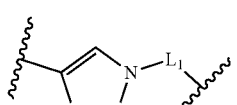

[Chemical Formula D]

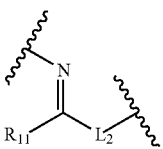

[Chemical Formula E]

$L_1$ is a single bond or alkylene having 1 to 30 carbon atoms;
$R_{11}$ is hydrogen or alkyl having 1 to 10 carbon atoms; and
$L_2$ is alkylene having 1 to 30 carbon atoms.

Click chemistry reactions are carried out in a mild condition, thereby making it possible to easily handle proteins. The click chemistry reaction shows significantly high reaction specificity. Therefore, even though a protein has other functional groups (for example, a side chain residue, or at a C- or N-terminal), these functional groups are not affected by the click chemistry reaction. For example, a click chemistry reaction between an azide group and an acetylene group of a protein may occur while other functional groups of the protein are not affected by the click chemistry reaction. Further, the click chemistry reaction may specifically occur regardless of the kind of involved ligand. In some cases, the ligand may be selected so as to improve overall reaction efficiency. For example, an azide-acetylene click chemistry reaction may produce triazole with a high yield (ref: Rhiannon K. Hia et al, Chem. Rev. 2009, 109, 5620; Morten Meldal and Christian Wenzel Tornoe, Chem Rev., 2008, 108, 2952; Hartmuth C. Kolb et al, Angew. Chemie Int. Ed. Engl., 2001, 40, 2004, which are all incorporated herein by reference).

The azide and acetylene groups are functional groups that do not exist in amino acid sequences of natural proteins. In the case in which a conjugation reaction occurs using these functional groups, none of the side chain residues and none of the N-terminal or C-terminal functional groups are affected by the click chemistry reaction.

Further, the linker L may further include a connection unit represented by Chemical Formula F or G:

—(CH₂)$_r$(V(CH₂)$_p$)$_q$—     [Chemical Formula F]

—(CH₂CH₂X)$_w$—     [Chemical Formula G]

V is a single bond, —O—, —S—, —NR₂₁—, —C(O)NR₂₂—, —NR₂₃C(O)—, —NR₂₄SO₂—, or —SO₂NR₂₅—;
X is —O—, $(C_1\text{-}C_8)$alkylene, or —NR₂₁—;
$R_{21}$ to $R_{25}$ are each independently hydrogen, $(C_1\text{-}C_6)$alkyl, $(C_1\text{-}C_6)$alkyl$(C_6\text{-}C_{20})$aryl, or $(C_1\text{-}C_6)$alkyl$(C_3\text{-}C_{20})$heteroaryl;
r is an integer of 1 to 10;
p is an integer of 0 to 10;
q is an integer of 1 to 10; and
w is an integer of 1 to 10.

More preferably, the linker L may all include at least one isoprenyl derivative unit represented by Chemical Formula A, the binding unit represented by Chemical Formula B, C, D, or E, and the connection unit represented by Chemical Formula F or G.

More preferably, the linker L may be represented by the following structures.

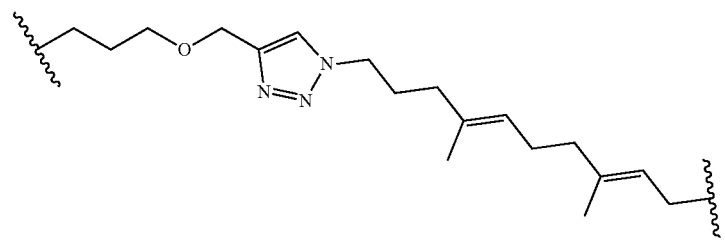

-continued

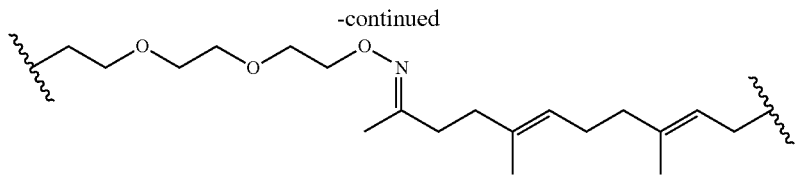

In the compounds comprising a self-immolative group according to the present invention, when A is hydrocarbyl having 1 to 20 carbon atoms, L may be

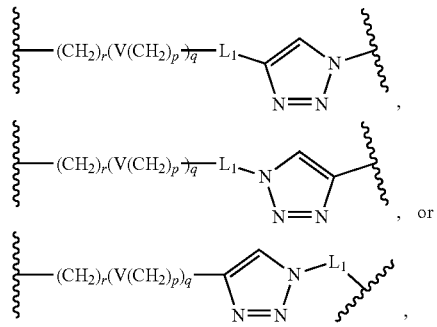

V may be a single bond, —O—, —S—, —NR$_{21}$—, —C(O)NR$_{22}$—, —NR$_{23}$C(O)—, —NR$_{24}$SO$_2$—, or —SO$_2$NR$_{25}$—, R$_{21}$ to R$_{25}$ may be each independently hydrogen, (C$_1$-C$_6$)alkyl, (C$_1$-C$_6$)alkyl(C$_6$-C$_{20}$)aryl, or (C$_1$-C$_6$)alkyl(C$_3$-C$_{20}$)heteroaryl, r may be an integer of 1 to 10, p may be an integer of 0 to 10, q may be an integer of 1 to 10, and L$_1$ may be a single bond.

In the compounds comprising a self-immolative group according to the present invention, the biomaterial may be a protein, wherein the protein includes an oligopeptide, a polypeptide, an antibody, a fragment of an antigenic polypeptide, and a repebody.

The protein has an amino acid motif capable of being recognized by isoprenoid transferase. That is, a C-terminal (fragment, an analog or derivative thereof) of the protein may be bound to the amino acid motif capable of being recognized by isoprenoid transferase. In addition, the protein may further include a spacer unit composed of an amino acid, an oligopeptide, or a polypeptide between the protein and the amino acid motif. The protein has a deletion at the carboxyl (C) terminal of the protein or an addition by a covalent bond of the spacer unit at the carboxyl terminal of the protein. The protein may be directly covalently bound to the amino acid motif or be covalently bound to the spacer unit to thereby be connected to the amino acid motif. The amino acid spacer unit is composed of 1 to 20 amino acids, among them, a glycine unit is preferable.

The protein has an amino acid motif capable of being recognized by isoprenoid transferase. That is, a C-terminal (fragment, an analog or derivative thereof) of the protein may be bound to the amino acid motif capable of being recognized by isoprenoid transferase. In addition, the protein may further include a spacer unit composed of an amino acid, an oligopeptide, or a polypeptide between the protein and the amino acid motif. The protein has a deletion at the carboxyl (C) terminal of the protein or an addition by a covalent bond of the spacer unit at the carboxyl terminal of the protein. The protein may be directly covalently bound to the amino acid motif or be covalently bound to the spacer unit to thereby be connected to the amino acid motif. The amino acid spacer unit is composed of 1 to 20 amino acids, among them, a glycine unit is preferable.

Examples of isoprenoid transferase may include farnesyl protein transferase (FTase) or geranylgeranyl transferase (GGTase), which involve the transfer of a farnesyl or a geranyl-geranyl residue to C-terminal cysteine(s) of a target protein, respectively. GGTase may be classified into GGTase I and GGTase II. FTase and GGTase I may recognize a CAAX motif, and GGTase II may recognize a XXCC, XCXC, or CXX motif (here, C represents cysteine, A represents an aliphatic amino acid, and X represents an amino acid determining the substrate specificity of the isoprenoid transferases) (ref: Nature Rev. Cancer 2005, 5(5), pp. 405-12; Nature Chemical Biology, 2010, 17, pp. 498-506; Lane K T, Bees L S, Structural Biology of Protein of Farnesyltransferase and Geranylgeranyl transferase Type I, Journal of Lipid Research, 47, pp. 681-699 (2006); Patrick J. Kasey, Miguel C. Seabra; Protein Prenyl transferases, The Journal of Biological Chemistry, Vol. 271, No. 10, Issue of March 8, pp. 5289-5292 (1996), the contents of these references are incorporated by reference in their entirety).

In the present invention, isoprenoid transferases from a variety of sources, for example, humans, animals, plants, bacteria, virus, and the like, may be used. In some embodiments, naturally occurring isoprenoid transferases can be used. In some other embodiments, naturally or artificially modified isoprenoid transferases may be used. For example, there is an isoprenoid transferase having at least one amino acid sequence naturally changed (including post-translational modification), a naturally or artificially truncated form of a naturally occurring isoprenoid transferase, and an isoprenoid transferase modified by at least one of (His)-tag, GST, GFP, MBP, CBP, Iospeptag, BCCP, Myc-tag, Calmodulin-tag, FLAG-tag, HA-tag, Maltose binding protein-tag, Nus-tag, Glutathione-S-transferase-tag, Green fluorescent protein-tag, Thioredoxin-tag, S-tag, Softag 1, Softag 3, Strep-tag, SBP-tag, Ty-tag, and the like.

Isoprenoid transferases may recognize an isosubstrate as well as a substrate. The isosubstrate refers to a substrate analog which has a modification in the substrate. Isoprenoid transferases alkylate a specific amino acid motif (for example, CAAX motif) at the C-terminal of a protein (Ref: Benjamin P. Duckworth et al, ChemBioChem 2007, 8, 98; Uyen T. T. Nguyen et al, ChemBioChem 2007, 8, 408; Guillermo R. Labadie et al, J. Org. Chem. 2007, 72(24), 9291; James W. Wollack et al, ChemBioChem 2009, 10, 2934, the contents of these references are incorporated by reference). A functionalized protein may be produced using an isoprenoid transferase and an isosubstrate through alkylation at a C-terminal cysteine(s).

For example, the cysteine residue of a C-terminal CAAX motif may be reacted with an isosubstrate using an isoprenoid transferase. In certain cases, AAX may be then removed by a protease. The obtained cysteine may then be methylated at the carboxyl terminal by an enzyme (ref: Iran M. Bell, J. Med. Chem. 2004, 47(8), 1869, which is incorporated herein by reference).

The proteins of the present invention may be prepared using any molecular biological method or cell biological method well known in the art. For example, transient transfection methods may be used. Genetic sequences encoding a specific amino acid motif capable of being recognized by an isoprenoid transferase may be inserted into a known plasmid vector using standard PCR technologies so as to express a protein (a fragment or an analog thereof) having the specific amino acid motif at a C-terminus thereof. As described above, the protein having at least one amino acid motif capable of being recognized by the isoprenoid transferase may be expressed.

The term "protein" used herein is understood as two or more independently selected natural or non-natural amino acids bound by a covalent bond (for example, a peptide bond). A peptide may include 2, 3, 4, 5, 6, 7, 8, 9, 10, 11, 12, 13, 14, 15, 16, 17, 18, 19, 20, or more natural or non-natural amino acids bound by peptide bonds. Polypeptides as described herein include full length proteins (for example, fully processed proteins) as well as shorter amino acid sequences (for example, fragments of natural proteins or synthetic polypeptide fragments).

The term "protein" used herein also includes an antibody, a fragment of an antigenic polypeptide, or an analog or derivative thereof. The term "antibody" refers to an immunoglobulin molecule that recognizes and specifically binds to a target, for example, a protein, a polypeptide, a peptide, a carbohydrate, a polynucleotide, a lipid, or a combination thereof through at least one antigen recognition site within a variable region of the immunoglobulin molecule. As used herein, the term "antibody" includes intact polyclonal antibodies, intact monoclonal antibodies, antibody fragments (for example, Fab, Fab', F(ab')$_2$, Fd, and Fv fragments), single chain Fv (scFv) mutants, multispecific antibodies such as bispecific antibodies generated from two or more intact antibodies, chimeric antibodies, humanized antibodies, human antibodies, fusion proteins including an antigen determination portion of an antibody, and any other modified immunoglobulin molecule including an antigen recognition site so long as the antibodies exhibit the desired biological activity. The antibody may be any of the five major classes of immunoglobulins: IgA, IgD, IgE, IgG, and IgM, or subclasses (isotypes) thereof (for example, IgG1, IgG2, IgG3, IgG4, IgA1, and IgA2), based on the identity of their heavy chain constant domains referred to as alpha, delta, epsilon, gamma, and mu, respectively. The different classes of immunoglobulins have different and well-known subunit structures and three-dimensional configurations.

The term "antibody fragment" refers to a portion of an intact antibody and refers to antigenic determining variable regions of an intact antibody. Examples of antibody fragments include Fab, Fab', F(ab')$_2$, Fd, and Fv fragments, linear antibodies, single chain antibodies, and multispecific antibodies formed from antibody fragments.

The term "monoclonal antibody" refers to a homogeneous antibody population involved in the highly specific recognition and binding of a single antigenic determinant or epitope. This is in contrast to polyclonal antibodies that typically include different antibodies directed against a variety of different antigenic determinants. The term "monoclonal antibody" includes antibody fragments (such as Fab, Fab', F(ab')$_2$, Fd, Fv), single chain (scFv) mutants, fusion proteins including an antibody portion, and any other modified immunoglobulin molecule including an antigen recognition site as well as both intact and full-length monoclonal antibodies, but are not limited thereto. Additionally, "monoclonal antibody" refers to such antibodies made in any number of methods including but not limited to hybridoma, phage selection, recombinant expression, and transgenic animals.

The term "humanized antibody" refers to forms of non-human (e.g., murine) antibodies that are specific immunoglobulin chains, chimeric immunoglobulins, or fragments thereof that contain minimal non-human (e.g., murine) sequences. In general, humanized antibodies are human immunoglobulins in which residues from complementary determining region (CDR) are replaced by residues from CDR of a non-human species (e.g., mouse, rat, rabbit, and hamster) having the desired specificity, affinity, and capability (ref: Jones et al., 1986, Nature, 321:522-525; Riechmann et al., 1988, Nature, 332:323-327; Verhoeyen et al., 1988, Science, 239:1534-1536). In some instances, Fv framework region (FR) residues of a human immunoglobulin are replaced with the corresponding residues in an antibody from a non-human species having the desired specificity, affinity, and/or binding capability. The humanized antibody may be further modified by the substitution of additional residues either in the Fv framework region and/or within the replaced non-human residues to refine and optimize antibody specificity, affinity, and/or binding capability. In general, the humanized antibody includes substantially all of at least one, and typically two or three, variable domains containing all or substantially all of the CDRs that correspond to the non-human immunoglobulin whereas all or substantially all of the framework regions (FRs) have those of a human immunoglobulin consensus sequence. The humanized antibody may also include at least a portion of an immunoglobulin constant region or domain (Fc), typically that of a human immunoglobulin. Examples of methods used to generate humanized antibodies are described in U.S. Pat. No. 5,225,539.

The term "human antibody" as used herein refers to an antibody produced by a human or an antibody having an amino acid sequence corresponding to an antibody produced by a human using any technique known in the art. This definition of the human antibody includes intact or full-length antibodies, fragments thereof, and/or antibodies including at least one human heavy and/or light chain polypeptide such as, for example, an antibody including murine light chain and human heavy chain polypeptides.

The term "chimeric antibody" refers to an antibody wherein an amino acid sequence of an immunoglobulin molecule is derived from two or more species. In general, variable regions of both light and heavy chains correspond to variable regions of antibodies derived from one species of mammals (e.g., mouse, rat, rabbit, etc) with the desired specificity, affinity, and capability, while constant regions are homologous to the sequences in antibodies derived from another species (usually human) to avoid eliciting an immune response in that species.

The terms "epitope" and "antigenic determinant" are used interchangeably herein and refer to that portion of an antigen capable of being recognized and specifically bound by a particular antibody. When the antigen is a polypeptide, epitopes may be formed both from non-contiguous amino acids and contiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes three or more, five or more, or 8 to 10 or more amino acids in a unique spatial conformation.

An antibody "specifically binds" to an epitope or antigenic molecule, which means that the antibody reacts or associates more frequently, more rapidly, with greater duration, with greater affinity, or with some combination of the above to an epitope or antigenic molecule than alternative substances, including unrelated proteins. In specific embodiments, "specifically binds" means, for instance, that an antibody binds to a protein with a $K_D$ of about 0.1 mM or less, but more usually, less than about 1 μM. In specific embodiments, "specifically binds" means that an antibody binds to a protein at times with a $K_D$ of about 0.1 μM or less, and at other times, with about 0.01 μM or less. Because of the sequence identity between homologous proteins of different species, specific binding may include an antibody recognizing a particular protein in more than one species. It is understood that an antibody or binding residue that specifically binds to a first target may or may not specifically bind to a second target. As described above, "specific binding" does not necessarily require (although it may include) exclusive binding, that is, binding to a single target. Generally, but not necessarily, reference to binding means specific binding.

The antibodies, including fragments/derivatives thereof and monoclonal antibodies, may be obtained using methods known in the art (ref: McCafferty et al., Nature 348:552-554 (1990); Clackson et al., Nature 352:624-628; Marks et al., J. Mol. Biol. 222:581-597 (1991); Marks et al., Bio/Technology 10:779-783 (1992); Waterhouse et al., Nucleic. Acids Res. 21:2265-2266 (1993); Morimoto et al., Journal of Biochemical and Biophysical Methods 24:107-117 (1992); Brennan et al., Science 229:81 (1985); Carter et al., Bio/Technology 10:163-167 (1992); Kohler et al., Nature 256: 495 (1975); U.S. Pat. No. 4,816,567); Kilpatrick et al., Hybridoma 16(4):381-389 (1997); Wring et al., J. Pharm. Biomed. Anal. 19(5):695-707 (1999); Bynum et al., Hybridoma 18(5):407-411 (1999), Jakobovits et al., Proc. Natl. Acad. Sci. USA, 90:2551 (1993); Jakobovits et al., Nature, 362:255-258 (1993); Bruggemann et al., Year in Immuno. 7:33 (1993); Barbas et al., Proc. Nat. Acad. Sci. USA 91:3809-3813 (1994); Schier et al., Gene 169:147-155 (1995); Yelton et al., J. Immunol. 155:1994-2004 (1995); Jackson et. al., J. Immunol. 154(7):3310-9 (1995); Hawkins et al., J. Mol. Biol. 226:889-896 (1992), U.S. Pat. Nos. 5,514,548, 5,545,806, 5,569,825, 5,591,669, 5,545,807; WO 97/17852, all of which are incorporated herein by reference in their entirety).

Although not limited, the antibody may be preferably selected from the group consisting of muromonab-CD3, abciximab, rituximab, daclizumab, palivizumab, infliximab, trastuzumab (referred to as 'Herceptin'), etanercept, basiliximab, gemtuzumab ozogamicin, alemtuzumab, ibritumomab tiuxetan, adalimumab, alefacept, omalizumab, efalizumab, tositumomab-$I^{131}$, cetuximab, bevacizumab, natalizumab, ranibizumab, panitumumab, eculizumab, rilonacept, certolizumab pegol, romiplostim, AMG-531, CNTO-148, CNTO-1275, ABT-874, LEA-29Y, belimumab, TACI-Ig, second generation anti-CD20, ACZ-885, tocilizumab, atlizumab, mepolizumab, pertuzumab, HuMax CD20, tremelimumab (CP-675 206), ticilimumab, MDX-010, IDEC-114, inotuzumab ozogamicin, HuMax EGFR, aflibercept, VEGF Trap-Eye, HuMax-CD4, Ala-Ala, ChAglyCD3, TRX4, catumaxomab, IGN101, MT-201, pregovomab, CH-14.18, WX-G250, AMG-162, AAB-001, motavizumab, MEDI-524, efumgumab, Aurograb®, raxibacumab, third generation anti-CD20, LY2469298, and veltuzumab.

The term "protein" used herein also includes a repebody, which is a polypeptide optimized by consensus design through fusion of a N-terminal of internaline having a leucine-rich repeat (LRR) protein structure and a variable lymphocyte receptor (VLR) based on structural similarity thereof. The repebody may include all fusion LRR family proteins obtained by using all proteins included in a LRR family having the repeat module to improve water solubility expression and biophysical properties of proteins by the above-mentioned method.

When the protein is a monoclonal antibody, at least one light chain of the monoclonal antibody, or at least one heavy chain of the monoclonal antibody, or both may comprise an amino acid region having an amino acid motif capable of being recognized by isoprenoid transferase.

Those skilled in the art may instantly select a protein (for example, a target cell of a subject) selectively binding a target of interest. Although not limited to the above-mentioned proteins, the protein includes a fragment of an antibody or antigen specifically binding to the target of interest.

In the compounds comprising a self-immolative group according to the present invention, the amino acid motif may be CYYX, XXCC, XCXC, or CXX, (here, C represents cysteine, Y represents an aliphatic amino acid, and X represents an amino acid that determines a substrate specificity of the isoprenoid transferase) and it is more preferable that the amino acid motif is CYYX.

In the compounds comprising a self-immolative group according to the present invention, it is more preferable that the protein is the antibody or repebody.

In the compounds comprising a self-immolative group according to the present invention, B, which is the active agent, may be covalently bound to the amino acid motif existing at the carboxyl terminal of the protein via one or more linkers.

The active agent includes a drug, a toxin, an affinity ligand, a detection probe, or a combination thereof.

The drug may be selected from the group consisting of erlotinib (TARCEVA; Genentech/OSI Pharm.); bortezomib (VELCADE; Millenium Pharm.); fulvestrant (FASLODEX; AstraZeneca); sutent (SU11248; Pfizer); letrozole (FEMARA; Novartis); imatinib mesylate (GLEEVEC; Novartis); PTK787/ZK 222584 (Novartis); oxaliplatin (Eloxatin; Sanofi); 5-fluorouracil (5-FU); leucovorin; rapamycin (Sirolimus, RAPAMUNE; Wyeth); lapatinib (TYKERB, GSK572016; GlaxoSmithKline); lonafarnib (SCH 66336); sorafenib (BAY43-9006; Bayer Labs.); gefitinib (IRESSA; Astrazeneca); AG1478, AG1571 (SU 5271; Sugen); alkylating agents (for example, thiotepa or CYTOXAN® cyclophosphamide); alkyl sulfonate (for example, busulfan, improsulfan or piposulfan); aziridine (for example, benzodopa, carboquone, meturedopa, or uredopa); ethyleneimine, methylmelamine, altretamine, triethylenemelamine, triethylenephosphoramide, triethylenethiophosphoramide, trimethylolmelamine; acetogenins (for example, bullatacin or bullatacinone); camptothecin including synthetic analog topotecan; bryostatin; callystatin; CC-1065 (including its adozelesin, carzelesin, or bizelesin synthetic analogs; cryptophycins (for example, cryptophycin 1 or cryptophycin 8); dolastatin; duocarmycin (including synthetic analogs, KW-2189, and CB1-TM1); eleutherobin; pancratistatin; sarcodictyin; spongistatin; nitrogen mustard (for example, chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, or uracil mustard); nitrousurea (for example, carmustine, chlorozotocin, fotemustine, lomustine, nimustine, or ranimustine); antibiotics (for example, enediyne antibiotics such as calicheamycin selected from calicheamycin gamma 1I and calicheamycin omega I1, or dynemicin including dynemicin A); bisphosphonate (for example, clodronate; esperamicin, neocarzinostatin chromophore, or related chromoprotein enediyne antibiotic chromophores, aclacinomysins, actinomycin, anthramycin, azaserine, bleomycins, cactinomycin, carabicin, carninomycin, carzinophilin, chromomycins, dactinomycin, daunorubicin, detorubicin, 6-diazo-5-oxo-L-norleucine, ADRLIMYCIN® (doxorubicin) (for example, morpholino-doxorubicin, cyanomorpholino-doxorubicin, 2-pyrrolino-doxorubucin, liposomal doxorubicin, or deoxydoxorubicin), epirubicin, esorubicin, marcellomycin, mitomycins (for example, mitomycin C, mycophenolic acid, nogalamycin, olivomycins, peplomycin, potfiromycin, puromycin, quelamycin, rodorubicin, streptomigrin, streptozocin, tubercidin, ubenimex, zinostatin, or zorubicin); antimetabolites (for example, 5-fluorouracil (5-FU); folic acid analogs (for example, denopterin, methotrexate, pteropterin, or trimetrexate); purine analogs (for example, fludarabine, 6-mercaptopurine, thiamiprine, or thiguanine); pyrimidine analogs (for example, ancitabine, azacitidine, 6-azauridine, carmofur, cytarabine, dideoxyuridine, doxifluridine, enocitabine, or floxuridine); androgens (for example, calusterone, dromostanolone propionate, epitiostanol, mepitiostane), or testolactone); anti-adrenals (for example, aminoglutethimide, mitotane, or trilostane); folic acid replenisher (for example, folinic acid); aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; epothilone; etoglucid; gallium nitrate; hydroxyurea; lentinan; lonidainine; maytansinoids (for example, maytansine or ansamitocins); trichothecenes (particularly T-2 toxin, verracurin A, roridin A, or anguidine); mitoguazone; mitoxantrone; mopidanmol; nitraerine; pentostatin; phenamet; pirarubicin; losoxantrone; 2-ethylhydrazide; procarbazine; PSK® polysaccharide complex; razoxane; rhizoxin; sizofiran; spirogermanium; tenuazonic acid; triaziquone; 2,2',2''-trichlorotriethylamine; trichothecenes (particularly, T-2 toxin, verracurin A, roridin A, and anguidine); urethane; vindesine; dacarbazine; mannomustine; mitobronitol; mitolactol; pipobroman; gacytosine; arabinoside ('Ara-C'); cyclophosphamide; thiotepa; taxoids (for example, TAXOL® paclitaxel (Bristol-Myers Squibb Oncology, Princeton, N.J.), ABRAXANE™ cremophorfree, albumin-engineered nanoparticle formulation of paclitaxel (American Pharmaceutical Partners, Schaumber, Ill.), or TAXOTERE® doxetaxel (Rhone-Poulenc Rorer, Antony, France); chlorambucil; gemcitabine; 6-thioguanine; mercaptopurine; platinum analog (for example, cisplatin or carboplatin); vinblastine; platinum; etoposide, ifosfamide; mitoxantrone; vincristine; NAVELBINE® vinorelbine; novantrone; teniposide; edatrexate; daunomycin; aminopterin; xeloda; ibandronate; CPT-11; topoisomerase inhibitor (RFS 2000); difluoromethylornithine (DFMO); retinoid (for example, retinoic acid); capecitabine, and pharmaceutically acceptable salts, solvates, acids, or derivatives thereof, but is not necessarily limited thereto.

Although not limited, additional drugs include (i) antihormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FAREATON® toremifene; (ii) aromatase inhibitors that inhibit aromatase enzyme, which regulates estrogen production in the adrenal glands, for example, 4(5)-imidazoles, aminoglutethimide, MEGASE® megestrol acetate, AROMASIN® exemestane, FEMARA® letrozole, and ARIMIDEX® anastrozole; (iii) anti-androgens such as flutamide, nilutamide, bicalutamide, leuprolide, and goserelin; as well as troxacitabine (a 1,3-dioxolane nucleoside cytosine analog); (iv) aromatase inhibitors; (v) protein kinase inhibitors; (vi) lipid kinase inhibitors; (vii) antisense oligonucleotides, particularly those that inhibit expression of genes in signaling pathways implicated in adherent cells, for example, PKC-alpha, Raf, H-Ras; (viii) ribozyme, for example, VEGF inhibitor such as ANGIOZYME ribozyme and HER2 expression inhibitors; (ix) vaccines such as gene therapy vaccine; ALLOVECTIN® vaccine, LEUVECTIN vaccine and VAXID vaccine; PROLEUKIN® rIL-2; LURTOTECAN® topoisomerase 1 inhibitor; ABARELIX® rmRH; (x) an anti-angiogenic agent such as Bevacizumab (AVASTIN, Genentech); and (xi) pharmaceutically acceptable salts, solvates, acids, or derivatives thereof.

In addition, cytokines may be used as the drug. Cytokines are small cell-signaling protein molecules that are secreted by numerous cells and are a category of signaling molecules used extensively in intercellular communication. The cytokines include monokines, lymphokines, traditional polypeptide hormones, and the like. Examples of the cytokines include growth hormone (for example, human growth hormone, N-methionyl human growth hormone, or bovine growth hormone); parathyroid hormone; thyroxine; insulin; proinsulin; relaxin; prorelaxin; glycoprotein hormone (for example, follicle stimulating hormone (FSH), thyroid stimulating hormone (TSH), or luteinizing hormone (LH)); hepatic growth factor; fibroblast growth factor; prolactin; placental lactogen; tumornecrosis factor-$\alpha$; tumornecrosis factor-$\beta$; mullerian-inhibiting substance; mouse gonadotropin-associated peptide; inhibin; activin; vascular endothelial growth factor; integrin, thrombopoietin (TPO); nerve growth factor (for example, NGF-$\beta$); platelet-growth factor; transforming growth factor (TGF) (for example, TGF-$\alpha$ or TGF-$\beta$); insulin-like growth factor-I, insulin-like growth factor-II; erythropoietin (EPO); osteoinductive factor; interferon (for example, interferon-$\alpha$, interferon-$\beta$, or interferon-$\gamma$); colony stimulating factor (CSF) (for example, macrophage-CSF (M-CSF), granulocyte-macrophage-CSF (GM-CSF), or granulocyte-CSF (G-CSF)); interleukin (IL) (for example, IL-1, IL-1$\alpha$, IL-2, IL-3, IL-4, IL-5, IL-6, IL-7, IL-8, IL-9, IL-10, IL-11, or IL-12); tumor necrosis factor (TNF) (for example, TNF-$\alpha$ or TNF-$\beta$); and polypeptide factor (for example, LIF or kit ligand (KL)), but are not limited thereto. Further, the term "cytokine" also includes cytokines from natural sources or recombinant cell cultures and biologically active equivalents of the native sequence cytokines.

The term "toxin" refers to a poisonous substance produced within living cells or organisms. Toxins may be small molecules, peptides or proteins capable of causing diseases at the time of contact with or absorption by body tissue interacting with biological macromolecules such as enzyme or cellular receptors. Further, the toxins include plant toxins and animal toxins. Examples of animal toxins include diphtheria toxin, botulinum toxin, tetanus toxin, dysentery toxin, cholera toxin, tetrodotoxin, brevetoxin, and ciguatoxin, but are not limited thereto. Examples of plant toxins include ricin and AM-toxin, but are not limited thereto.

Examples of small molecule toxins include auristatin, tubulysin, geldanamycin (Kerr et al., 1997, Bioconjugate Chem. 8(6):781-784), maytansinoid (EP 1391213, ACR 2008, 41, 98-107), calicheamicin (US 2009105461, Cancer Res. 1993, 53, 3336-3342), daunomycin, doxorubicin, methotrexate, vindesine, SG2285 (Cancer Res. 2010, 70(17), 6849-6858), dolastatin, dolastatin analogs, auristatin (US563548603), cryptophycin, camptothecin, rhizoxin derivative, CC-1065 analog or derivative, duocarmycin, enediyne antibiotic, esperamicin, epothilone, pyrrolobenzodiazepine (PBD) derivatives, α-amanitin, and toxoid, but are not limited thereto. Toxins may exhibit cytotoxicity and cell growth-inhibiting activity by tubulin binding, DNA binding, topoisomerase suppression, and the like.

The term "ligand" refers to a molecule capable of forming a complex with a target biomolecule. An example of the ligand is a molecule bound to a predetermined position of a target protein to transmit a signal. The ligand may be a substrate, an inhibitor, a stimulating agent, a neurotransmitter, or a radioisotope.

"Detectable moiety" or a "label" refers to a composition detectable by spectroscopic, photochemical, biochemical, immunochemical, radioactive, or chemical means. For example, useful labels include $^{32}P$, $^{35}S$, fluorescent dyes, electron-dense reagents, enzymes (for example, enzymes commonly used in an ELISA), biotin-streptavidin, dioxigenin, haptens and proteins for which antisera or monoclonal antibodies are available, or nucleic acid molecules with a sequence complementary to a target. The detectable moiety often generates a measurable signal, such as a radioactive, chromogenic, or fluorescent signal, that may be used to quantify the amount of bound detectable moiety in a sample. Quantitation of the signal is achieved, for example, by scintillation counting, densitometry, flow cytometry, ELISA, or direct analysis by mass spectrometry of intact or subsequently digested peptides (one or more peptide may be assessed). Those skilled in art are familiar with techniques for labeling compounds of interest and means for detections. These techniques and methods are conventional and well-known in the art.

The term "probe" as used herein refers to a material that may (i) provide a detectable signal, (ii) interact a first probe or a second probe to modify a detectable signal provided by the first or second probe, such as fluorescence resonance energy transfer (FRET), (iii) stabilize an interaction with an antigen or a ligand or increase binding affinity; (iv) affect electrophoresis mobility or cell-intruding activity by a physical parameter such as charge, hydrophobicity, etc., or (v) control ligand affinity, antigen-antibody binding, or ionic complex formation.

The active agent includes an immunomodulatory compound, an anticancer agent, an antiviral agent, an antibacterial agent, an antifungal agent, an antiparasitic agent, or a combination thereof.

The immunomodulatory compound may be selected from the group consisting of aminocaproic acid, azathioprine, bromocriptine, chloroquine, chlorambucil, cyclosporine, cyclosporine A, danazol, dehydroepiandrosterone (DHEA), dexamethasone, etanercept, hydroxychloroquine, hydrocortisone, infliximab, meloxicam, methotrexate, cyclophosphamide, mycophenylate mofetil, prednisone, sirolimus, and tacrolimus. The anticancer agent may be selected from the group consisting of methotrexate, taxol, L-asparaginase, mercaptopurine, thioguanine, hydroxyurea, cytarabine, cyclophosphamide, ifosfamide, nitrosourea, cisplatin, carboplatin, mitomycin, dacarbazine, procarbazine, topotecan, nitrogen mustard, cytoxan, etoposide, 5-fluorouracil, bischloroethylnitrosourea (BCNU), irinotecan, camptothecin, bleomycin, doxorubicin, idarubicin, daunorubicin, dactinomycin, plicamycin, mitoxantrone, asparaginase, vinblastine, vincristine, vinorelbine, paclitaxel, docetaxel, chlorambucil, melphalan, carmustine, lomustine, busulfan, treosulfan, decarbazine, etoposide, teniposide, topotecan, 9-aminocamptothecin, crisnatol, mitomycin C, trimetrexate, mycophenolic acid, tiazofurin, ribavirin, 5-ethynyl-1-beta-D-ribofuranosylimidazole-4-carboxamide (EICAR), hydroxyurea, deferoxamine, floxuridine, doxifluridine, raltitrexed, cytarabine (ara C), cytosine arabinoside, fludarabine, tamoxifen, raloxifene, megestrol, goserelin, leuprolide acetate, flutamide, bicalutamide, EB1089, CB1093, KH1060, verteporfin, phthalocyanine, photosensitizer Pe4, demethoxy-hypocrellin A, interferon-α, interferon-γ, tumor necrosis factor, gemcitabine, velcade, revlimid, thalomid, lovastatin, 1-methyl-4-phenylpyridinium ion, staurosporine, actinomycin D, dactinomycin, bleomycin A2, bleomycin B2, peplomycin, epirubicin, pirarubicin, zorubicin, mitoxantrone, verapamil, and thapsigargin. The antiviral agent may be selected from the group consisting of pencicyclovir, valacyclovir, gancicyclovir, foscarnet, ribavirin, idoxuridine, vidarabine, trifluridine, acyclovir, famcicyclovir, amantadine, rimantadine, cidofovir, antisense oligonucleotide, immunoglobulin, and interferon. The antibacterial agent may be selected from the group consisting of chloramphenicol, vancomycin, metronidazole, trimethoprin, sulfamethazole, quinupristin, dalfopristin, rifampin, spectinomycin, and nitrofurantoin. The antifungal agent may be selected from the group consisting of amphotericin B, candidicin, filipin, hamycin, natamycin, nystatin, rimocidin, bifonazole, butoconazole, clotrimazole, econazole, fenticonazole, isoconazole, ketoconazole, luliconazole, miconazole, omoconazole, oxiconazole, sertaconazole, sulconazole, tioconazole, albaconazole, fluconazole, isavuconazole, itraconazole, posaconazole, ravuconazole, terconazole, voriconazole, abafungin, amorolfin, butenafine, naftifine, terbinafine, anidulafungin, caspofungin, micafungin, benzoic acid, ciclopirox, flucytosine, griseofulvin, haloprogin, tolnaftate, undecylenic acid, crystal violet, balsam of peru, ciclopirox olamine, piroctone olamine, zinc pyrithione, and selenium sulfide. The antiparasitic agent may be selected from the group consisting of mebendazole, pyrantel pamoate, thiabendazole, diethylcarbamazine, ivermectin, niclosamide, praziquantel, albendazole, rifampin, amphotericin B, melarsoprol, eflornithine, metronidazole, tinidazole, and miltefosine.

In the compounds comprising a self-immolative group according to the present invention, the protein having an amino acid motif may be selected from the group consisting of A-HC-(G)$_z$CVIM, A-HC-(G)$_z$CVLL, A-LC-(G)$_z$CVIM, and A-LC-(G)$_z$CVLL, wherein A represents an antibody, HC represents a heavy chain, a LC represents a light chain, G represents a glycine unit, and z is an integer of 0 to 20.

The compounds comprising a self-immolative group according to the present invention may be selected from compounds having the following structures.

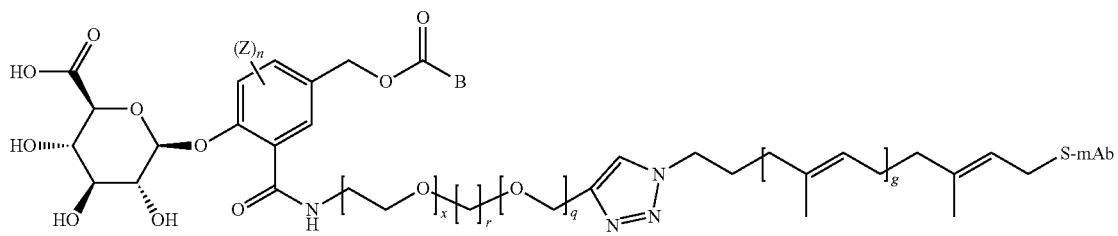

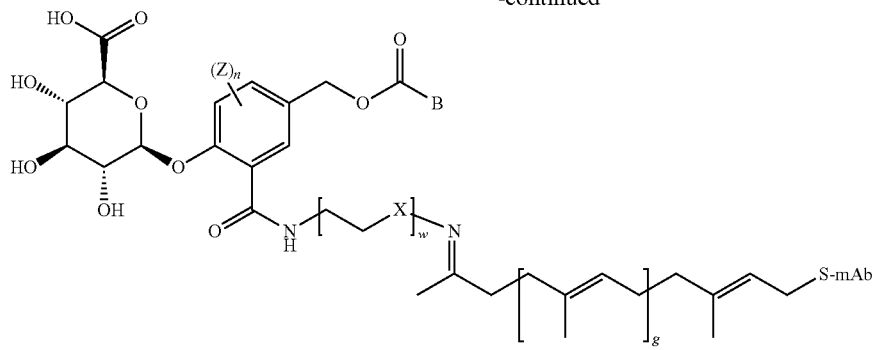

Here,

Z is hydrogen, $(C_1-C_8)$alkyl, halogen, cyano, or nitro;

X is —O—, $(C_1-C_8)$alkylene, or —$NR_{21}$—;

$R_{21}$ is hydrogen, $(C_1-C_6)$alkyl, $(C_1-C_6)$alkyl$(C_6-C_{20})$aryl, or $(C_1-C_6)$alkyl$(C_3-C_{20})$heteroaryl;

n is an integer of 1 to 3, and when n is an integer of 2 or more, each of the Z(s) are the same as or different from each other;

r is an integer of 1 to 10;

q is an integer of 1 to 10;

w is an integer of 1 to 10.

x is an integer of 0 to 10;

g is an integer of 1 to 10;

—S-mAb is A-HC-$(G)_z$CVIM-, A-HC-$(G)_z$CVLL-, A-LC-$(G)_z$CVIM-, or A-LC-$(G)_z$CVLL-, wherein A represents an antibody, HC represents a heavy chain, LC represents a light chain, G represents a glycine unit, and z is an integer of 0 to 20;

B is a drug having a structure selected from the following structures; and

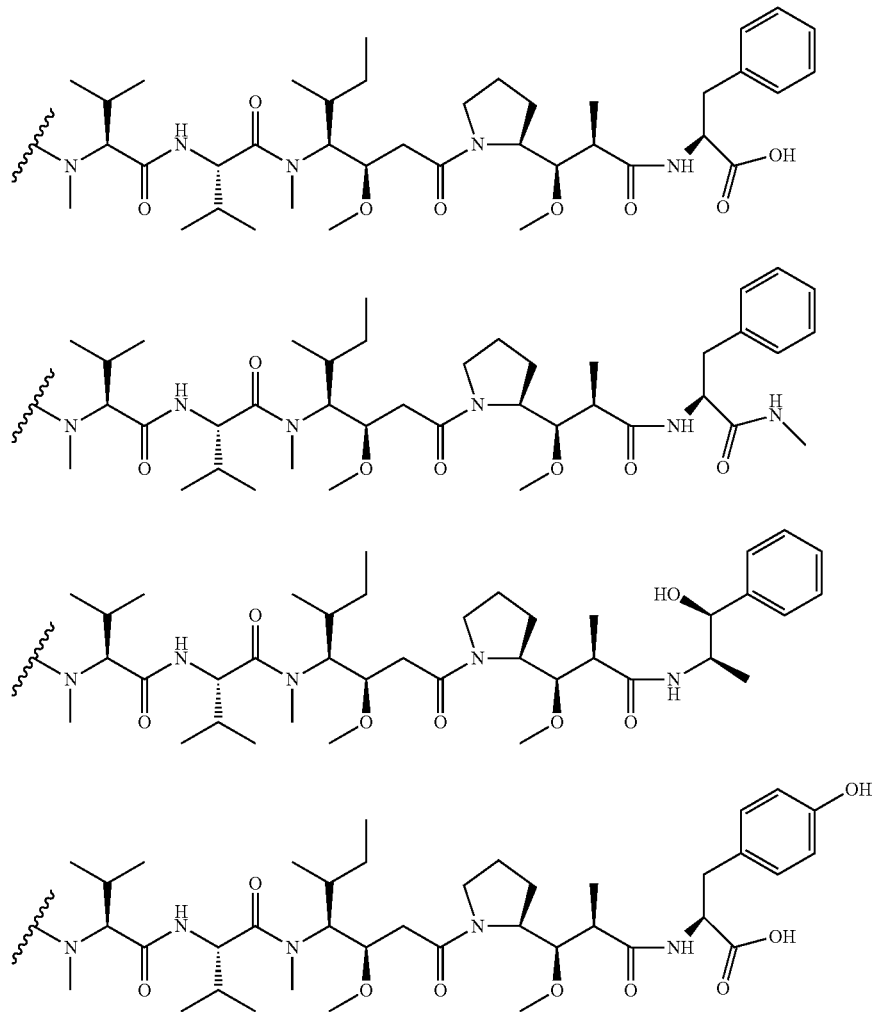

-continued
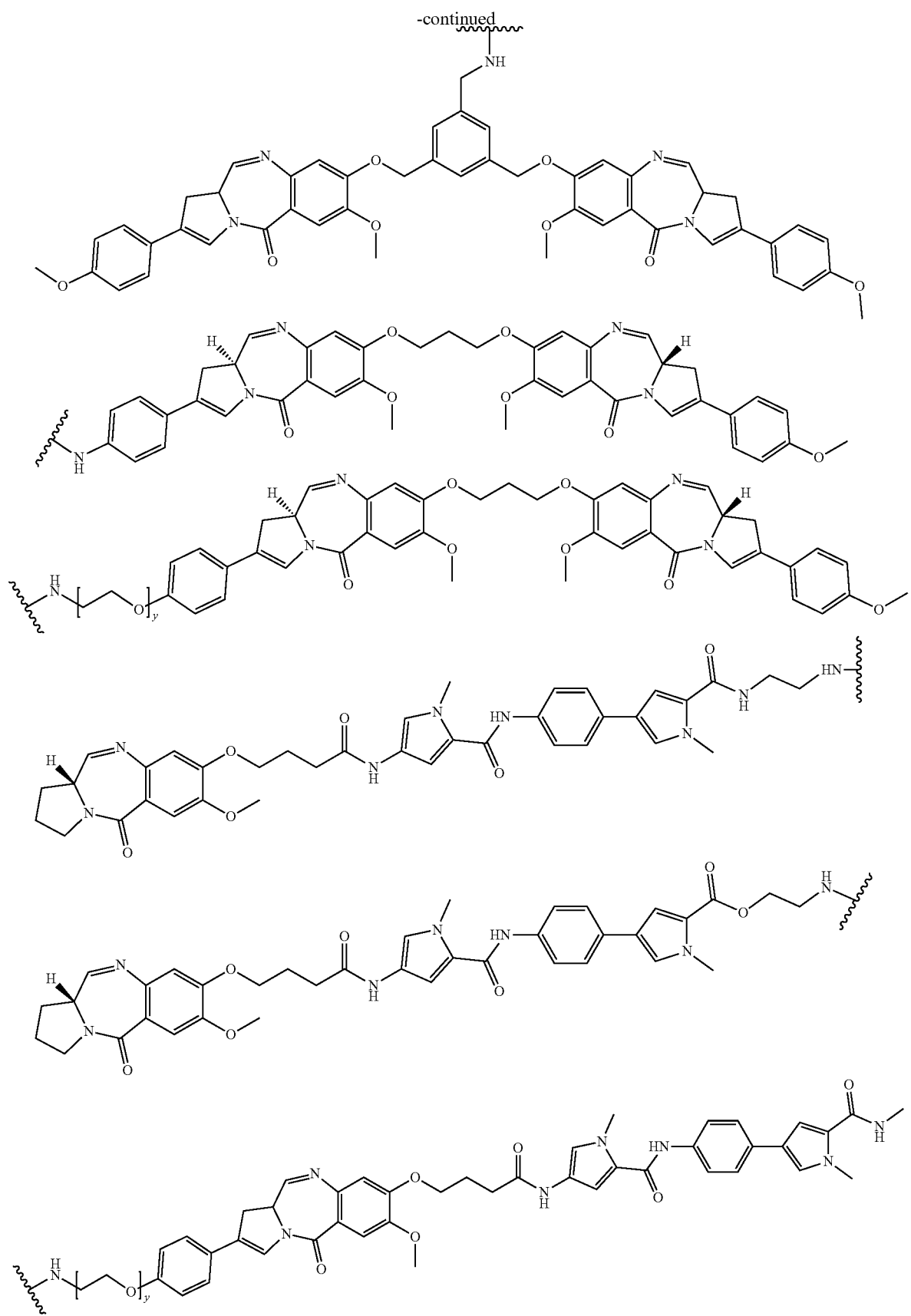
y is an integer of 1 to 10.

In the compounds comprising a self-immolative group of Chemical Formula 1 according to the present invention, when A is a protein and B is an active agent, the compound may be used to transfer the active agent to a target cell of a subject to treat the subject using a method of preparing a composition known to those skilled in the art.

Compositions are prepared in an injectable form, either as a liquid solution or as a suspension. Solid forms suitable for injection may also be prepared as emulsions, or with polypeptides encapsulated in liposomes. The compounds comprising a self-immolative group may be combined with a pharmaceutically acceptable carrier, which includes any carrier that does not induce production of antibodies harmful to the subject receiving the carrier. Suitable carriers typically comprise large macromolecules that are slowly metabolized, for example, proteins, polysaccharides, polylactic acids, polyglycolic acids, polymeric amino acids, amino acid copolymers, lipid aggregates, and the like. These carriers are well known to those skilled in the art.

The compositions may also contain diluents, for example, water, saline, glycerol, and ethanol. Auxiliary substances, for example, wetting or emulsifying agents, pH buffering substances, and the like may also be present therein. Proteins may be formulated into vaccines as neutral or salt forms. The compositions may be parenterally administered by injection wherein such injection may be either subcutaneous or intramuscular injection. Additional formulations are suitable for other forms of administration, such as suppository or oral administration. Oral compositions may be administered as a solution, suspension, tablet, pill, capsule, or sustained release formulation.

The compositions are administered in a manner compatible with a dose and a formulation. The composition comprises a therapeutically effective amount of the compound comprising a self-immolative group. By a "therapeutically effective amount" is meant a single dose, or a composition administered in a multiple dose schedule, that is effective for the treatment or prevention of a disease or disorder. An administration dose may vary, depending on the subject to be treated, the subject's health and physical conditions, a degree of protection to be desired, and other relevant factors. An accurately required amount of an active ingredient depends on the judgment of a doctor.

For example, a therapeutically effective amount of the compound comprising a self-immolative group or composition containing the same may be administered to a patient suffering from cancer or tumor to treat cancer or tumor.

A therapeutically effective amount of the compound comprising a self-immolative group or composition containing the same may be administered to a patient to treat or prevent infection by pathogens (for example, virus, bacteria, fungi, parasites, or the like). These methods include administering a therapeutic or prophylactic amount of the compound comprising a self-immolative group, sufficient to treat a disease or disorder or symptoms thereof, to mammal animals, under conditions at which the disease or disorder is prevented or treated.

The compound comprising a self-immolative group according to the present invention or the composition containing the same may be administered in a form of a pharmaceutically acceptable salt or solvate thereof. In some embodiments, the compound comprising a self-immolative group according to the present invention or the composition containing the same may be administered with a pharmaceutically acceptable carrier, a pharmaceutically acceptable excipient, and/or a pharmaceutically acceptable additive. The pharmaceutically effective amount and the type of the pharmaceutically acceptable salt or solvate, excipient and additive may be measured using standard methods (ref: Remington's Pharmaceutical Sciences, Mack Publishing Co., Easton, Pa., 18th Edition, 1990).

The term "therapeutically effective amount" with regard to cancer or tumor means an amount that may decrease the number of cancer cells; decrease a size of cancer cells; prohibit cancer cells from intruding peripheral systems or decrease the intrusion; prohibit cancer cells from spreading to other systems or decrease the spreading; prohibit cancer cells from growing; and/or ameliorate at least one symptom related to the cancer. In the treatment of cancer, the effectiveness of a drug may be assessed by time to tumor progression (TTP) and/or response rate (RR).

The term "therapeutically effective amount" with regard to infection by pathogens means an amount that can prevent, treat, or reduce the symptoms associated with infection.

The term "pharmaceutically acceptable salts" used herein includes organic salts and inorganic salts. Examples thereof include hydrochloride, hydrobromide, hydroiodide, sulfate, citrate, acetate, oxalate, chloride, bromide, iodide, nitrate, bisulfate, phosphate, acidic phosphate, isonicotinate, lactate, salicylate, acidic citrate, tartrate, oleate, tannate, pantonate, bitartrate, ascorbate, succinate, maleate, gentisinate, fumarate, gluconate, glucoronate, saccharate, formate, benzoate, glutamate, methane sulfonate, ethane sulfonate, benzene sulfonate, p-toluene sulfonate, and pamoate (that is, 1,1'-methylenebis-(2-hydroxy-3-naphthoate)), but are not limited thereto. The pharmaceutically acceptable salt may include another molecule (for example, acetate ions, succinate ions, and other counter ions, etc.). The pharmaceutically acceptable salt may also include at least one charged atom. The pharmaceutically acceptable salt may also include at least one counter ion.

Exemplary solvates that may be used for pharmaceutically acceptable solvates of the compounds comprising a self-immolative group according to the present invention include water, isopropanol, ethanol, methanol, dimethyl sulfoxide (DMSO), ethyl acetate, acetic acid, and ethanol amine, but are not limited thereto.

Hereinafter, configurations of the present invention will be described in detail through Examples, but the following Examples are only to assist in understanding of the present invention. Therefore, the scope of the present invention is not limited thereto.

[Example 1] Preparation of Compound 1k

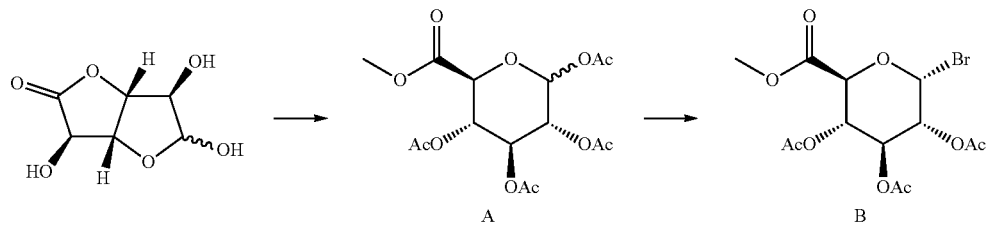

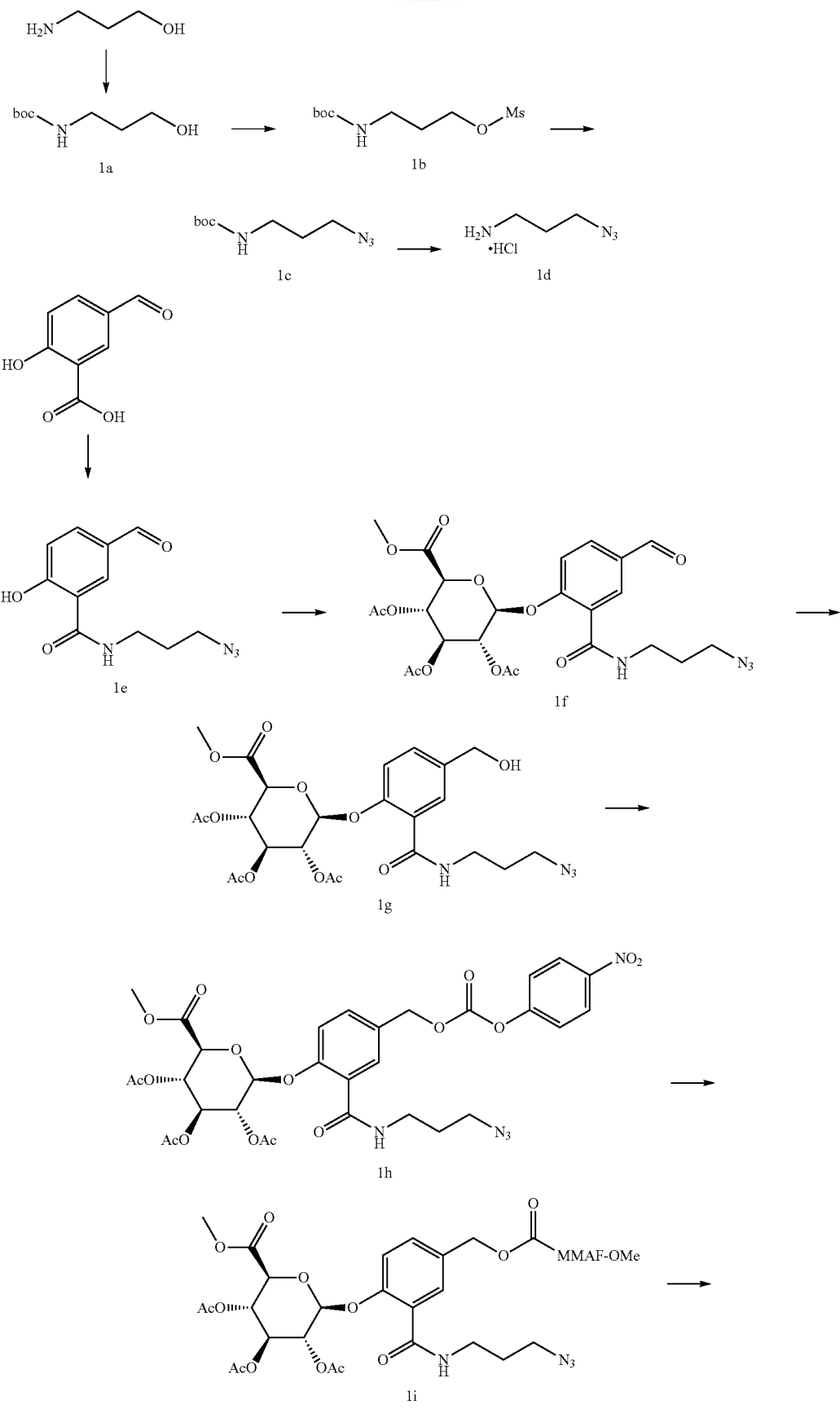

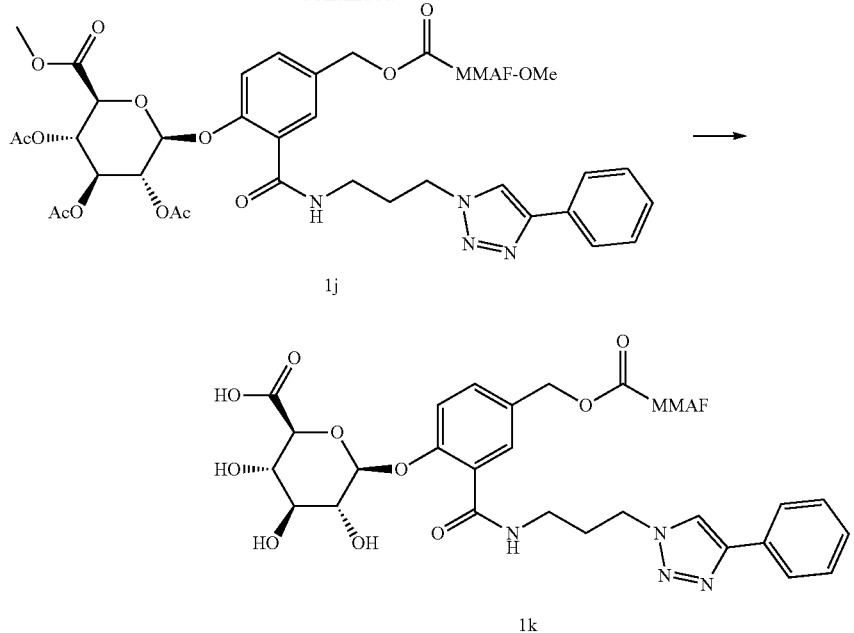

1j

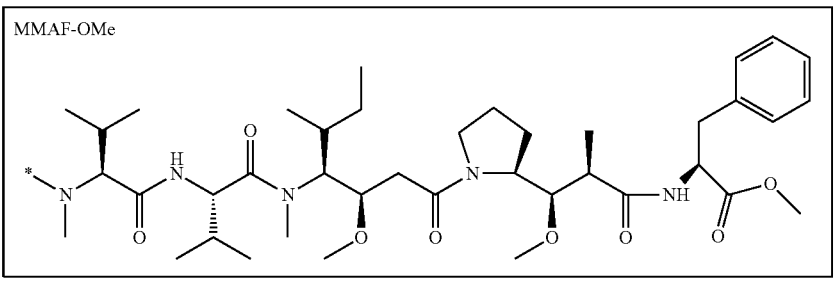

1k

MMAF-OMe

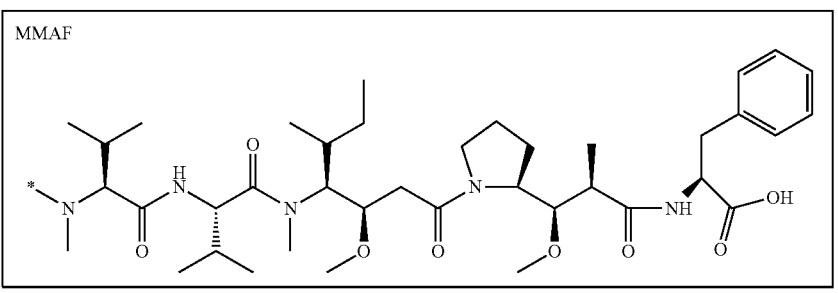

MMAF

Preparation of Compound A

D-glucurono-6,3-lactone (19 g, 107.88 mmol) was dissolved in methanol (250 mL) at room temperature under nitrogen atmosphere, a solution of NaOH (100 mg) in methanol (100 mL) was slowly added thereto and stirred for 2 hours, and then, a solution of NaOH (200 mL) in methanol (15 mL) was added to the mixture and stirred for 3 hours. After the reaction was completed, the methanol solvent of the mixture was removed under reduced pressure, and pyridine (50 mL) and acetic anhydride (54 mL) were added thereto at 10° C. or less and stirred at room temperature for 4 hours. After the reaction was completed, the resultant was concentrated under reduced pressure. The residue was subjected to column chromatography, thereby obtaining Compound A (20 g, 50%).

$^1$H NMR (600 MHz, CDCl$_3$) δ 5.77 (d, J=7.8 Hz, 1H), 5.31 (t, J=9.6 Hz, 1H), 5.24 (t, J=9.6 Hz, 1H), 5.14 (m, 1H), 4.17 (d, J=9 Hz, 1H), 3.74 (s, 3H), 2.12 (s, 3H), 2.04 (m, 9H)

Preparation of Compound B

Compound A (5 g, 13.28 mmol) was dissolved in 33% HBr in AcOH (20 mL) at 0° C. under nitrogen atmosphere and then, stirred at room temperature for 2 hours. After the reaction was completed, toluene (50 L) was added thereto, and the mixture was concentrated under reduced pressure. Thereafter, ethylacetate (100 mL) and —NaHCO$_3$ solution (100 mL) were added thereto to extract an organic layer, and the obtained organic layer was dried over anhydrous sodium sulfate, followed by concentration under reduced pressure. The residue was subjected to column chromatography, thereby obtaining Compound B (5.27 g, 100%).

¹H NMR (600 MHz, CDCl₃) δ 6.64 (d, J=3.6 Hz, 1H), 5.61 (t, J=3.6 Hz, 1H), 5.24 (t, J=3.6 Hz, 1H), 4.85 (m, 1H), 4.58 (d, d, J=10.2 Hz, 1H), 3.76 (s, 3H), 2.10 (s, 3H), 2.06 (s, 3H), 2.05 (s, 3H)

Preparation of Compound 1a (U.S. Pat. No. 6,414,148, 2002)

3-amino-1-propanol (3.0 g, 66.569 mmol) was dissolved in dichloromethane (150 mL) at 0° C. under nitrogen atmosphere, and di-tert-butyldicarbonate (16 g, 73.226 mmol) was added thereto. The obtained mixture was stirred at room temperature for 12 hours. After the reaction was completed, the solvent was concentrated under reduced pressure. The residue was subjected to column chromatography, thereby obtaining Compound 1a (6.4 g, 92%).

¹H NMR (400 MHz, CDCl₃) δ 4.78 (s, 1H), 3.65 (m, 2H), 3.30 (m, 2H), 2.90 (s, 1H), 1.68 (m, 2H), 1.48 (s, 9H); EI-MS m/z: 176 (M+)

Preparation of Compound 1b (WO2008/157726)

Compound 1a (6.04 g, 34.469 mmol) and triethylamine (TEA, 14.4 mL, 103.407 mmol) were dissolved in tetrahydrofuran at 0° C. under nitrogen atmosphere and then, slowly treated with methanesulfonic anhydride (7.21 g, 41.363 mmol). The obtained mixture was stirred at room temperature under nitrogen atmosphere for 12 hours. After the reaction was completed, the solvent was concentrated under reduced pressure. The residue was subjected to column chromatography, thereby obtaining Compound 1b (9.01 g, 98%).

¹H NMR (400 MHz, CDCl₃) δ 4.73 (s, 1H), 4.30 (t, J=5.9 Hz, 2H), 3.31-3.24 (m, 2H), 3.04 (s, 3H), 1.94 (t, J=6.1 Hz, 2H), 1.44 (s, 9H). EI-MS m/z: 254 (M+)

Preparation of Compound 1c (WO2013/166319)

Compound 1b (3.0 g, 11.842 mol) was dissolved in dimethylformamide (40 mL) at room temperature under nitrogen atmosphere, and then, treated with sodium azide (924 mg, 14.211 mmol), and the obtained mixture was stirred at 60° C. for 12 hours. After the reaction was completed, ethylacetate (50 mL), distilled water (50 mL), and 1N HCl (5 mL) were added thereto. The organic layer obtained as described above was dried over anhydrous sodium sulfate and concentrated under reduced pressure. The residue was subjected to column chromatography, thereby obtaining Compound 1c (2.3 g, 99%).

¹H NMR (600 MHz, CDCl₃) δ 4.63 (s, 1H), 3.36 (t, J=6.6 Hz, 2H), 3.24-3.18 (m, 2H), 1.80-1.75 (m, 2H), 1.45 (s, 9H). EI-MS m/z: 201 (M+)

Preparation of Compound 1d

After compound 1c (3.8 g, 18.977 mmol) was dissolved in dichloromethane (10 mL) at 0° C. under nitrogen atmosphere, 4M-HCl in dioxane (10 mL) was slowly added thereto. The obtained mixture was stirred for 12 hours. After the reaction was completed, the resultant was concentrated under reduced pressure, thereby obtaining Compound 1d (2.5 g, 99%).

¹H NMR (600 MHz, DMSO-d₆) δ 8.06 (s, 3H), 3.47 (t, J=6.6 Hz, 2H), 2.82 (t, J=7.2 Hz, 2H), 1.84-1.79 (m, 2H). EI-MS m/z: 101 (M+)

Preparation of Compound 1e

After Compound 1d (58 mg, 0.420 mmol) and 5-formylsalicylic acid (100 mg, 0.601 mmol) were dissolved in dimethylformamide (DMF, 2 mL) at 0° C. under nitrogen atmosphere, diisopropylethylamine (DIPEA, 0.2 mL, 1.202 mmol) and PyBop (375 mg, 0.721 mmol) were added to the mixed solution. The obtained mixture was stirred at room temperature for 3 hours. After the reaction was completed, ethylacetate (30 mL) and distilled water (10 mL) were added thereto. The organic layer obtained as described above was dried over anhydrous sodium sulfate and concentrated under reduced pressure. The residue was subjected to column chromatography, thereby obtaining Compound 1e (82 mg, 79%).

¹H NMR (400 MHz, CDCl₃) δ 13.39 (s, 1H), 9.87 (s, 1H), 8.29 (s, 1H), 7.89 (dd, J=1.6, 7.2 Hz. 1H), 7.60 (s, 1H), 7.10 (d, J=8.8 Hz), 3.63-3.57 (m, 2H), 3.48 (t, J=6.4 Hz, 2H), 1.99-1.92 (m, 2H). EI-MS m/z: 249 (M+)

Preparation of Compound 1f

After Compound 1e (78 mg, 0.314 mmol) and Compound B (125 mg, 0.314 mmol) were dissolved in acetonitrile (3 mL) at room temperature under nitrogen atmosphere, silver oxide (291 mg, 1.256 mmol) and molecular sieve (125 mg) were added thereto. The obtained mixture was stirred at room temperature for 3 hours. After the reaction was completed, the mixture was celite-filtered, and the filtrate was concentrated under reduced pressure. The residue was subjected to column chromatography, thereby obtaining Compound 1f (160 mg, 90%).

¹H NMR (400 MHz, CDCl₃) δ 10.00 (s, 1H), 8.66 (d, J=2.4 Hz, 1H), 8.02 (dd, J=2.0, 6.4 Hz, 1H), 7.46 (t, J=6.4 Hz, 1H), 7.14 (d, J=8.4 Hz, 1H), 5.48-5.33 (m, 4H), 4.28 (d, J=8.8 Hz, 1H), 3.74 (s, 3H), 3.73-3.64 (m, 1H), 3.50-3.42 (m, 3H), 2.09-2.07 (m, 9H), 2.00-1.92 (m, 2H). EI-MS m/z: 565 (M+)

Preparation of Compound 1g

After Compound 1f (160 mg, 1.510 mmol) was dissolved in 2-propanol (0.4 mL) and chloroform (2 mL) at 0° C. under nitrogen atmosphere, silica gel (2 g) and sodium borohydride (27 mg, 0.708 mmol) were added thereto. After the obtained mixture was stirred at 0° C. for 2 hours, the reactant was celite-filtered, and the filtrate was concentrated under reduced pressure. The residue was subjected to column chromatography, thereby obtaining Compound 1g (115 mg, 71%).

¹H NMR (600 MHz, CDCl₃) δ 8.06 (d, J=2.4 Hz, 1H), 7.50-7.44 (m, 2H), 7.01 (d, J=90 Hz, 1H), 5.45-5.31 (m, 4H), 4.38 (s, 2H), 4.22 (d, J=9.0 Hz, 1H), 3.74 (s, 3H), 3.67-3.61 (m, 1H), 3.46-3.41 (m, 3H), 2.07-2.04 (m, 9H), 1.97-1.91 (m, 2H). EI-MS m/z: 567 (M+)

Preparation of Compound 1h

After Compound 1g (100 mg, 0.177 mmol) was dissolved in DMF (1 mL) at 0° C. under nitrogen atmosphere, bis(4-nitrophenyl)carbonate (110 mg, 0.353 mmol) and DIPEA (50 uL, 0.265 mmol) were added thereto. The obtained mixture was stirred at room temperature for 2 hours. After the reaction was completed, ethylacetate (30 mL) and distilled water (10 mL) were added thereto. The organic layer obtained as described above was dried over anhydrous sodium sulfate and concentrated under reduced pressure. The residue was subjected to column chromatography, thereby obtaining Compound 1h (75 mg, 58%).

¹H NMR (600 MHz, CDCl₃) δ 8.29-8.27 (m, 2H), 8.23 (d, J=2.4 Hz, 1H), 7.54 (dd, J=2.4, 6.6 Hz, 1H), 7.49 (t, J=6.4 Hz, 1H), 7.39-7.37 (m, 2H), 7.04 (d, J=8.4 Hz, 1H), 5.45-5.29 (m, 4H), 5.28 (s, 2H), 4.23 (d, J=9.0 Hz, 1H), 3.75 (s, 3H), 3.68-3.64 (m, 1H), 3.46-3.42 (m, 3H), 2.08-2.05 (m, 9H), 1.98-1.93 (m, 2H). EI-MS m/z: 732 (M+)

Preparation of Compound 1i

After Compound 1h (50 mg, 0.068 mmol) was dissolved in DMF (0.8 mL) at room temperature under nitrogen atmosphere, MMAF-OMe (51 mg, 0.068 mmol) was added thereto, and then, the resultant was treated with 1-hydroxybenzotriazole anhydrous (HOBT, 2 mg, 0.013 mmol), pyridine (0.24 mL), and DIPEA (12 uL, 0.068 mmol). The obtained mixture was stirred at room temperature for 18 hours. After the reaction was completed, ethylacetate (20 mL) and distilled water (10 mL) were added thereto. The organic layer obtained as described above was dried over anhydrous sodium sulfate and concentrated under reduced pressure. The residue was subjected to column chromatography, thereby obtaining Compound 1i (71 mg, 78%).

EI-MS m/z: 1339 (M+)

Preparation of Compound 1j

After Compound 1i (30 mg, 0.022 mmol) and phenylacetylene (3.7 uL, 0.033 mmol) were dissolved in ethanol (0.2 mL) and water (30 ul) at room temperature under nitrogen atmosphere, 0.1M CuSO$_4$ aqueous solution (30 ul) and 1.0M sodium ascorbate aqueous solution (30 ul) were added thereto, the resultant was treated with HOBT (2 mg, 0.013 mmol), pyridine (0.24 mL), and DIPEA (12 uL, 0.068 mmol). The obtained mixture was stirred at room temperature for 5 hours. After the reaction was completed, ethylacetate (20 mL) and distilled water (5 mL) were added thereto. The organic layer obtained as described above was dried over anhydrous sodium sulfate and concentrated under reduced pressure. The residue was subjected to column chromatography, thereby obtaining Compound 1j (26 mg, 81%).

EI-MS m/z: 1441 (M+)

Preparation of Compound 1k

After Compound 1j (20 mg, 0.013 mmol) was dissolved in methanol (0.2 mL) at 0° C. under nitrogen atmosphere, LiOH.H$_2$O (6 mg, 0.138 mmol) in water (0.2 mL) was added thereto. The obtained mixture was stirred at room temperature for 1 hour. After the reaction was completed, chloroform (10 mL), methanol (1 mL), distilled water (10 mL), and 0.5N HCl (1 mL) were added thereto. The organic layer obtained as described above was dried over anhydrous sodium sulfate and concentrated under reduced pressure. The residue was subjected to column chromatography, thereby obtaining Compound 1k (17 mg, 87%).

EI-MS m/z: 1286 (M+)

[Examples 2 and 3] Preparation of Compounds 2i and 3i

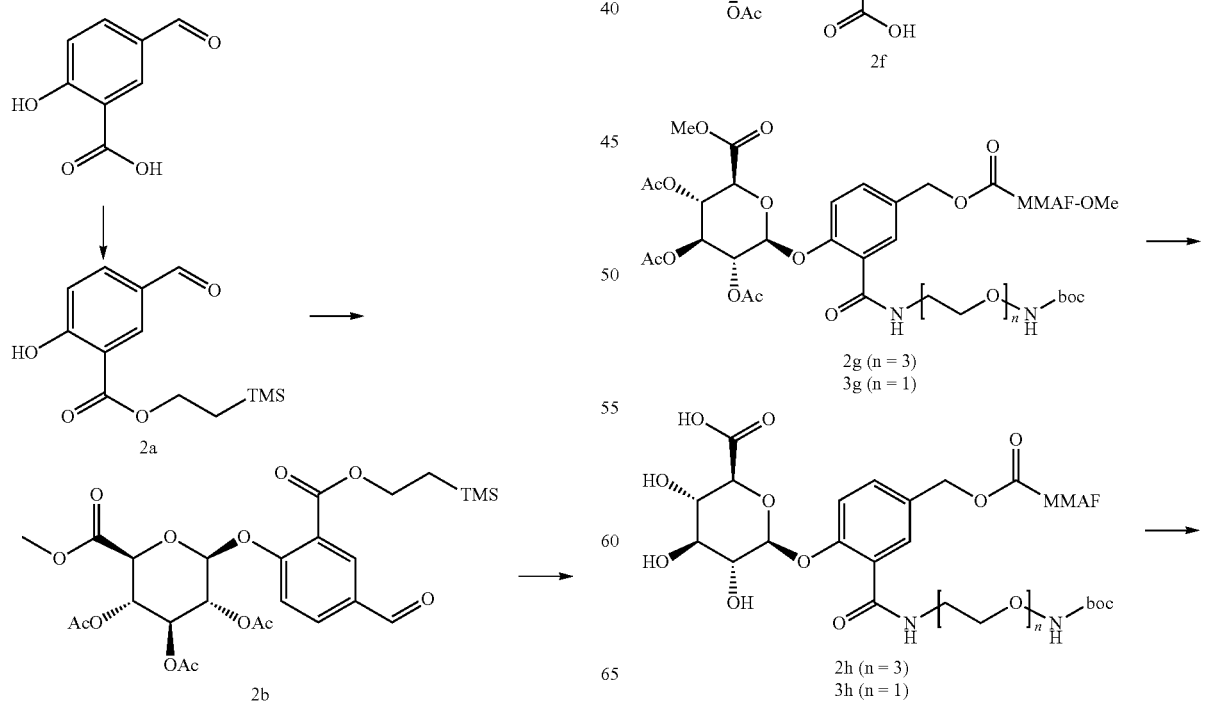

-continued

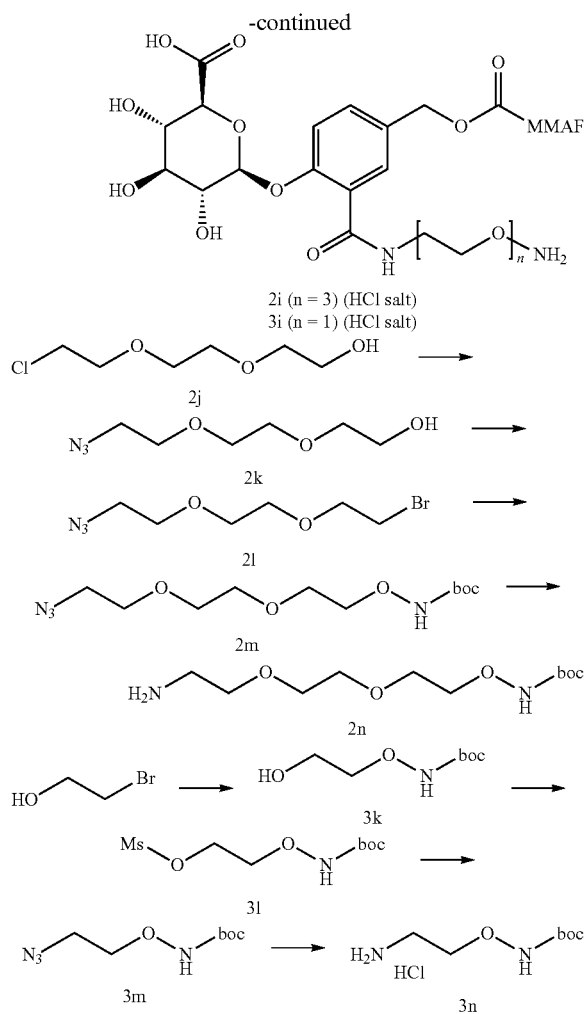

2i (n = 3) (HCl salt)
3i (n = 1) (HCl salt)

Preparation of Compound 2a

After 5-formylsalicylic acid (2 g, 12.038 mmol) was dissolved in DMF at 0° C. under nitrogen atmosphere, 2-(trimethylsilyl)ethanol (1.72 mL, 12.038 mmol) and dimethylaminopyridine (DMAP, 147 mg, 1.204 mmol), and dicyclohexylcarbodiimide (DCC, 2.5 g, 12.038 mmol) were added thereto. The mixture was stirred at room temperature for 12 hours. After the reaction was completed, ethylacetate (100 mL) and distilled water (100 mL) were added thereto. The organic layer obtained as described above was dried over anhydrous sodium sulfate and concentrated under reduced pressure. The residue was subjected to column chromatography, thereby obtaining Compound 2a (1.6 g, 50%).

$^1$H NMR (400 MHz, CDCl$_3$) δ 11.38 (s, 1H), 9.77 (s, 1H), 7.48 (d, J=8.4 Hz, 1H), 6.61 (dd, J=8.4, 2.0 Hz, 1H), 6.53 (d, J=2.0 Hz, 1H), 5.36-5.25 (m, 4H), 4.23 (m, 1H), 3.73 (s, 1H), 2.06 (s, 9H)

Preparation of Compound 2b

After Compound 2a (60 mg, 0.225 mmol) was dissolved in acetonitrile (2 mL) at room temperature under nitrogen atmosphere, and then, Compound C (90 mg, 0.225 mmol), silver oxide (209 mg, 0.900 mmol), and molecular sieve (90 mg) were added thereto. The mixture was stirred at room temperature for 2 hours. After the reaction was completed, ethylacetate (50 mL) and distilled water (30 mL) were added thereto. The organic layer obtained as described above was dried over anhydrous sodium sulfate and concentrated under reduced pressure. The residue was subjected to column chromatography, thereby obtaining Compound 2b (103 mg, 79%).

$^1$H NMR (400 MHz, CDCl$_3$) δ 9.93 (s, 1H), 8.22 (d, J=2.0 Hz, 1H), 7.97 (dd, J=6.4, 2.0 Hz, 1H), 7.26 (d, J=9.2 Hz, 1H), 5.42-5.27 (m, 4H), 4.42-4.30 (m, 2H), 4.24 (d, J=9.2 Hz, 1H), 3.70 (s, 3H), 2.06-2.04 (m, 9H), 1.14-1.08 (m, 2H), 0.07 (s, 9H)

Preparation of Compound 2c

After Compound 2b (100 mg, 0.171 mmol) was dissolved in 2-propanol (0.3 mL) and chloroform (1.5 mL) at 0° C. under nitrogen atmosphere, silica gel (720 mg) and sodium borohydride (16 mg, 0.427 mmol) were added thereto. The mixture was stirred for 3 hours. After the reaction was completed, ethylacetate (50 mL) and distilled water (20 mL) were added thereto. The organic layer obtained as described above was dried over anhydrous sodium sulfate and concentrated under reduced pressure. The residue was subjected to column chromatography, thereby obtaining Compound 2c (94 mg, 94%).

$^1$H NMR (400 MHz, CDCl$_3$) δ 7.71 (d, J=2.0 Hz, 1H), 7.45 (dd, J=6.4, 2.0 Hz, 1H), 7.17 (d, J=8.4 Hz, 1H), 5.40-5.30 (m, 3H), 5.16-5.14 (m, 1H), 4.67 (s, 2H), 4.40-4.29 (m, 2H), 4.18 (d, J=8.8 Hz, 1H), 3.74 (s, 3H), 2.08-2.04 (m, 9H), 1.14-1.09 (m, 2H), 0.08 (s, 9H)

Preparation of Compound 2d

After Compound 2c (90 mg, 0.154 mmol) was dissolved in DMF (1.0 mL) at 0° C. under nitrogen atmosphere, bis(4-nitrophenyl)carbonate (94 mg, 0.308 mmol) and DIPEA (40 uL, 0.231 mmol) were added thereto. The mixture was stirred at room temperature for 3 hours. After the reaction was completed, ethylacetate (50 mL) and distilled water (20 mL) were added thereto. The organic layer obtained as described above was dried over anhydrous sodium sulfate and concentrated under reduced pressure. The residue was subjected to column chromatography, thereby obtaining Compound 2d (104 mg, 90%).

$^1$H NMR (400 MHz, CDCl$_3$) δ 8.28 (m, 2H), 7.80 (d, J=2.4 Hz, 1H), 7.53 (dd, J=6.4, 2.0 Hz, 1H), 7.37 (m, 2H), 7.20 (d, J=8.8 Hz, 1H), 5.41-5.33 (m, 3H), 5.25 (s, 2H), 5.20-5.18 (m, 1H), 4.41-4.30 (m, 2H), 4.20 (d, J=8.8 Hz, 1H), 3.74 (s, 3H), 2.08-2.05 (m, 9H), 1.18-1.06 (m, 2H), 0.08 (s, 9H)

Preparation of Compound 2e

After Compound 2d (1.5 g, 2.00 mmol) was dissolved in DMF (8 mL) at room temperature under nitrogen atmosphere, MMAF-OMe (1.34 g, 1.80 mmol) was added thereto, and then, the resultant was treated with HOBT (54 mg, 0.4 mmol), pyridine (5.4 mL), and DIPEA (0.383 mL, 2.2 mmol). The mixture was stirred at room temperature for 12 hours. After the reaction was completed, ethylacetate (200 mL) and distilled water (300 mL) were added thereto. The organic layer obtained as described above was dried over anhydrous sodium sulfate and concentrated under reduced pressure. The residue was subjected to column chromatography, thereby obtaining Compound 2e (1.7 g, 70%).

EI-MS m/z: 1357 (M$^+$)

Preparation of Compound 2f

After Compound 2e (1.7 g, 1.253 mmol) was dissolved in THF (15 mL) at 0° C. under nitrogen atmosphere, tetrabutylammonium fluoride (1M in THF) (2.5 mL, 2.506 mmol) was added thereto and stirred at room temperature for 4 hours. After the reaction was completed, ethylacetate (200 mL) and distilled water (300 mL) were added thereto. The organic layer obtained as described above was dried over anhydrous sodium sulfate and concentrated under reduced pressure. The residue was subjected to column chromatography, thereby obtaining Compound 2f (1.34 g, 85%).

EI-MS m/z: 1257 (M$^+$)

Preparation of Compound 2k

After Compound 2j (10 g, 59.3 mmol) was dissolved in DMF (90 mL) at room temperature under nitrogen atmosphere, sodium azide (5.78 g, 88.9 mmol) was added thereto, and the mixture was stirred at 100° C. for 13 hours. After the reaction was completed, chloroform (200 mL) and distilled water (300 mL) were added thereto to extract an organic layer, and the extracted organic layer was dried over anhydrous sodium sulfate and concentrated under reduced pressure. The residue was subjected to column chromatography, thereby obtaining Compound 2k (10.3 g, 99%).

$^1$H NMR (600 MHz, CDCl$_3$) δ 3.75-3.73 (m, 2H), 3.70-3.68 (m, 6H), 3.63-3.61 (m, 2H), 3.40 (t, J=5.4 Hz, 2H), 2.20 (t, J=6.0 Hz, 1H)

Preparation of Compound 2l

After CBr$_4$ (21.4 g, 64.6 mmol) was dissolved in methylene chloride (MC, 100 mL) at 0° C. under nitrogen atmosphere, triphenylphosphine (16.9 g, 64.6 mmol) in MC (100 ml) and Compound 2k (10.3 g, 58.7 mmol) were added thereto, and the mixture was stirred at room temperature for 13 hours. After the reaction was completed, MC (300 mL) and distilled water (300 mL) were added thereto to extract an organic layer, and the extracted organic layer was dried over anhydrous sodium sulfate and concentrated under reduced pressure. The residue was subjected to column chromatography, thereby obtaining Compound 2l (12 g, 85%).

$^1$H NMR (400 MHz, CDCl$_3$) δ 3.83 (t, J=6.4 Hz, 2H), 3.72-3.67 (m, 6H), 3.48 (t, J=6.0 Hz, 2H), 3.40 (t, J=4.8 Hz, 2H)

Preparation of Compound 2m

After Compound 2l (1 g, 4.20 mmol) was dissolved in acetonitrile at room temperature under nitrogen atmosphere, N-Boc-hydroxylamine (643 mg, 4.82 mmol) and DBU (0.659 mL, 4.41 mmol) were added thereto, and the mixture was stirred at 60° C. for 13 hours. After the reaction was completed, MC (300 mL) and distilled water (300 mL) were added thereto to extract an organic layer, and the extracted organic layer was dried over anhydrous sodium sulfate and concentrated under reduced pressure. The residue was subjected to column chromatography, thereby obtaining Compound 2m (748 mg, 70%).

$^1$H NMR (400 MHz, CDCl$_3$) δ 7.55 (s, 1H), 4.05-4.03 (m, 2H), 3.76-3.74 (m, 2H), 3.74-3.69 (m, 6H), 3.42 (t, J=4.8 Hz, 2H), 1.49 (s, 9H). EI-MS m/z: 291 (M+)

Preparation of Compound 2n

After Compound 2m (200 mg, 0.688 mmol) was dissolved in methanol (5 mL), Pd/C (10%) (70 mg) was added thereto and stirred under hydrogen atmosphere for 3 hours. After the reaction was completed, the mixture was celite-filtered and concentrated under reduced pressure, thereby obtaining Compound 2n (180 mg, 98%).

$^1$H NMR (400 MHz, CDCl$_3$) δ 4.04-4.01 (m, 2H), 3.74-3.62 (m, 7H), 3.55 (t, J=5.2 Hz, 1H), 2.88 (t, J=5.2 Hz, 1H), 2.81 (t, J=5.2 Hz, 1H), 1.64 (s, 2H), 1.48 (s, 9H). EI-MS m/z: 265 (M+)

Preparation of Compound 2g

After Compound 2f (1.34 g, 1.066 mmol) and Compound 2n (384 mg, 1.28 mmol) were dissolved in DMF (10 mL) at 0° C. under nitrogen atmosphere, DIPEA (464 uL, 2.665 mmol) and PyBOP (832 mg, 1.599 mmol) were added thereto and stirred at room temperature for 4 hours. After the reaction was completed, ethylacetate (200 mL) and distilled water (300 mL) were added thereto. The organic layer obtained as described above was dried over anhydrous sodium sulfate and concentrated under reduced pressure. The residue was subjected to column chromatography, thereby obtaining Compound 2g (1.2 g, 75%).

EI-MS m/z: 1503 (M$^+$)

Preparation of Compound 2h

After Compound 2g (530 mg, 0.352 mmol) was dissolved in methanol (10 mL) at −10° C. under nitrogen atmosphere, LiOH (147 mg, 7.98 mmol) in water (8 mL) was slowly added thereto and stirred for 1 hour. After the reaction was completed, chloroform (200 mL) and distilled water (30 mL, pH 2) were added thereto. The organic layer obtained as described above was dried over anhydrous sodium sulfate and concentrated under reduced pressure. The residue was subjected to column chromatography, thereby obtaining Compound 2h (260 mg, 45%).

EI-MS m/z: 1349 (M$^+$)

Preparation of Compound 2i

After Compound 2h (260 mg, 0.192 mmol) was dissolved in methylene chloride (4 mL) and water (2 mL) at 0° C. under nitrogen atmosphere, 4M-HCl (in dioxane, 4 mL) was added thereto and stirred at 0° C. for 1 hour. After the reaction was completed, the resultant was concentrated under reduced pressure, thereby obtaining Compound 2i (210 mg, 85%).

EI-MS m/z: 1249 (M$^+$)

Preparation of Compound 3k

After 2-bromoethanol (1.92 mL, 27.037 mmol) was dissolved in acetonitrile (15 mL) at room temperature under nitrogen atmosphere, Boc-hydroxylamine (3.0 g, 22.531 mmol) and DBU (3.7 mL, 24.8 mmol) were added thereto, and the mixture was stirred at 40° C. for 24 hours. After the reaction was completed, ethylacetate (100 mL) and distilled water (100 mL) were added thereto to extract an organic layer, and the extracted organic layer was dried over anhydrous sodium sulfate and concentrated under reduced pressure. The residue was subjected to column chromatography, thereby obtaining Compound 3k (2.75 g, 69%).

$^1$H NMR (400 MHz, CDCl$_3$) δ 7.28 (s, 1H), 3.93-3.91 (m, 2H), 3.76-3.74 (m, 2H), 1.50 (s, 9H).

Preparation of Compound 3l

After Compound 3k (2.75 g, 15.697 mmol) was dissolved in THF (30 mL) at 0° C. under nitrogen atmosphere, TEA (3.3 mL, 23.518 mmol) and Ms$_2$O (3.28 g, 18.814 mmol) were added thereto, and the mixture was stirred at room temperature for 4 hours. After the reaction was completed, ethylacetate (200 mL) and distilled water (100 mL) were added thereto to extract an organic layer, and the extracted organic layer was dried over anhydrous sodium sulfate and concentrated under reduced pressure, thereby obtaining Compound 3l (3.83 g, 96%).

$^1$H NMR (400 MHz, CDCl$_3$) δ 7.37 (s, 1H), 4.48-4.46 (m, 2H), 4.13-4.09 (m, 2H), 3.11 (s, 3H), 1.50 (s, 9H).

Preparation of Compound 3m

After Compound 3l (3.83 g, 15.00 mmol) was dissolved in DMF (20 mL) at room temperature under nitrogen atmosphere, NaN$_3$ (1.95 g, 30.00 mmol) was added thereto, and the mixture was stirred at 60° C. for 13 hours. After the reaction was completed, ethylacetate (300 mL) and distilled water (300 mL) were added thereto to extract an organic layer, and the extracted organic layer was dried over anhydrous sodium sulfate and concentrated under reduced pressure. The residue was subjected to column chromatography, thereby obtaining Compound 3m (2.02 g, 67%).

$^1$H NMR (400 MHz, CDCl$_3$) δ 7.22-7.20 (m, 1H), 4.05-4.02 (m, 2H), 3.51-3.48 (m, 2H), 1.50 (s, 9H).

Preparation of Compound 3n

After Compound 3m (2.02 g, 9.98 mmol) was dissolved in methanol (30 mL), Pd/C (10%) (1.0 g) and 4M HCl in dioxane (2.5 mL) were added thereto and stirred under hydrogen atmosphere for 3 hours. After the reaction was completed, the mixture was celite-filtered and concentrated under reduced pressure, thereby obtaining Compound 3n (1.98 g, 93%).

$^1$H NMR (400 MHz, CDCl$_3$) δ 10.26 (s, 1H), 8.05 (s, 3H), 3.91-3.88 (m, 2H), 3.1-2.98 (m, 2H), 1.44 (s, 9H).

Preparation of Compound 3g

After Compound 2f (280 mg, 0.222 mmol) and Compound 3n (56 mg, 0.266 mmol) were dissolved in DMF (5 mL) at 0° C. under nitrogen atmosphere, DIPEA (58 uL, 0.334 mmol) and PyBOP (174 mg, 0.334 mmol) were added thereto and stirred at room temperature for 4 hours. After the reaction was completed, ethylacetate (100 mL) and distilled water (150 mL) were added thereto. The organic layer obtained as described above was dried over anhydrous sodium sulfate and concentrated under reduced pressure. The residue was subjected to column chromatography, thereby obtaining Compound 3g (221 mg, 69%).

EI-MS m/z: 1415 (M$^+$)

Preparation of Compound 3h

After Compound 3g (150 mg, 0.106 mmol) was dissolved in methanol (2 mL) at −10° C. under nitrogen atmosphere, LiOH (40 mg, 0.954 mmol) in water (2 mL) was slowly added thereto and stirred for 1 hour. After the reaction was completed, chloroform (150 mL) and distilled water (30 mL, pH 2) were added thereto. The organic layer obtained as described above was dried over anhydrous sodium sulfate and concentrated under reduced pressure. The residue was subjected to column chromatography, thereby obtaining Compound 3h (94 mg, 71%).

EI-MS m/z: 1261 (M$^+$)

Preparation of Compound 3i

After Compound 3h (90 mg, 0.071 mmol) was dissolved in methylene chloride (1 mL) at 0° C. under nitrogen atmosphere, trifluoroacetic acid (TFA, 0.2 mL) was added thereto and stirred at 0° C. for 3 hours. After the reaction was completed, the resultant was purified using Prep HPLC, thereby obtaining Compound 3i (47 mg, 52%).

EI-MS m/z: 1161 (M$^+$)

[Example 4] Preparation of Compound 4i

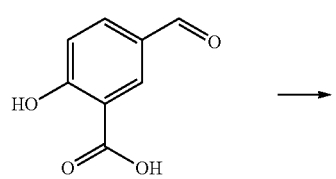

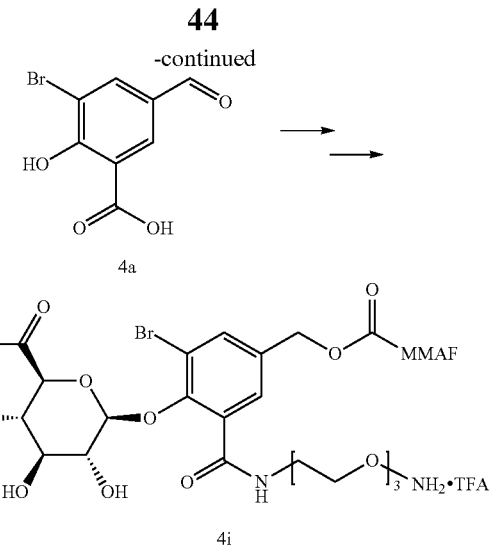

Preparation of 3-bromo-5-formylsalicylic Acid (Compound 4a)

After 5-formylsalicylic acid (1 g, 6.019 mmol) was dissolved in DMF at 0° C. under nitrogen atmosphere, N-bromosuccinimide (1.07 g, 6.109 mmol) was added thereto and the mixture was stirred at 70° C. for 3 hours. After the reaction was completed, ethylacetate (100 mL), 2N—HCl aqueous solution (2 mL), and distilled water (100 mL) were added thereto. The organic layer obtained as described above was dried over anhydrous sodium sulfate and concentrated under reduced pressure. The residue was subjected to column chromatography, thereby obtaining Compound 4a (1.2 g, 84%).

$^1$H NMR (400 MHz, DMSO-d$_6$) δ 9.64 (s, 1H), 8.19 (d, J=2.4 Hz, 1H), 8.00 (d, J=2.0 Hz, 1H), 3.16 (s, 1H)

Compound 4i was prepared using prepared 3-bromo-5-formylsalicylic acid (Compound 4a) by a method similar to methods of preparing Compounds 2i and 3i of Examples 2 and 3.

EI-MS m/z: 1328 (M+)

[Examples 5 to 7] Preparation of LCB14-0648, LCB14-0664, and LCB14-0663

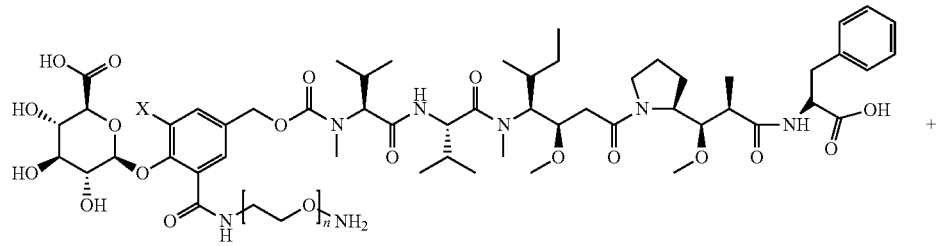

2i (X = H, n = 3)
3i (X = H, n = 1)
4i (X = Br, n = 3)

-continued

LCB14-0648 (X = H, n = 3)
LCB14-0664 (X = H, n = 1)
LCB14-0663 (X = Br, n = 3)

Compound C was prepared by a method disclosed in Korean Patent Laid-Open Publication No. 10-2014-0035393.

Preparation of LCB14-0648 (Example 5)

After Compound 2i (20 mg, 0.014 mmol) was dissolved in ethanol (0.7 mL) at room temperature under nitrogen atmosphere, Compound C (3.7 mg, 0.017 mmol) was added thereto, and the mixture was stirred at 45° C. for 2 hours. After the reaction was completed, LCB14-0648 (10.2 mg, 49%) was obtained using Prep HPLC.

EI-MS m/z: 1441 (M$^+$)

LCB14-0663 (Example 6) and LCB14-0664 (Example 7) were prepared by a method similar to the method of preparing LCB14-0648 (Example 5).

EI-MS of LCB14-0663: m/z: 1520 (M$^+$)
EI-MS of LCB14-0664: m/z: 1353 (M$^+$)

[Comparative Example 1] Preparation of Compound 5k

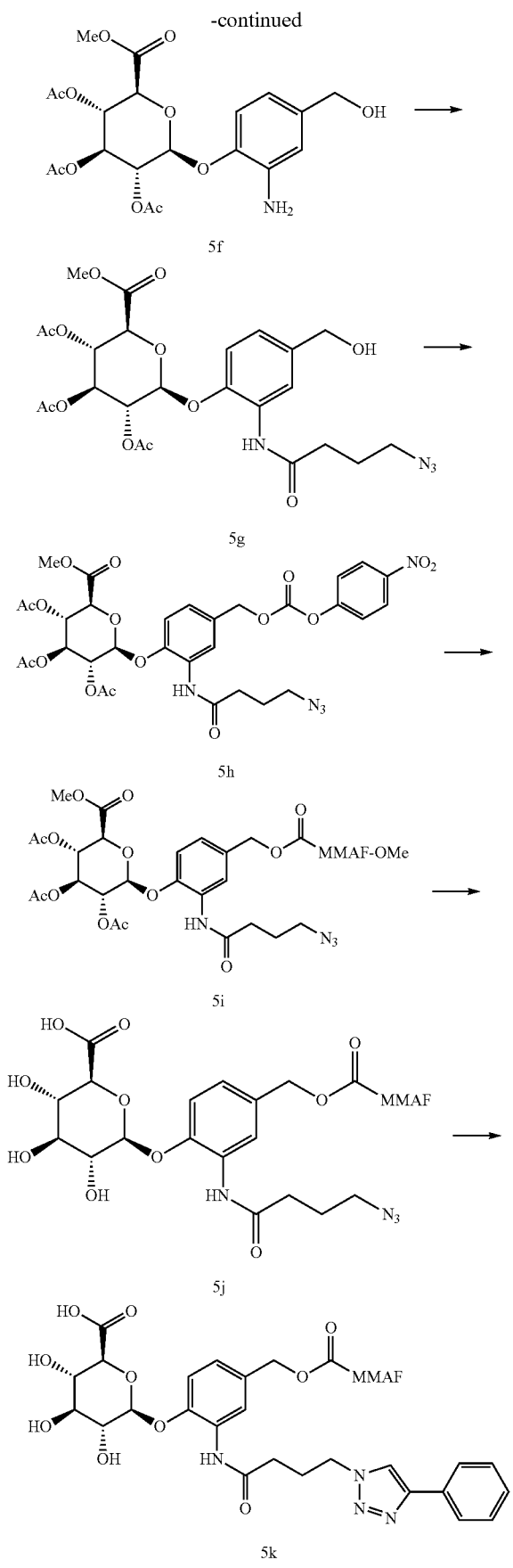

Preparation of Compound 5a

After ethyl 4-bromobutanoate (5.0 mL, 34.604 mmol) was dissolved in MeOH (75 mL) at room temperature under nitrogen atmosphere, sodium azide (4.5 g, 69.209 mmol) in water (25 mL) was added thereto and stirred at 85° C. for 8 hours. After the reaction was completed, the solvent was concentrated under reduced pressure, and chloroform (300 mL) and distilled water (200 mL) were added thereto. The organic layer obtained as described above was dried over anhydrous sodium sulfate and concentrated under reduced pressure. The residue was subjected to column chromatography, thereby obtaining Compound 5a (5.1 g, 94%).

$^1$H NMR (600 MHz, CDCl$_3$) δ 4.15 (q, J=7.2 Hz, 2H), 3.36 (t, J=7.2 Hz, 2H), 2.41 (t, J=7.2 Hz, 2H), 1.94-1.89 (m, 2H), 1.28 (t, J=8.4 Hz, 3H).

Preparation of Compound 5b

After Compound 5a (2.0 g, 12.725 mmol) was dissolved in MeOH (32 mL) at 0° C. under nitrogen atmosphere, KOH (3.56 g, 63.625 mmol) in water (26 mL) was slowly added thereto and stirred at room temperature for 6 hours. After the reaction was completed, the solvent was concentrated under reduced pressure, and chloroform (300 mL), 1N HCl (100 mL), and distilled water (100 mL) were added thereto. The organic layer obtained as described above was dried over anhydrous sodium sulfate and concentrated under reduced pressure. The residue was subjected to column chromatography, thereby obtaining Compound 5b (1.28 g, 78%).

$^1$H NMR (600 MHz, CDCl$_3$) δ 3.38 (t, J=7.2 Hz, 2H), 2.48 (t, J=7.2 Hz, 2H), 1.95-1.90 (m, 2H).

Preparation of Compound 5c

After Compound 5b (850 mg, 6.580 mmol) was dissolved in MeOH (10 mL) at 0° C. under nitrogen atmosphere, oxalyl chloride (1.1 mL, 13.160 mmol) and DMF (1 drop) were added thereto and stirred at room temperature for 6 hours. After the reaction was completed, the solvent was concentrated under reduced pressure, such that Compound 5c (965 mg, Qu) corresponding to a crude product was obtained and used in the next reaction without purification.

Preparation of Compound 5d

After 4-hydroxy-3-nitrobenzoic acid (5 g, 27.304 mmol) was dissolved in THF (120 mL) at 0° C. under nitrogen atmosphere, 1M BH3-THF complex (54.6 mL, 54.6 mmol) was added thereto and stirred at room temperature for 20 hours. After the reaction was completed, ethylacetate (200 mL), 0.5N HCl (20 mL), and distilled water (100 mL) were added thereto. The organic layer obtained as described above was dried over anhydrous sodium sulfate and concentrated under reduced pressure. The residue was subjected to column chromatography, thereby obtaining Compound 5d (4.20 g, 91%).

$^1$H NMR (600 MHz, CD3OD) δ 8.06 (d, J=1.2 Hz, 1H), 7.59 (dd, J=1.2, 7.8 Hz, 1H), 7.12 (d, J=8.4 Hz, 1H), 4.83 (s, 2H)

Preparation of Compound 5e

After Compound 5d (937 mg, 5.539 mmol) was dissolved in acetonitrile (15 mL) at room temperature under nitrogen atmosphere, and Compound 5c (2.0 g, 5.035 mmol), silver oxide (4.66 g, 20.108 mmol), and molecular sieve (2.0 g) were added thereto, and stirred at room temperature for 14 hours. After the reaction was completed, the mixture was celite-filtered, and the filtrate was concentrated under reduced pressure. The residue was subjected to column chromatography, thereby obtaining Compound 5e (1.0 g, 40%).

$^1$H NMR (600 MHz, CDCl$_3$) δ 7.81 (d, J=1.8 Hz, 1H), 7.54 (dd, J=1.8, 6.6 Hz, 1H), 7.37 (d, J=8.4 Hz, 1H), 5.37-5.27 (m, 3H), 5.20 (d, J=6.6 Hz, 1H), 4.72 (d, J=6.0 Hz, 2H), 4.21 (d, J=9.0 Hz, 1H), 3.75 (s, 3H), 2.12 (s, 3H), 2.06 (s, 3H), 2.05 (s, 3H), 2.04-2.02 (m, 1H).

Preparation of Compound 5f

After Compound 5e (900 mg, 6.35 mmol) was dissolved in ethylacetate (100 mL), platinum (IV) oxide (84.2 mg, 0.370 mmol) was added thereto and stirred at room temperature under hydrogen atmosphere for 3 hours. After the reaction was completed, the mixture was celite-filtered, and the filtrate was concentrated under reduced pressure, such that Compound 5f (700 mg, 83%) corresponding to a crude product was obtained and used in the next reaction without purification.

Preparation of Compound 5g

After Compound 5f (350 mg, 0.768 mmol) was dissolved in MC (10 mL) at 0° C. under nitrogen atmosphere, Compound 5c (136 mg, 0.921 mmol) and DIPEA (268 uL, 1.536 mmol) were added thereto and stirred at room temperature for 20 minutes. After the reaction was completed, ethylacetate (50 mL) and distilled water (50 mL) were added thereto. The organic layer obtained as described above was dried over anhydrous sodium sulfate and concentrated under reduced pressure. The residue was subjected to column chromatography, thereby obtaining Compound 5g (280 mg, 65%).

$^1$H NMR (600 MHz, CDCl$_3$) δ 8.37 (d, J=1.2 Hz, 1H), 8.00 (s, 1H), 7.07 (dd, J=1.8, 6.6 Hz, 1H), 6.93 (d, J=8.4 Hz, 1H), 5.43-5.28 (m, 3H), 5.06 (d, J=7.8 Hz, 1H), 4.63 (s, 2H), 4.19 (d, J=9.6 Hz, 1H), 3.76 (s, 3H), 3.44-3.41 (m, 2H), 2.56 (t, J=7.8 Hz, 2H), 2.17-2.00 (m, 12H). EI-MS m/z: 567 (M+)

Preparation of Compound 5h

After Compound 5g (250 mg, 0.441 mmol) was dissolved in DMF (4 mL) at 0° C. under nitrogen atmosphere, bis(4-nitrophenyl)carbonate (270 mg, 0.882 mmol) and DIPEA (115 uL, 0.661 mmol) were added thereto, and stirred at room temperature for 1 hour. After the reaction was completed, ethylacetate (50 mL) and distilled water (50 mL) were added thereto. The organic layer obtained as described above was dried over anhydrous sodium sulfate and concentrated under reduced pressure. The residue was subjected to column chromatography, thereby obtaining Compound 5h (290 mg, 90%).

$^1$H NMR (600 MHz, CDCl$_3$) δ 8.54 (d, J=1.8 Hz, 1H), 8.28-8.25 (m, 2H), 8.02 (s, 1H), 7.40-7.36 (m, 2H), 7.11 (dd, J=1.8, 6.6 Hz, 1H), 6.96 (d, J=8.4 Hz, 1H), 5.44-5.29 (m, 3H), 5.23 (s, 2H), 5.10 (d, J=7.8 Hz, 1H), 4.21 (d, J=9.6 Hz, 1H), 3.76 (s, 3H), 3.45-3.42 (m, 2H), 2.58 (t, J=7.2 Hz, 2H), 2.11-2.00 (m, 12H). EI-MS m/z: 732 (M+)

Preparation of Compound 5i

After Compound 5h (250 mg, 0.341 mmol) was dissolved in DMF (4 mL) at room temperature under nitrogen atmosphere, MMAF-OMe (255 mg, 0.341 mmol) was added thereto, and then, the resultant was treated with HOBT (9 mg, 0.068 mmol), pyridine (1.2 mL), and DIPEA (60 uL, 0.341 mmol). The obtained mixture was stirred at room temperature for 2 days. After the reaction was completed, ethylacetate (50 mL), 2N HCl (5 mL), and distilled water (50 mL) were added thereto. The organic layer obtained as described above was dried over anhydrous sodium sulfate and concentrated under reduced pressure. The residue was subjected to column chromatography, thereby obtaining Compound 5i (340 mg, 74%).

EI-MS m/z: 1339 (M+)

Preparation of Compound 5j

After Compound 5i (210 mg, 0.156 mmol) was dissolved in methanol (2 mL) at 0° C. under nitrogen atmosphere, LiOH.H$_2$O (66 mg, 1.560 mmol) in water (2 mL) was added thereto. The obtained mixture was stirred at room temperature for 1.5 hours. After the reaction was completed, chloroform (50 mL), methanol (5 mL), distilled water (50 mL), and 0.5N HCl (5 mL) were added thereto. The organic layer obtained as described above was dried over anhydrous sodium sulfate and concentrated under reduced pressure. The residue was subjected to column chromatography, thereby obtaining Compound 5j (107 mg, 57%).

EI-MS m/z: 1184 (M+)

Preparation of Compound 5k

After Compound 5j (10 mg, 0.008 mmol) and phenylacetylene (0.92 uL, 0.008 mmol) were dissolved in ethanol (150 ul) and water (10 ul) at room temperature under nitrogen atmosphere, 0.1M CuSO$_4$ aqueous solution (10 ul) and 1.0M sodium ascorbate aqueous solution (10 ul) were added thereto. The obtained mixture was stirred at room temperature for 5 hours. After the reaction was completed, ethylacetate (10 mL) and distilled water (5 mL) were added thereto. The organic layer obtained as described above was dried over anhydrous sodium sulfate and concentrated under reduced pressure. The residue was subjected to column chromatography, thereby obtaining Compound 5k (5 mg, 46%).

EI-MS m/z: 1286 (M+)

[Example 8] Preparation of Compound 6e

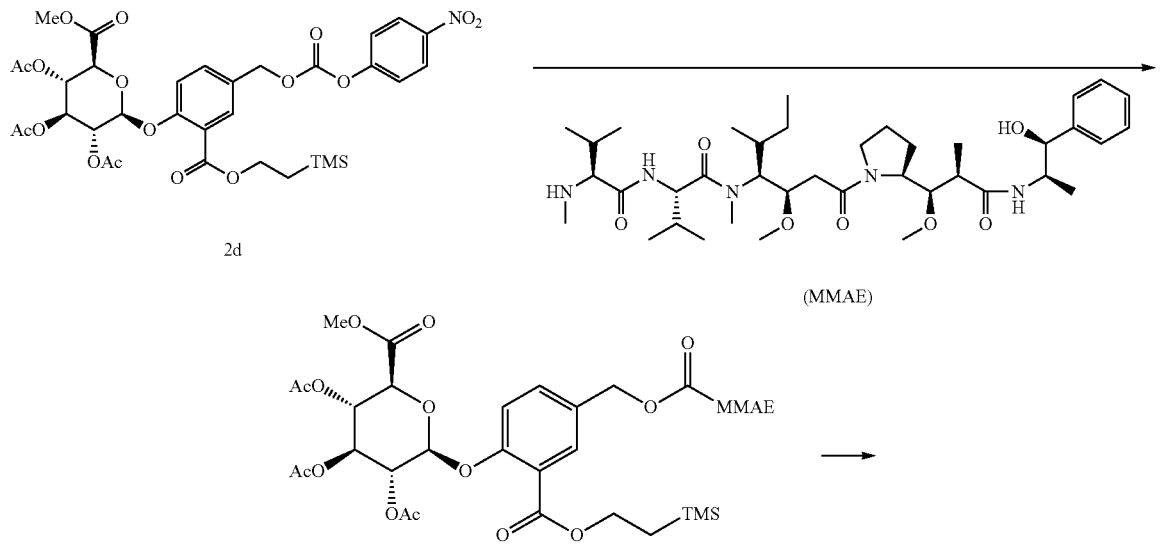

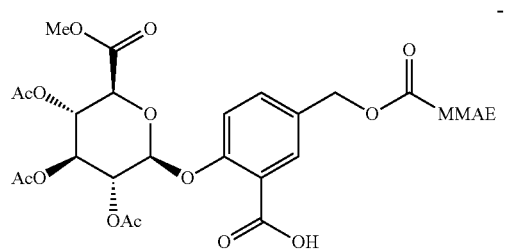

6b

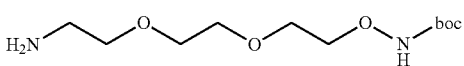

2n

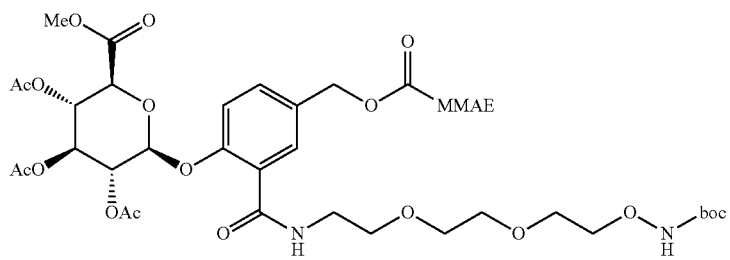

6c

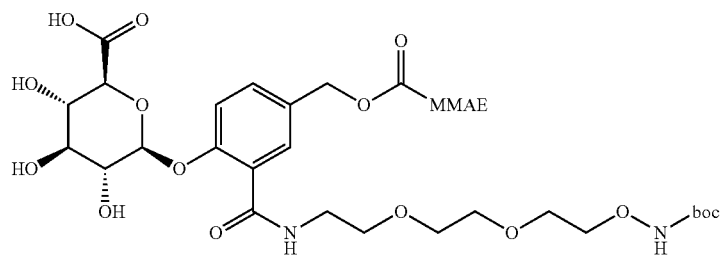

6d

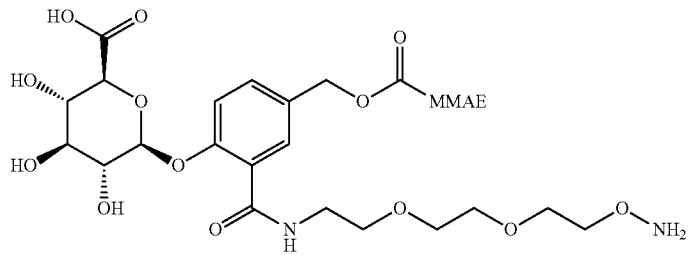

6e (HCl salt)

Preparation of Compound 6a

After Compound 2d (229 mg, 0.30 mmol) was dissolved in DMF (2 mL) at room temperature under nitrogen atmosphere, MMAE (1.34 g, 1.80 mmol) was added thereto, and then, the resultant was treated with HOBT (8.2 mg, 0.06 mmol), pyridine (0.8 mL), and DIPEA (56 uL, 0.29 mmol). The mixture was stirred at room temperature for 12 hours. After the reaction was completed, ethylacetate (100 mL) and distilled water (100 mL) were added thereto. The organic layer obtained as described above was dried over anhydrous sodium sulfate and concentrated under reduced pressure. The residue was subjected to column chromatography, thereby obtaining Compound 6a (239 mg, 65%).

EI-MS m/z: 1328 (M+)

Preparation of Compound 6b

After Compound 6a (239 mg, 0.18 mmol) was dissolved in THF (5 mL) at 0° C. under nitrogen atmosphere, tetrabutylammonium fluoride (1M in THF) (540 uL, 2.50.58 mol) was added thereto and stirred at room temperature for 3 hours. After the reaction was completed, methylene chloride (100 mL) and distilled water (100 mL) were added thereto. The organic layer obtained as described above was dried over anhydrous sodium sulfate and concentrated under reduced pressure. The residue was subjected to column chromatography, thereby obtaining Compound 6b (212 mg, 95%).

EI-MS m/z: 1228 (M+)

Preparation of Compound 6c

After Compound 6b (200 mg, 0.16 mmol) and Compound 2n (51 mg, 0.19 mmol) were dissolved in DMF (4 mL) at 0° C. under nitrogen atmosphere, DIPEA (42 uL, 0.32 mmol) and PyBOP (126 mg, 0.24 mmol) were added thereto and stirred at room temperature for 4 hours. After the reaction was completed, ethylacetate (100 mL) and distilled water (100 mL) were added thereto. The organic layer obtained as described above was dried over anhydrous sodium sulfate and concentrated under reduced pressure. The residue was subjected to column chromatography, thereby obtaining Compound 6c (142 mg, 60%).

EI-MS m/z: 1474 (M+)

Preparation of Compound 6d

After Compound 6c (142 mg, 0.09 mmol) was dissolved in methanol (2 mL) at −20° C. under nitrogen atmosphere, LiOH (36 mg, 0.86 mmol) in water (2 mL) was slowly added thereto and stirred at 0° C. for 1 hour. After the reaction was completed, chloroform (100 mL), distilled water (50 mL), and 2N—HCl aqueous solution (2 mL) were added thereto. The organic layer obtained as described above was dried over anhydrous sodium sulfate and concentrated under reduced pressure. The residue (6d, 128 mg, 99%) was used in the next reaction without purification.

EI-MS m/z: 1334 (M+)

Preparation of Compound 6e

After Compound 6d (105 mg, 0.08 mmol) was dissolved in methylene chloride (3 mL) at −20° C. under nitrogen atmosphere, 4M-HCl (in dioxane, 1 mL) was added thereto and stirred at 0° C. for 1 hour. After the reaction was completed, the resultant was concentrated under reduced pressure. The residue was purified using preparative HPLC, thereby obtaining Compound 6e (47 mg, 46%).

EI-MS m/z: 1234 (M+)

[Experimental Example 1] Responsiveness Comparison Test with Respect to β-Glucuronidase In order to compare responsiveness of Compound 1k of Example 1 and Compound 5k of Comparative Example 1 to β-glucuronidase with each other, comparison test was performed as follows.

Compound 1k of Example 1 and Compound 5k of Comparative Example 1 were each prepared as 500 μM and 50 μM DMSO stock solutions. Reaction solutions in which 880 μL of phosphate buffer saline (PBS) solution and 100 μL of Compound 1k and Compound 5k stock solutions were mixed with each other, respectively, were prepared (final concentrations thereof were 50 μM and 5 μM, respectively). After 20 μL of E. coli β-glucuronidase enzyme (1 mg/ml, Sigma: E.C.3.2.1.31 Type IX-A; 1 mg/mL in PBS; 3.6 μg, 13 μmol) was added to the reaction solutions, reactions were initiated in a constant temperature water bath at 37° C. 100 μL of the mixed solutions were dispensed at 0 min, 25 min, 60 min, and 90 min, respectively, and 200 μL of acetonitrile was added thereto. MMAF released from each of the supernatants obtained by performing centrifugation (4° C., 15 min, 14000 rpm) on the mixture samples was quantitatively analyzed using LC-MS/MS (the experiment was performed by a method similar to a method disclosed in US2012-0107332).

The test results were illustrated in FIG. 2, and it was confirmed from FIG. 2 that MMAF was significantly rapidly released from each Compound 1k of Example 1 and Compound 5k of Comparative Example 1 through a 1,6-elimination reaction after enzyme reactions by β-glucuronidase (Ref. US2112-0107332).

[Experimental Example 2] Plasma Stability Comparison Test

In order to compare plasma stability of Compound 1k of Example 1 and Compound 5k of Comparative Example 1 in a mouse with each other, a comparison test was performed as follows.

10 μL of Compound 1k and 5k solutions dissolved in DMSO at 5 mM were each mixed with 990 μL of blank plasma, thereby preparing 50 μM samples for confirming stability in plasma. The plasma solutions mixed with the compounds were reacted at 37° C. for 6 days. During the reaction for 6 days, 100 μL of the solutions were subdivided at each time (0, 1, 2, 3, and 6 days) and mixed with 200 μL of acetonitrile containing internal standard for precipitation of plasma protein after the reaction was terminated. The supernatants obtained by performing centrifugation (4° C., 15 min, 14000 rpm) on the mixture samples were quantitatively analyzed using LC-MS/MS (the experiment was performed by a method similar to a method disclosed in Journal of Chromatography B, 780 (2002) 451-457).

A result obtained by confirming a content of each Compound 1k of Example 1 and Compound 5k of Comparative Example 1 using LS-MS/MS was illustrated in FIG. 3 and Table 1, and as a result, stability of Compound 5k of Comparative Example 1 and stability of Compound 1k of Example 1 were 14% and 80% at 1 day, respectively, such that stability of Compound 1k of Example 1 in mouse plasma was significantly excellent as compared to Compound 5k of Comparative Example 1.

TABLE 1

|  | Compound 1k of Example 1 | Compound 5k of Comparative Example 1 |
| --- | --- | --- |
| Linker | Glucuronide | Glucuronide |
| Plasma Stability (in mouse) | 80% Stability (@7 days) | 14% Stability (@1 day) |
| Result | Stable | Unstable |

[Experimental Example 3] Plasma Stability Test

In order to confirm stability in various plasmas using LCB14-0648 (Example 5), LCB14-0664 (Example 6), and LCB14-0663 (Example 7), which were compounds prepared in Examples 5 to 7, plasma stability test was performed by the same method as in Experimental Example 2, and the results were illustrated in FIGS. 4 to 6.

It was confirmed that LCB14-0648 (Example 5), LCB14-0664 (Example 6), and LCB14-0663 (Example 7), which were compounds prepared in Examples 5 to 7, were all stable in mouse, rat, dog, and human plasmas up to 7 days.

Examples 9 to 11: Preparation of Antibody-Drug Conjugate (ADC)
[Example 9] Preparation of Herceptin (LC)-Glucuronide Linker-MMAF (Hereinafter, Referred to as 'LCB14-0109' or 'ADC109')
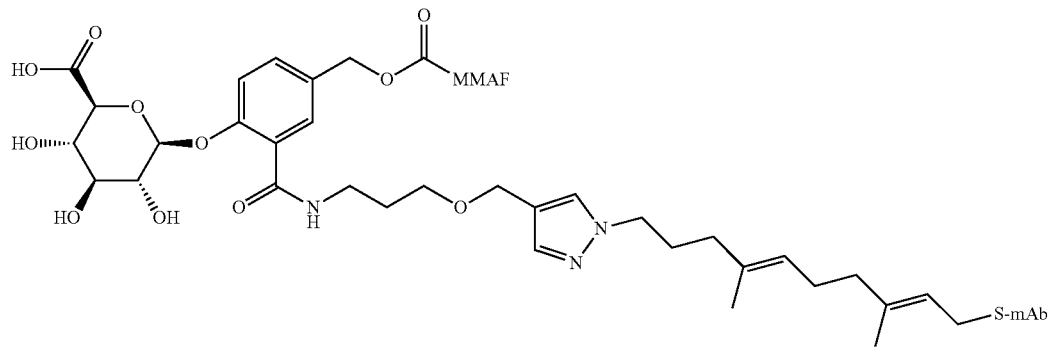
LCB14-0109 was prepared similarly to LCB14-0105 using a method disclosed in US2012/0308584.
[Example 10] Preparation of Herceptin (LC)-Glucuronide Linker-MMAF (Hereinafter, Referred to as 'LCB14-0110' or 'ADC110') (FIG. 7)
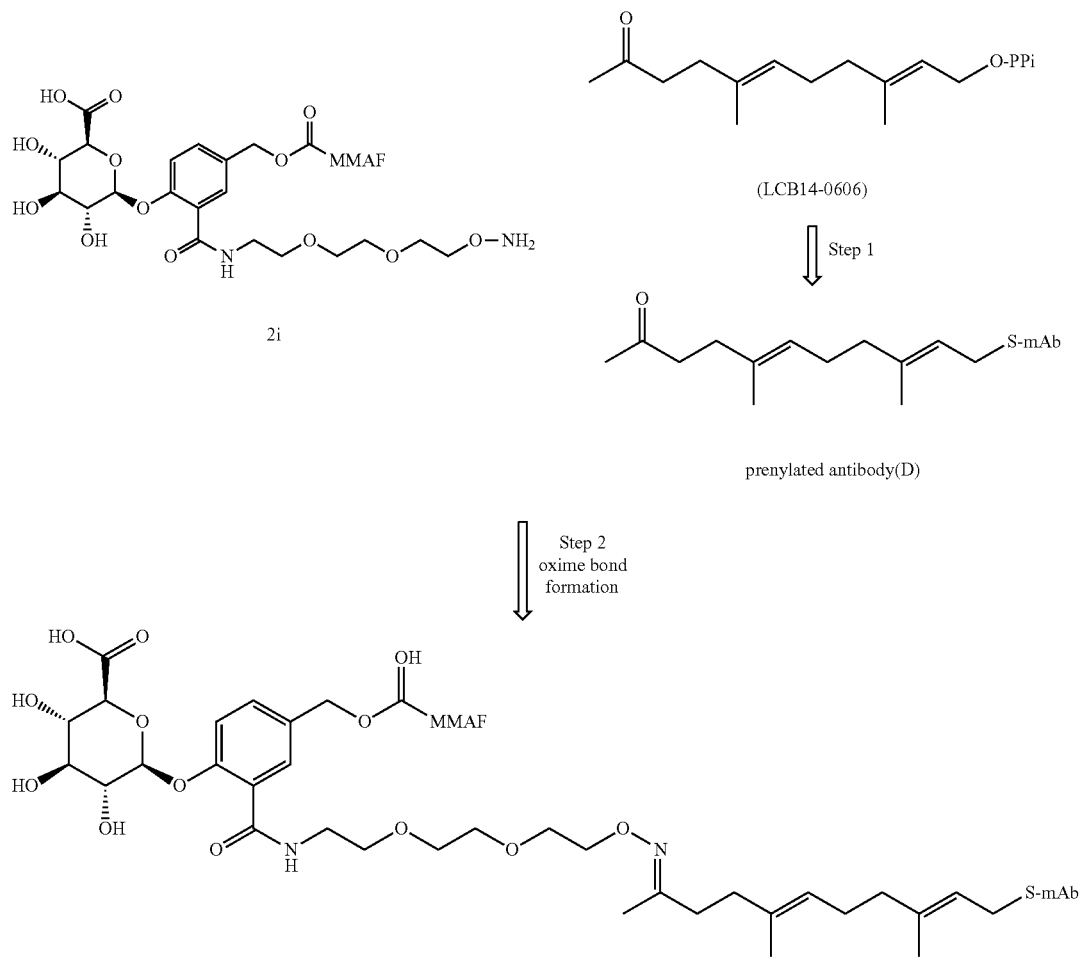

LCB14-0606 was prepared by a method disclosed in Korean Patent Laid-Open Publication No. 10-2014-0035393.

Step 1 (Prenylated Antibody, D) Preparation of Substrate (D) Disclosed in US2012/0308584

A prenylation reaction mixture of an antibody was prepared and reacted at 30° C. for 12 hours. The reaction mixture was composed of a buffer solution (50 mM Tris-HCl (pH7.4), 5 mM $MgCl_2$, 10 μM $ZnCl_2$, 5 mM DTT) containing 24 μM antibody, 200 nM FTase (Calbiochem #344145), and 1 mM LCB14-0606 (in house, US2012/0308584). After the reaction was completed, a prenylated antibody was purified by G25 Sepharose column on an AKTA purifier (GE healthcare), which was equilibrated with PBS buffer solution. The prenylated antibody (final concentration: 12 μM) was treated with 1 mM $CuSO_4$ and reacted at 30° C. for 3 hours to thereby be reoxidized. After the reaction was completed, 2 mM (final concentration) EDTA was added thereto and kept at 30° C. for 30 minutes while being weakly stirred. In order to remove an excessive amount of small molecules used in the reaction, the resultant was purified by FPLC.

Step 2 (Method of Preparing LCB14-0110)

An oxime bond formation reaction mixture between the prenylated antibody (A) and toxin (3 1) was prepared by mixing 100 mM Na-acetate buffer (pH 4.5, 10% DMSO), 12 μM antibody, and 360 μM LCB14-0645 (in house) and weakly stirred at 30° C. After the reaction was performed for 24 hours, FPLC (AKTA purifier, GE healthcare) was performed in order to remove an excessive amount of small molecules used in the reaction, such that the excessive amount of small molecules was removed, and a protein fraction was collected to thereby be concentrated.

[Example 11] Preparation of Herceptin (LC)-Glucuronide Linker-MMAE (Hereinafter, Referred to as 'LCB14-0113' or 'ADC113')

LCB14-0113 (ADC113) was prepared using the prepared Compound 6e by a method similar to a preparation process of Example 10.

[Experimental Example 4] Plasma Stability Test of ADC

Based on the result that LCB-SI (Compound 1k of Example 1) was more stable in the plasma as compared to SG-SI (Compound 5k of Comparative Example 1) through model study using Compound 1k of Example 1 and Compound 5k of Comparative Example 1 in Experimental Example 2, stability results of ADC(s) (LCB14-0109 (ADC109) prepared in Example 9 and LCB14-0110 (ADC110) prepared in Example 10) obtained by binding an antibody and a drug were compared with each other.

Plasma stability of the ADC(s) (LCB14-0109 (ADC109) prepared in Example 9 and LCB14-0110 (ADC110) prepared in Example 10) prepared as described above was evaluated by the following method, and the results were illustrated in FIGS. 8 and 9.

(Plasma Stability Test Method of ADC)

The ADC was prepared at a concentration of 0.5 mg/ml (MMAF concentration: 6.8 μM) in blank plasma and incubated at 37° C. A 50 μl aliquot of sample was taken at 0, 1, 2, and 7 days, and stored at −70° C. before analysis. An amount of toxin (free MMAF) released from the sample was measured, thereby evaluating plasma stability of the ADC.

(Stability Analysis Using LC-MS/MS)

A 20 mM MMAF stock solution was prepared using DMSO, and 0.02, 0.04, 0.2, 0.4, 2, 4, 20, 40, and 80 μM MMAF standard solutions were prepared by diluting the MMAF stock solution with acetonitrile. Each of the MMAF standard solutions was diluted 20 times with blank plasma to thereby be used as a sample for calibration curve.

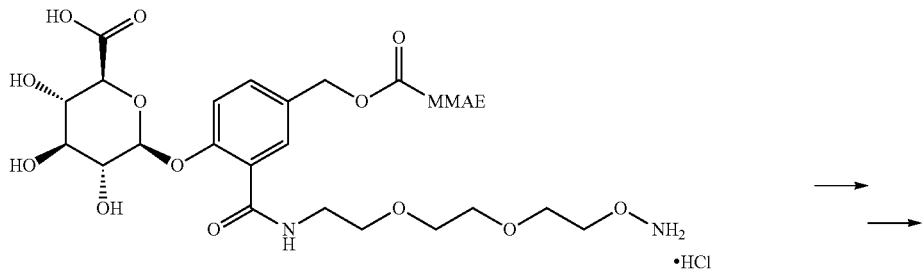

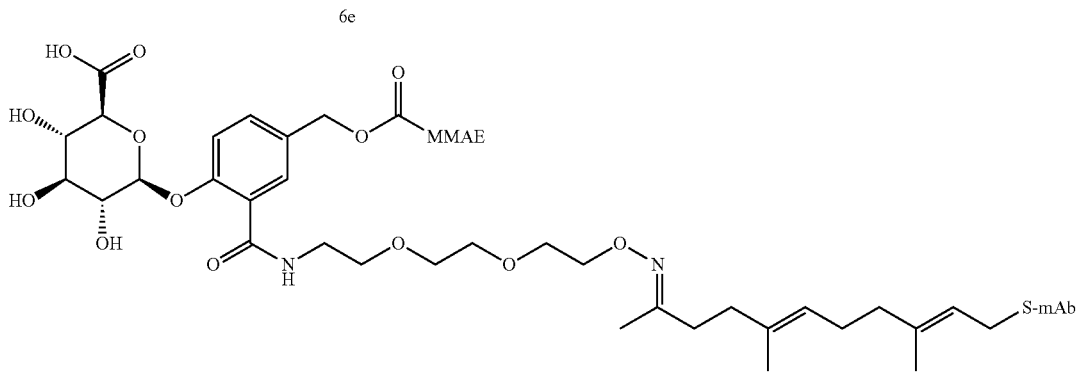

LCB14-0113

100 μl of acetonitrile containing internal standard (0.2 μM MMAE) was added to and mixed with 50 μl of the sample for the calibration curve and stability, followed by centrifugation. 80 μl of supernatant was extracted and mixed with mobile phase A (80 μl) and the mixture was analyzed using LC-MS/MS. 1200 HPLC (Agilent Technologies), API4000 (AB SCIEX), and Analyst software (Version 1.6.1) were used for LC-MS/MS analysis. 5 μl of sample was injected into an ODP2 HP-2D (2 □ 150 mm, 5 μm, Shodex) column and separated with a composition of 1 mM ammonium formate (mobile phase A, 40%) and 90% acetonitrile in 0.1% formic acid (mobile phase B, 60%). MMAF was measured in ESI+mode at m/z 732.6/170.1 (parent/daughter ion).

In the ADC prepared in Example 9 of the present invention, LCB14-0109 (ADC109), the amount of free MMAF was less than 0.5% even at 7 days, such that a significantly stable experimental result was obtained. Further, it may be appreciated that a half-life of the ADC prepared in Example 10 of the present invention, LCB14-0110 (ADC110) was 7 days or more (in mouse, rat, dog, and human plasmas), such that LCB14-0110 (ADC110) was significantly stable.

[Experimental Example 5] Anti-Proliferation Assay of ADC

Anti-cell proliferation activities of antibodies, a drug, and ADC(s) illustrated in the following Table 2 on cancer cell lines were measured.

As the cancer cell lines, commercialized human breast cancer cell lines MCF-7 (HER2-negative or -normal) and SK-Br3 (HER2 positive), and a commercialized ovarian cancer cell lines SK-OV3 (HER2 positive) were used. As the drug, MMAF was used. As the antibody, commercialized Herceptin-G7-CVIM (LC) and Herceptin-G7-CVIM (HC) were used. As the ADC, LCB14-0109 (ADC109) of Example 8 and LCB14-0110 (ADC110) of Example 9 were used.

After each of the cancer cell lines was seeded in a 96-well plate at 10,000 cells/each well and cultured for 24 hours, the antibody and ADC were treated at a concentration of 0.01563~2 μg/ml (2 times serial dilution), and the drug was treated at a concentration of 4~500 nM (2 times serial dilution). After 72 hours, the numbers of living cells were quantified using a Sulforhodamine B (SRB) dye.

TABLE 2

|  |  | $IC_{50}$ (μg/ml) | | |
| --- | --- | --- | --- | --- |
|  |  | Breast Cancer Cell Line MCF-7 | Ovarian Cancer Cell Line SK-OV3 | Breast Cancer Cell Line SK-Br3 |
| Drug | MMAF (nM) | 142.4 | 227.0 | 135.7 |
| Antibody | Herceptin-G7-CVIM(LC) | 1.54 | >2 | 1.98 |
|  | Herceptin-G7-CVIM(HC) | >2 | >2 | 1.53 |
| ADC | LCB14-0109 (ADC109, Example 9) | >2 | >2 | 0.078 |
|  | LCB14-0110 (ADC110, Example 10) | >2 | 0.315 | 0.14 |

It may be confirmed that efficacy of LCB14-0109 (ADC109) and LCB14-0110 (ADC110) corresponding to the antibody-drug conjugates, efficacy in SK-Br3 was equal to or more than 10 times that of the antibody, such that efficacy of the ADC(s) was more excellent than that of the antibody itself.

[Experimental Example 6] In Vivo Efficacy Evaluation

In Vivo Anti-tumor Efficacy Evaluation of LCB14-0109 (ADC109) and LCB14-0110 (ADC110)

Efficacy of a drug depending on single-dose or multi-dose administration was evaluated using an orthotopic model.

A human breast carcinoma cell line BT-474 was purchased from Korea Cell Line Bank and cultured using RPMI 1640 (10% FBS, 1% penicillin/streptomycin) in an incubator (37° C., 5% $CO_2$) in which a constant temperature and humidity was maintained. As experimental animals, Balb/c-nu female mice (6 weeks old) purchased from Japan SLC were used, and after acclimation period of 1 week, 17b-estradiol pellet (1.72 mg/pellet, Innovative Research of America, Sarasota, Fla.) was subcutaneously administered. After 6 days, BT474 cell ($5 \times 10^6$ cells in 100 μL) was suitably mixed with 50% PBS/50% phenol red-free Matrigel (Becton Dickinson Bioscience) and injected into the second mammary fat pad, thereby making orthotopic models. A tumor size was measured twice per a week, and a volume was calculated by ½ [length (mm)]×[width (mm)]$^2$. The mice were grouped so as to have an average tumor volume of 100 mm$^3$ in each group after 3 weeks from cell injection, and then used in the experiment. Herceptin manufactured by Roche was purchased and used, and various ADCs were produced by the present inventors, and administered once a week or one time to the experimental animals through the lateral tail vein.

1) Tumor Volume Observation Depending on BT474 Breast Tumor Orthotopic Model-QW Dose (QW=Once a Week)

A total of 5 animal groups, that is, a vehicle administration group, a Herceptin (5 mg/kg) administration group and ADC109 (0.1, 1, 5 mg/kg) administration groups were used, and a total of 11 mice were used per group. The drug was administered once a week for a total of three times through the tail vein, and as a result, in the Herceptin (5 mg/kg) administration group, tumor growth was partially inhibited until an end point in time of the experiment. This result was similar to that in the ADC109 (1 mg/Kg) administration group. On the contrary, in the ADC109 (5 mg/kg) administration group, tumor growth inhibition was initiated after 4 days of the first administration, and tumor regression was observed within the experimental period of 2 weeks (FIG. 10).

2) Body Weight Change Observation Depending on LCB14-0109 (ADC109) Dose in BT474 Breast Cancer Orthotopic Model The drug was administered by the same method as in 1), and a body weight change depending on an ADC109 dose was observed. As a result, during the entire experimental period, a body weight change was not observed, and the result was illustrated in the following Table 3.

TABLE 3

Body Weight Change

| | Experimental period | | | | | | |
|---|---|---|---|---|---|---|---|
| | Day 1 | Day 4 | Day 7 | Day 10 | Day 14 | Day 17 | Day 21 |
| Vehicle | 20.8 | 21.7 | 22.2 | 21.9 | 21.7 | 21.3 | 22.0 |
| Herceptin (5 mg/kg) | 20.7 | 22.1 | 22.1 | 21.9 | 21.1 | 21.4 | 22.5 |
| ADC109 (0.1 mg/kg) | 20.9 | 22.3 | 22.8 | 22.4 | 22.8 | 21.0 | 23.1 |
| ADC109 (1 mg/kg) | 20.8 | 21.3 | 21.9 | 22.1 | 21.9 | 22.9 | 21.8 |
| ADC109 (5 mg/kg) | 20.6 | 21.2 | 21.9 | 21.8 | 21.5 | 22.2 | 21.5 |

3) Efficacy Evaluation Depending on Multi-Dose Administration

In order to evaluate drug efficacy of Herceptin, ADC109, and ADC110 in a human epidermal growth factor receptor 2 (Her2)-positive human breast cancer orthotopic model depending on multi-dose administration, an experiment was performed. A total of 4 animal groups, that is, a Vehicle administration group, a Herceptin (5 mg/kg) administration group, an ADC109 (5 mg/kg) administration group, and an ADC110 (5 mg/kg) administration group were used, a total of 11 BT474 orthotopic mice were used per group, and the drugs were administered once a week for a total of 4 times through the tail vein. In the Herceptin (5 mg/kg) administration group, tumor growth was partially inhibited until an end point in time of the experiment, but in ADC109 and ADC110 administration groups, similarly to each other, drug response was achieved after 4 days of the first administration, tumor was perfectly regressed after 10 days, and tumor regression was maintained without regrowth until the end point in time of the experiment (FIG. 11). It was observed that weight changes and dead animals observed during the entire experimental period were irrelevant to the administered drugs.

4) Efficacy Evaluation Depending on Single-Dose Administration

In order to evaluate drug efficacy of Herceptin, ADC109, and ADC110 in Her2-positive human breast cancer orthotopic model depending on single-dose administration, an experiment was performed. Animal groups were the same as those in the multi-dose administration model, a total of 4 BT474 orthotopic mice were used per group, the drugs were administered once at an initiation point in time of the experiment through the tail vein, and only observation was performed during an experiment period of 5 weeks without additional drug administration. In the ADC109 and ADC110 administration groups, the responses to tumor growth were similar to those in the multi-dose administration experiment, and in the case of the Herceptin administration group, a tumor regrowth phenomenon was observed from 10 days after a single-dose administration. However, in the ADC109 and ADC 110 administration groups, tumor regression was maintained until the end point in time of the experiment (FIG. 12). It was observed that weight changes and dead animals observed during the entire experimental period were irrelevant to the administered drugs.

[Experimental Example 7] Plasma Stability Test of ADC

Plasma stability was evaluated on the ADC110 of Example 10, the ADC113 of Example 11, and Kadcyla by the following method, and the results were illustrated in FIGS. 13 to 15.

(In Vitro Plasma Stability Test Method of ADC)

The ADC was diluted at a concentration of 1 mg/ml using PBS and mixed with plasma so as to have a final concentration of 0.16 mg/ml. The mixture was cultured at 37° C., a plasma sample was collected at predetermined times (1 day, 3 days, 5 days, and 7 days), and only an antibody was recovered from the plasma sample using protein A magnetic beads. A test material obtained from a supernatant obtained by washing the magnetic beads with a solution containing 30% acetonitrile and 1% formic acid was analyzed using LC-MS, and a drug-antibody ratio (DAR) change was observed. In the case of Kadcyla (T-DM1), which was a control material, only stability thereof in PBS was observed. As a result, it may be appreciated that the ADC110 of Example 10 and the ADC113 of Example 11 were significantly stable unlike the result of Kadcyla (T-DM-1) that it was unstable even in PBS.

[Experimental Example 8] In Vivo Pharmacokinetics (PK) Evaluation

1) In Vivo Mouse PK Profile

In order to confirm pharmacokinetics of a total antibody at the time of intravenously administering a single dose of Herceptin, ADC109, and ADC110 to an ICR mouse, an experiment was performed as follows. The test materials, that is, Herceptin (G1), ADC109 (G2), and ADC110 (G3) were intravenously administered to ICR male mice, respectively (dose: 2.5 mg/kg). At the time of blood collecting, 50 uL of blood was collected from the retro-orbital vein using a capillary tube coated with sodium-heparin at predetermined times (15 minutes, 1 hour, 2 hours, 4 hours, 6 hours, 1 day, 2 days, 3 days, 7 days, 10 days, and 14 days after administration). The collected blood was transferred to a 1.5 ml PE tube (Denvil, USA) and stored in an ice bath, and plasma obtained by centrifuging the stored blood at 14,000 rpm for 5 minutes within 1 hour after storage was stored in a deep freezer set to −70° C. until analysis. A test material in the mouse plasma was measured in the inside using an enzyme-linked immunosorbent assay (ELISA) analysis. Pharmacokinetics were analyzed by non-compartment analysis using Phoenix™ WinNonlin® (ver. 6.3, Pharsight), and area under the plasma concentration-time curves (AUC), maximum blood concentrations ($C_{max}$), half-lives ($t_{1/2}$), clearances (CL) and volumes of distribution (Vss) of FIG. 16 were calculated.

After administering the test material, analysis material was detected in the mouse plasma up to 14 days in all of the test groups. In all of the test groups, there was no large difference (2 times or more) in a PK parameter between the groups. However, even though the same dose was administered, in the case of ADC109 and ADC110, exposure was low as compared to Herceptin. Since ADC109 and ADC110 were antibody-drug conjugates (ADCs) unlike Herceptin, the result as described above is due to a difference in binding affinity to anti-human IgG (Fab specific or Fc specific) antibody used in the ELISA analysis.

In the test group G1 (Herceptin), $AUC_{INF}$ of Herceptin was 356.00 day*μg/ml, $C_0$ value was 39.20 μg/ml, CL was 7.04 mL/day/Kg, Vss was 186.00 mL/Kg, $T_{1/2}$ was 18.40 days, which were similar to those in PK profile in document. Further, in the test group G2 (ADC109), $AUC_{INF}$, $C_0$, CL, Vss, and $T_{1/2}$ values were 235.55 day*μg/ml, 31.56 μg/ml, 11.25 mL/day/Kg, 239.28 mL/Kg, and 15.04 days, respectively, and in the test group G3 (ADC110), $AUC_{INF}$, $C_0$, CL, Vss, and $T_{1/2}$ values were 373.60 day*μg/ml, 35.11 μg/ml, 7.49 mL/day/Kg, 326.68 mL/Kg, and 35.72 days, respectively. These results were similar to those in the test group G1 (Herceptin), but exposure was slightly low.

2) In Vivo Rat PK Test

In order to confirm pharmacokinetics of test materials at the time of intravenously administering single dose of Herceptin and ADC110 to a rat, an experiment was performed as follows. The test materials, Herceptin and ADC110 were intravenously administered to female rats, respectively (Dose: 3.0 mg/kg). 0.4 mL of blood was collected from the jugular vein using a 1 mL syringe (25 Gauge) treated with heparin (85 IU/mL, 35 uL) at predetermined times (3 minutes, 1 hour, 3 hours, 6 hours, 1 day, 2 days, 3 days, 4 days, 7 days, 9 days, 14 days, 17 days, 21 days, and 28 days after administration), put into a micro tub, treated with a roll mixer for several minutes, and then centrifuged at 14,000 rpm for 5 minutes, thereby separating plasma. The separated plasma was put into a micro tube and stored in a deep freezer until analysis. The test materials in the plasma were measured using LC-MS. PK analysis was performed by compartment model 2 using Phoenix™ WinNonlin® (ver. 6.3, Pharsight), and a drug-antibody ratio was quantified by LC-MS/MS after separating ADC110 using protein A beads. The results were illustrated in FIGS. 17 to 19, respectively. In addition, area under the plasma concentration-time curves (AUC), maximum blood concentrations ($C_{max}$), half-lives ($t_{1/2}$), clearances (CL), distribution half-lives (Alpha HL), secretion half-lives (beta HL), volumes of distribution (V1), and volumes of distribution (Vss) of Table 4 were calculated.

In the case of ADC110, AUC was 684.83 µg*day/mL, CL was 4.38 mL/day/Kg, Cmax value was 92.18 µg/ml, Vss was 43.83 mL/Kg, and $T_{1/2}$ was 8.55 days, and in the case of Herceptin, AUC was 622.87 µg*day/mL, CL was 4.87 mL/day/Kg, $C_{max}$ value was 81.70 µg/ml, Vss was 56.53 mL/Kg, $T_{1/2}$ was 10.10 days. It may be confirmed that the PK profiles of Herceptin and ADC110 were similar to each other, such that the binding of drug to the antibody hardly affected the pharmacokinetics in the rat.

TABLE 4

PK of ADC110 and Herceptin in Rat

|  | ADC110 | Herceptin |
|---|---|---|
| AUC (µg*day/mL) | 684.83 ± 20.38 | 622.87 ± 26.45 |
| CL (mL/day/kg) | 4.38 ± 0.13 | 4.87 ± 0.21 |
| Alpha HL (day) | 2.45 ± 0.60 | 2.16 ± 0.50 |
| Beta HL (day) | 8.55 ± 1.38 | 10.10 ± 1.81 |
| Cmax (µg/mL) | 92.18 ± 2.13 | 81.70 ± 2.41 |
| V1 (mL/kg) | 32.55 ± 0.75 | 36.72 ± 1.08 |
| Vss (mL/kg) | 43.83 ± 2.6 | 56.53 ± 4.72 |

3) In Vivo Monkey PK Test

In order to confirm pharmacokinetics of test materials at the time of intravenously administering single dose of Herceptin and ADC110 to a monkey, an experiment was performed as follows. The test materials, Herceptin and ADC110 were intravenously administered to female monkeys, respectively (Dose: 3.0 mg/kg). About 1.5 mL of blood was collected from the cephalic or femoral vein at predetermined times (30 minutes, 3 hour, 7 hours, 12 hours, 24 hours (2 days), 3 days, 4 days, 5 days, 6 days, 11 days, 15 days, 22 days, 29 days, and 36 days after administration), put into a tub filled with anticoagulant (EDTA-K2), stored in a wet-ice/Kryorack, and then centrifuged at 3,000 rpm for 10 minutes in a cold-storage state, thereby separating plasma. The separated plasma was dispensed into a micro tube and stored in a deep freezer until analysis. The test materials in the plasma were measured using LC-MS. PK analysis was performed by compartment model 2 using Phoenix™ WinNonlin® (ver. 6.3, Pharsight), and in order to quantify a drug-antibody ratio, free MMAF was quantified by LC-MS/MS after separating ADC110 using protein A beads and treating beta glucuronidase. The results were illustrated in FIGS. 20 to 22, respectively. Area under the plasma concentration-time curves (AUC), maximum blood concentrations ($C_{max}$), half-lives ($t_{1/2}$), clearances (CL), distribution half-lives (Alpha HL), secretion half-lives (beta HL), volumes of distribution (V1), and volumes of distribution (Vss) of Table 5 were calculated.

In the case of ADC110, AUC was 965.54 µg*day/mL, CL was 3.11 mL/day/Kg, $C_{max}$ value was 117.56 µg/mL, Vss was 55.65 mL/Kg, and $T_{1/2}$ was 12.79 days, and in the case of Herceptin, AUC was 689.30 µg*day/mL, CL was 4.35 mL/day/Kg, $C_{max}$ value was 83.14 µg/mL, Vss was 80.92 mL/Kg, $T_{1/2}$ was 13.44 days. It was confirmed that although the AUC of ADC 110 was slightly high, the PK profiles of Herceptin and ADC110 were entirely similar to each other, such that the binding of drug to the antibody hardly affected the pharmacokinetics in the monkey.

TABLE 5

PK of ADC110 and Herceptin in Monkey

|  | ADC110 | Herceptin |
|---|---|---|
| AUC (µg*day/mL) | 965.54 ± 33.49 | 689.30 ± 21.90 |
| CL (mL/day/kg) | 3.11 ± 0.11 | 0.30 ± 0.04 |
| Alpha HL (day) | 0.30 ± 0.04 | 0.41 ± 0.04 |
| Beta HL (day) | 12.79 ± 0.68 | 13.44 ± 0.67 |
| Cmax (µg/mL) | 117.56 ± 2.58 | 83.14 ± 1.43 |
| V1 (mL/kg) | 25.52 ± 0.56 | 36.08 ± 0.62 |
| Vss (mL/kg) | 55.65 ± 1.57 | 80.92 ± 2.17 |

At the time of comparing half-lives illustrated in the following Table 6, in the case of Kadcyla, the drug was bound to the antibody, such that the half-life was significantly decreased as compared to Herceptin, which was the original antibody, but in the case of ADC 110 prepared in Example 10 of the present invention, the half-life was similar to that of the original antibody. This means that an influence of ADC according to the present invention on the half-life of the original antibody was small.

TABLE 6

Half-life Comparison of ADC110, Herceptin, and Kadcyla

| | Terminal half-life (day) | | |
|---|---|---|---|
| | Herceptin | Kadcyla | ADC110 |
| Rat | 13.4 | 4.9~5.4 | 12.8 |
|  | (3 mpk) | (0.3~20 mpk) | (3 mpk) |
| Monkey | 6 | 1 | 8.6 |
|  | (0.5 mpk) | (0.3 mpk) | (3 mpk) |
|  | 10.1 | 5.3 |  |
|  | (3 mpk) | (30 mpk) |  |
| Human | 5.8 | 4 | — |
|  | (4 → 2 mpk) | (3.6 mpk) |  |

As illustrated in FIGS. 18 and 21, it was confirmed that ADC110 was stably bound to the antibody and MMAF drug in the blood of living organisms, which was a basic cause of high activity of ADC110 in the in vivo efficacy test as compared to Kadcyla. It may be judged from the stability as described above that ADC110 may contribute to increasing a possibility that ADC110 will exhibit more excellent efficacy in patients than that of Kadcyla, which is a control drug. It was confirmed that the drug detached from the antibody was not detected at a content more than that in the calibration curve (FIGS. 19 and 22), and this result may mean that ADC 110 may be more excellent than Kadcyla in view of stability.

INDUSTRIAL APPLICABILITY

Compounds comprising a self-immolative group according to the present invention may include a protein (for example, an oligopeptide, a polypeptide, an antibody, or the like) having substrate-specificity for a target and an active agent (for example, a drug, a toxin, a ligand, a detection probe, or the like) having a specific function or activity. The self-immolative group may be more stable in blood, plasma, and the like, as compared to the existing linker while specifically binding to a protein over-expressed in cells causing a disease, but may be separated in target cancer cells, such that the active agent may specifically act on the cells causing the disease, thereby making it possible to use the compounds to treat diseases.

The invention claimed is:
1. A compound represented by Formula I:

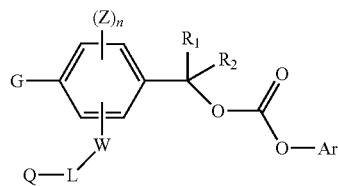

wherein:
Ar is nitrophenyl;
G is a glucuronic acid moiety or

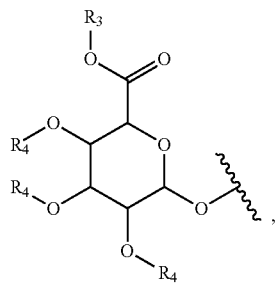

wherein $R_3$ is hydrogen or a carboxyl protecting group, and each $R_4$ is independently hydrogen or a hydroxyl protecting group;
Q is an, azide, aldehyde, ketone, trialkylsilyl, or alkyne;
L is linker connecting Q and W;
W is —C(O)—, —C(O)NR'—, —C(O)O—, —SO$_2$NR'—, —P(O)R"NR'—, —SONR'—, or —PO$_2$NR'—, in each case where the C(O), S, or P is directly bound to the phenyl ring, and R' and R" are each independently hydrogen, ($C_1$-$C_8$)alkyl, ($C_3$-$C_8$) cycloalkyl, ($C_1$-$C_8$)alkoxy, ($C_1$-$C_8$)alkylthio, mono- or di-($C_1$-$C_8$)alkylamino, ($C_3$-$C_{20}$)heteroaryl or ($C_6$-$C_{20}$) aryl;
Z is hydrogen, ($C_1$-$C_8$)alkyl, halogen, cyano or nitro;
n is an integer of 1 to 3, and when n is an integer of 2 or more, each of the Z(s) are the same as or different from each other; and
$R_1$ and $R_2$ are each independently hydrogen, ($C_1$-$C_8$)alkyl, or ($C_3$-$C_8$)cycloalkyl;
wherein either:
A) L is an alkylene chain having 1 to 50 carbon atoms and satisfies at least one of the following (i) to (iv):
(i) the alkylene includes at least one unsaturated bond,
(ii) the alkylene includes at least one heteroarylene,
(iii) at least one carbon atom of the alkylene is replaced with one or more heteroatoms selected from nitrogen (N), oxygen (O), and sulfur (S), and phosphorus (P), or
(iv) the alkylene is substituted with one or more alkyls having 1 to 20 carbon atoms; or
B) L includes at least one isoprenyl derivative unit represented by Formula A:

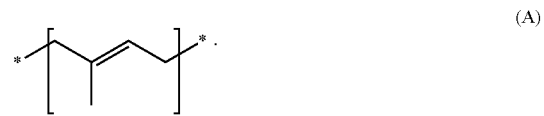

2. The compound of claim 1, wherein G is

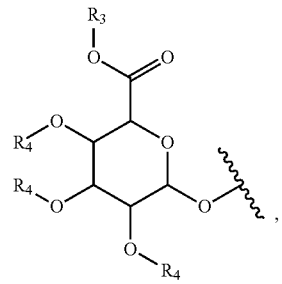

$R_3$ is hydrogen or a carboxyl protecting group, and $R_4$(s) are each independently hydrogen or a hydroxyl-protecting group.

3. The compound of claim 1, wherein W is —C(O)—, —C(O)NR'—, or —C(O)O—.

4. The compound of claim 1, wherein L is an alkylene having 1 to 50 carbon atoms and satisfies at least one of the following (i) to (iv):
(i) the alkylene includes at least one unsaturated bond,
(ii) the alkylene includes at least one heteroarylene,
(iii) at least one carbon atom of the alkylene is replaced with one or more heteroatoms selected from nitrogen (N), oxygen (O), and sulfur (S), and
(iv) the alkylene is substituted with one or more alkyls having 1 to 20 carbon atoms.

5. The compound of claim 4, wherein L is an alkylene having 1 to 50 carbon atoms and satisfies at least one of (i) or (ii):
(i) the alkylene includes at least one unsaturated bond, and
(ii) at least one carbon atom of the alkylene is replaced with one or more heteroatoms selected from nitrogen (N), oxygen (O), and sulfur (S).

6. The compound of claim 1, wherein L includes at least one isoprenyl derivative unit represented by the following Chemical Formula A, which is recognized by an isoprenoid transferase:

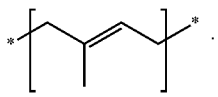

[Chemical Formula A]

7. The compound of claim 4, wherein L further includes a connection unit represented by the following Chemical Formula F or G:

—(CH₂)ᵣ(V(CH₂)ₚ)_q—      [Chemical Formula F]

—(CH₂CH₂X)_w—      [Chemical Formula G]

V is a single bond, —O—, —S—, —NR₂₁—, —C(O)NR₂₂—, —NR₂₃C(O)—, —NR₂₄SO₂—, or —SO₂NR₂₅—;

X is —O—, (C₁-C₈)alkylene, or —NR₂₁—;

R₂₁ to R₂₅ are each independently hydrogen, (C₁-C₆)alkyl, (C₁-C₆)alkyl(C₆-C₂₀)aryl, or (C₁-C₆)alkyl(C₃-C₂₀)heteroaryl;

r is an integer of 1 to 10;
p is an integer of 0 to 10;
q is an integer of 1 to 10; and
w is an integer of 1 to 10.

8. The compound of claim 1, wherein Q is a trimethylsilyl, azide, or alkyne.

9. The compound of claim 1, wherein the compound is selected from compounds having one of the following structures:

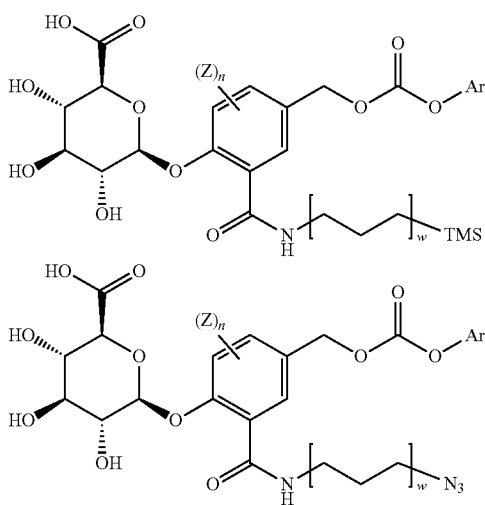

wherein:
Ar is nitrophenyl;
Z is hydrogen, (C₁-C₈)alkyl, halogen, cyano, or nitro;
X is —O—, (C₁-C₈)alkylene, or —NR₂₁—;
R₂₁ is hydrogen, (C₁-C₆)alkyl, (C₁-C₆)alkyl(C₆-C₂₀)aryl, or (C₁-C₆)alkyl(C₃-C₂₀)heteroaryl;
n is an integer of 1 to 3, and when n is an integer of 2 or more, each of the Z(s) are the same as or different from each other;
r is an integer of 1 to 10;
q is an integer of 1 to 10;
w is an integer of 1 to 10; and
x is an integer of 0 to 10.

10. The compound of claim 1, wherein Ar is 3-nitrophenyl.

11. A compound represented by formula II:

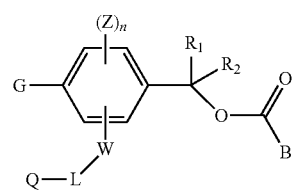

(II)

wherein:

G is a glucuronic acid moiety or

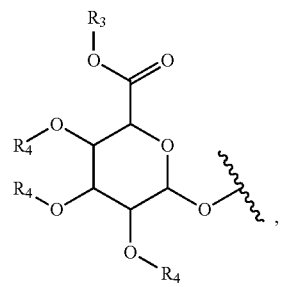

wherein R₃ is hydrogen or a carboxyl protecting group, and each R₄ is independently hydrogen or a hydroxyl protecting group;

Q is an amine, azide, trialkylsilyl, aldehyde, ketone, hydroxylamine, or alkyne;

L is linker connecting Q and W,

B is an active agent;

W is —C(O)—, —C(O)NR'—, —C(O)O—, —SO₂NR'—, —P(O)R"NR'—, —SONR'—, or —PO₂NR'—, in each case where the C(O), S, or P is directly bound to the phenyl ring, and R' and R" are each independently hydrogen, (C₁-C₈)alkyl, (C₃-C₈)cycloalkyl, (C₁-C₈)alkoxy, (C₁-C₈)alkylthio, mono- or di-(C₁-C₈)alkylamino, (C₃-C₂₀)heteroaryl or (C₆-C₂₀)aryl;

Z is hydrogen, (C₁-C₈)alkyl, halogen, cyano, or nitro;

n is an integer of 1 to 3, and when n is an integer of 2 or more, each of the Z(s) are the same as or different from each other; and R₁ and R₂ are each independently hydrogen, (C₁-C₈)alkyl or (C₃-C₈)cycloalkyl;

wherein either:

A) L is an alkylene chain having 1 to 50 carbon atoms and satisfies at least one of the following (i) to (iv):

(i) the alkylene includes at least one unsaturated bond, (ii) the alkylene includes at least one heteroarylene, (iii) at least one carbon atom of the alkylene is replaced with one or more heteroatoms selected from nitrogen (N), oxygen (O), and sulfur (S), and phosphorus (P), or (iv) the alkylene is substituted with one or more alkyls having 1 to 20 carbon atoms; or B) L includes at least one isoprenyl derivative unit represented by Formula A:

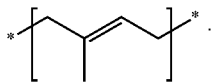
(A)

12. The compound of claim 11, wherein G is

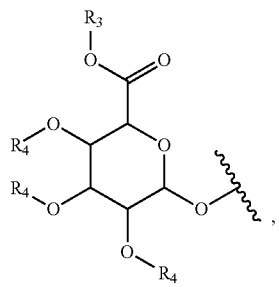

$R_3$ is hydrogen or a carboxyl protecting group, and $R_4$(s) are each independently hydrogen or a hydroxyl-protecting group.

13. The compound of claim 11, wherein W is —C(O)—, —C(O)NR'—, or —C(O)O—.

14. The compound of claim 11, wherein L is an alkylene having 1 to 50 carbon atoms and satisfies at least one of the following (i) to (iv):
(i) the alkylene includes at least one unsaturated bond,
(ii) the alkylene includes at least one heteroarylene,
(iii) at least one carbon atom of the alkylene is replaced with one or more heteroatoms selected from nitrogen (N), oxygen (O), and sulfur (S), and
(iv) the alkylene is substituted with one or more alkyls having 1 to 20 carbon atoms.

15. The compound of claim 14, wherein L is an alkylene having 1 to 50 carbon atoms and satisfies at least one of (i) or (ii):
(i) the alkylene includes at least one unsaturated bond, and
(ii) at least one carbon atom of the alkylene is replaced with one or more heteroatoms selected from nitrogen (N), oxygen (O), and sulfur (S).

16. The compound of claim 11, wherein L includes at least one isoprenyl derivative unit represented by the following Chemical Formula A, which is recognized by an isoprenoid transferase:

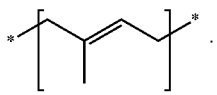
[Chemical Formula A]

17. The compound of claim 11, wherein L further includes a connection unit represented by the following Chemical Formula F or G:

—(CH$_2$)$_r$(V(CH$_2$)$_p$)$_q$—  [Chemical Formula F]

—(CH$_2$CH$_2$X)$_w$—  [Chemical Formula G]

V is a single bond, —O—, —S—, —NR$_{21}$—, —C(O)NR$_{22}$—, —NR$_{23}$C(O)—, —NR$_{24}$SO$_2$—, or —SO$_2$NR$_{25}$—;

X is —O—, (C$_1$-C$_8$)alkylene, or —NR$_{21}$—;
R$_{21}$ to R$_{25}$ are each independently hydrogen, (C$_1$-C$_6$)alkyl, (C$_1$-C$_6$)alkyl(C$_6$-C$_{20}$)aryl, or (C$_1$-C$_6$)alkyl(C$_3$-C$_{20}$)heteroaryl;
r is an integer of 1 to 10;
p is an integer of 0 to 10;
q is an integer of 1 to 10; and
w is an integer of 1 to 10.

18. The compound of claim 11, wherein Q is an amine, trimethylsilyl, azide, or alkyne.

19. The compound of claim 11, wherein the active agent is a drug, a toxin, an affinity ligand, a detection probe, or a combination thereof.

20. The compound of claim 11, wherein the active agent is an immunomodulatory compound, an anticancer agent, an antiviral agent, an antibacterial agent, an antifungal agent, an antiparasitic agent, or a combination thereof.

21. The compound of claim 11, wherein the compound is selected from compounds having one of the following structures:

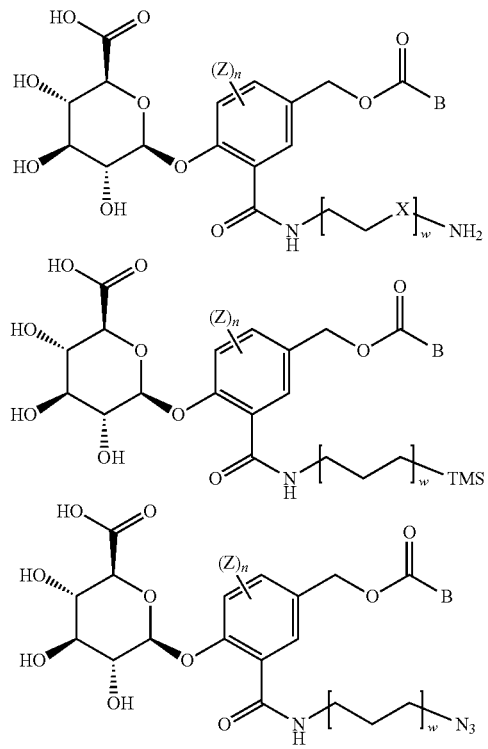

wherein:
Z is hydrogen, (C$_1$-C$_8$)alkyl, halogen, cyano, or nitro;
X is —O—, (C$_1$-C$_8$)alkylene, or —NR$_{21}$—;
R$_{21}$ is hydrogen, (C$_1$-C$_6$)alkyl, (C$_1$-C$_6$)alkyl(C$_6$-C$_{20}$)aryl, or (C$_1$-C$_6$)alkyl(C$_3$-C$_{20}$)heteroaryl;
n is an integer of 1 to 3, and when n is an integer of 2 or more, each of the Z(s) are the same as or different from each other;
r is an integer of 1 to 10;
q is an integer of 1 to 10;
w is an integer of 1 to 10;
x is an integer of 0 to 10; and
B is a drug having a structure selected from the following structures

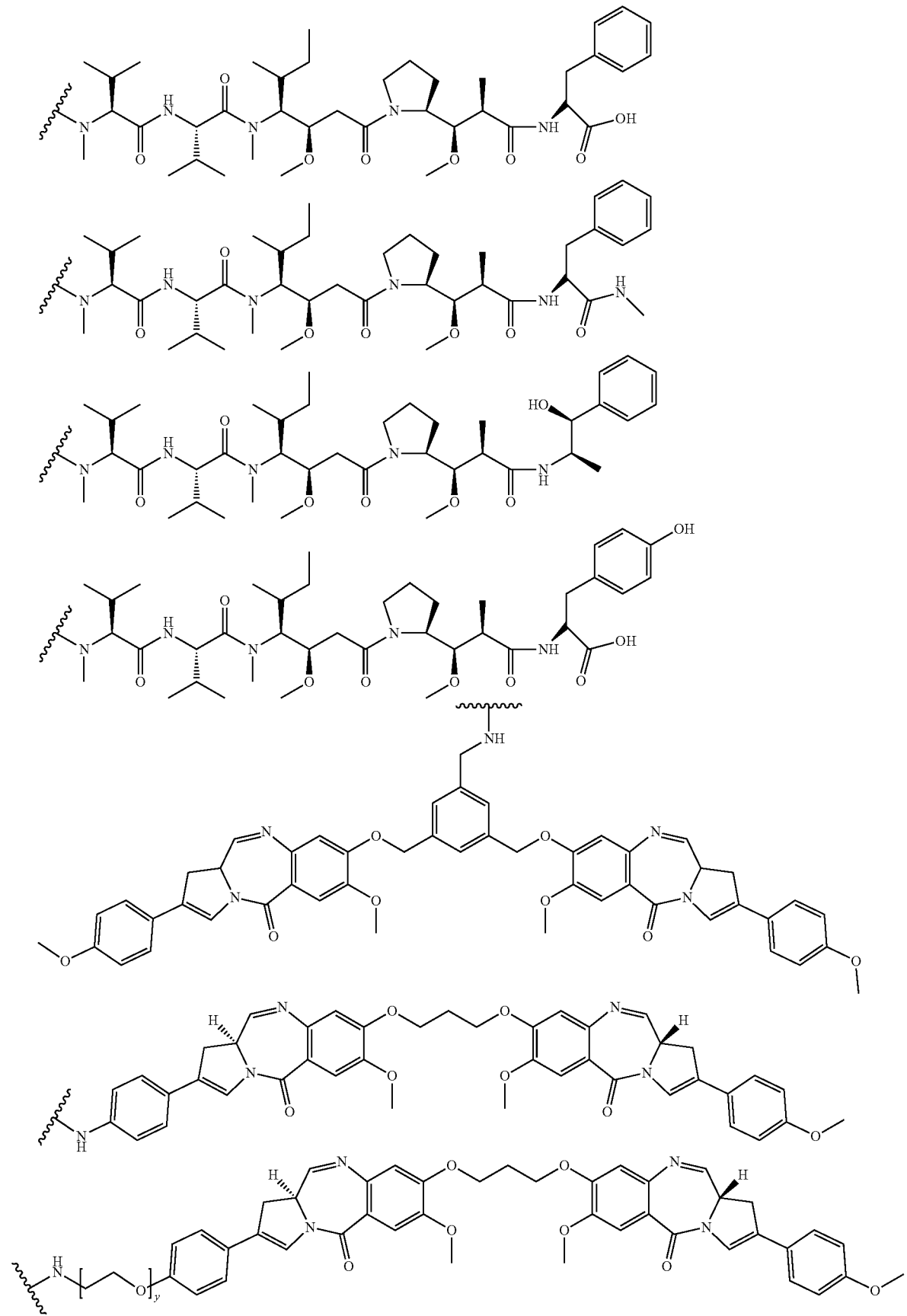

-continued
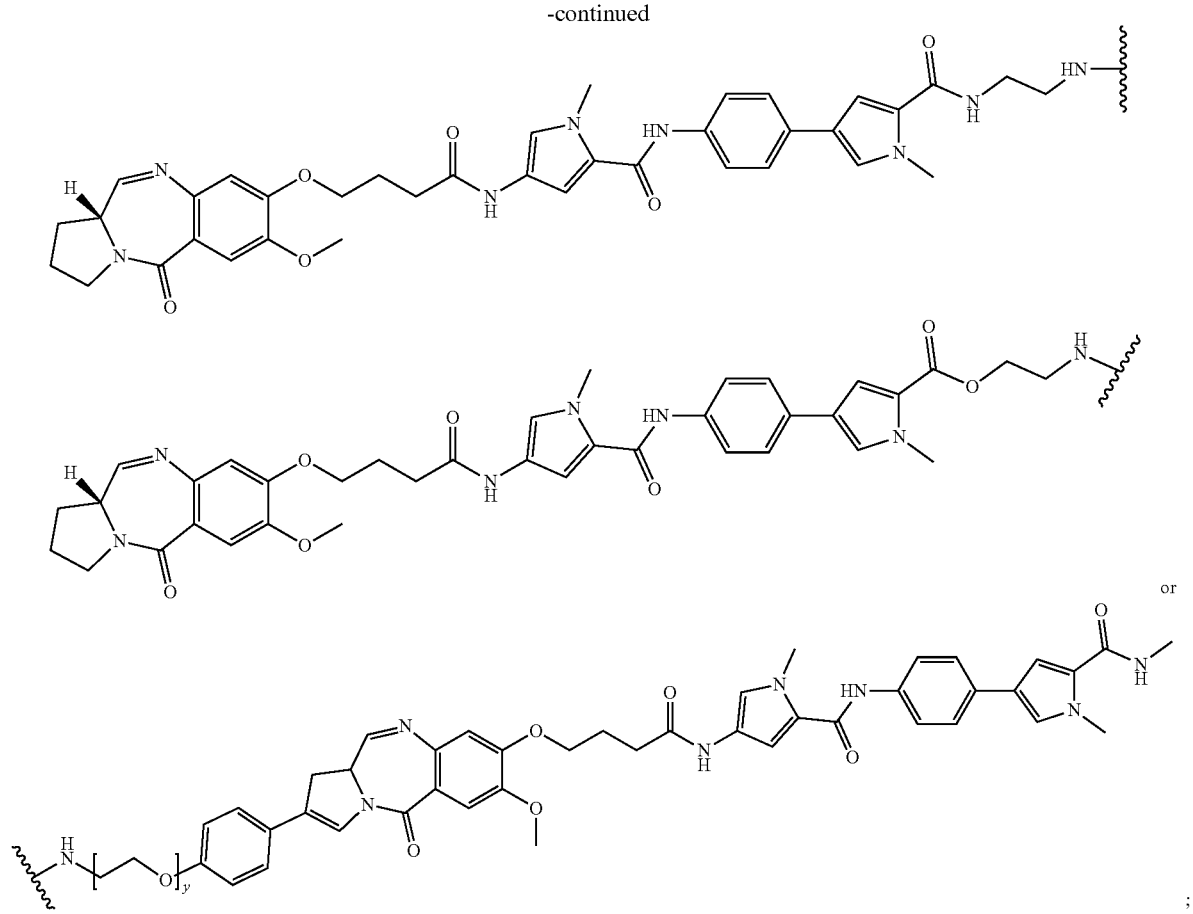
and
y is an integer of 1 to 10.

UNITED STATES PATENT AND TRADEMARK OFFICE
CERTIFICATE OF CORRECTION

PATENT NO. : 10,383,949 B2
APPLICATION NO. : 16/005245
DATED : August 20, 2019
INVENTOR(S) : Yong Zu Kim et al.

Page 1 of 1

It is certified that error appears in the above-identified patent and that said Letters Patent is hereby corrected as shown below:

On the Title Page

Item (30), Line 2, insert:
--May 26, 2015 (KR) .................... 10-2015-0073161.--

Signed and Sealed this
First Day of October, 2019

Andrei Iancu
*Director of the United States Patent and Trademark Office*